(12) United States Patent
Rajesh et al.

(10) Patent No.: US 8,372,642 B2
(45) Date of Patent: Feb. 12, 2013

(54) DIFFERENTIATION OF PLURIPOTENT CELLS

(75) Inventors: Deepika Rajesh, Madison, WI (US); Rachel Lewis, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

(21) Appl. No.: 12/715,136

(22) Filed: Mar. 1, 2010

(65) Prior Publication Data

US 2010/0279403 A1 Nov. 4, 2010

Related U.S. Application Data

(60) Provisional application No. 61/156,304, filed on Feb. 27, 2009.

(51) Int. Cl.
C12N 5/00 (2006.01)
C12N 5/02 (2006.01)

(52) U.S. Cl. ...................... 435/377; 435/325

(58) Field of Classification Search .................. None
See application file for complete search history.

(56) References Cited

U.S. PATENT DOCUMENTS

| | | | | |
|---|---|---|---|---|
| 6,815,450 | B2 | 11/2004 | He et al. | 514/294 |
| 6,943,172 | B2 | 9/2005 | Nagarathnam et al. | 514/258.1 |
| 7,348,339 | B2 | 3/2008 | Bailey et al. | 514/303 |
| 7,449,334 | B2 | 11/2008 | Thomson et al. | 435/377 |
| 7,459,424 | B2 | 12/2008 | Mochly-Rosen et al. | 514/2 |
| 2002/0076747 | A1* | 6/2002 | Price et al. | 435/69.1 |
| 2005/0214939 | A1* | 9/2005 | Gold et al. | 435/366 |
| 2006/0024827 | A1* | 2/2006 | Hwang et al. | 435/406 |
| 2006/0084168 | A1* | 4/2006 | Thomson et al. | 435/366 |
| 2007/0077654 | A1 | 4/2007 | Thomson et al. | 435/3 |

FOREIGN PATENT DOCUMENTS

| | | |
|---|---|---|
| EP | 0187371 | 7/1986 |
| EP | 1 860 180 | 11/2007 |
| WO | WO 98/03067 | 7/1998 |
| WO | WO 00/78351 | 12/2000 |
| WO | WO 2005/086902 | 9/2005 |
| WO | WO 2006/050330 | 5/2006 |
| WO | WO 2009/006930 | 1/2009 |
| WO | WO 2009/006997 | 1/2009 |
| WO | WO 2009/007852 | 1/2009 |
| WO | WO 2009/120891 | 10/2009 |
| WO | WO 2009/135206 | 11/2009 |

OTHER PUBLICATIONS

Liu et al., 2000, Immunology Today, 3: 113-116.*
Watanabe et al., 2007, Nature Biotechnology, 25: 681-686.*
Sigma-Aldrich Catalog [online], 2011 [retrieved on Oct. 2, 2011]. Retrieved from the Internet:< URL: http://www.sigmaaldrich.com/catalog/ProductDetail.do?D7=0&N5=SEARCH_CONCAT_PNO%07CBRAND_KEY&N4=S2640%7CSIGMA&N25=0&Qs=ON&F=SPEC>, 2 pages.*
Soltz et al., 1996, American Journal of Pathology, 148:129-139.*
Brenner et al., 1993, Pediatric Research, 33: 390-393, abstract only.*
Bashey et al., "Peripheral blood progenitor cell mobilization with intermediate-dose cyclophosphamide, sequential granulocyte-macrophage-colony-stimulating factor and granulocyte-colony-stimulating factor, and scheduled commencement of leukapheresis in 225 patients undergoing autologous transplantation,"*Transfusion*, 47(11):2153-2160, 2007.
Bhardwaj et al., "Sonic hedgehog induces the proliferation of primitive human hematopoietic cells via BMP regulation," *Nat. Immunol.*, 2:172-180, 2001.
Bhatia et al., "Bone morphogenetic proteins regulate the developmental program of human hematopoeitc stem cells," *J. Exp. Med.*, 189:1139-1148, 1999.
Chadwick et al., "Cytokines and BMP-4 promote hematopoietic differentiation of human embryonic stem cells," *Blood*, 102(3):906-915, 2003.
Chang et al., "Definitive-like erythroid cells derived from human embryonic stem cells coexpress high levels of embryonic and fetal globins with little or no adult globin," *Blood*, 108:1515-1523, 2006.
Christ et al., "Improved purification of hematopoietic stem cells based on their elevated aldehyde dehdrogenase activity," *Haematologica/The Hematology Journal*, 92(09):1165-1172, 2007.
Davidson and Zon, "Turning mesoderm into blood: the formation of hematopoietic stem cells during embryogenesis," *Curr. Top Dev. Biol.*, 50:45-60, 2000.
Davies et al., "The 1.8 A crystal structure and active-site architecture of beta-ketoacyl-acyl carrier protein synthase III (FabH) from *Escherichia coli*," *Structure*, 8(2):185-195, 2000.
Drexler et al., "FLT3: receptor and ligand," *Growth Factors*, 22(2):71-3, 2004.
Fadilah et al., "Cord Blood CD34+ Cells Cultured with FLT3L, Stem Cell Factor, Interleukin-6, and IL-3 Produce CD11c+CD1a−/c− Myeloid Dendritic Cells," *Stem Cells Dev.*, 16(5):849-856, 2007.
Gaur et al., "Megakaryocytes derived from human embryonic stem cells: a genetically tractable system to study megakaryocytopoiesis and integrin function," *J. Thromb. Haemost.*, 4(2):436-42, 2006.
Guo et al., "CD34− hematopoietic stem cells: Current concepts and controversies," *Stem Cells*, 21:15-20, 2003.
Hanna et al., "Treatment of sickle cell anemia mouse model with iPS cells generated from autologous skin," *Science*, 318(5858):1920-1923, 2007.
Huber et al., "Cooperative effects of growth factors involved in the induction of hematopoietic mesoderm," *Blood*, 92:4128-4137, 1998.
Ikenoya, et al., "Inhibition of Rho-kinase-induced myristoylated alanine-rich C kinase substrate (MARCKS) phosphorylation in human neuronal cells by H-1152, a novel and specific Rho-kinase inhibitor," *J. Neurochem.*, 81:9-16, 2002.

(Continued)

*Primary Examiner* — Joanne Hama
(74) *Attorney, Agent, or Firm* — Parker Highlander PLLC

(57) ABSTRACT

Provided herein are methods for the in vitro maintenance, expansion, culture, and/or differentiation of pluripotent cells, such as human embryonic stem cells (hESC) or induced pluripotent cells (iPSC), into hematopoietic precursor cells or endothelial cells. The pluripotent cells may be maintained and differentiated under defined conditions; thus, the use of mouse feeder cells or serum is not required in certain embodiments for the differentiation of the pluripotent cells into hematopoietic precursor cells or endothelial cells. The resulting hematopoietic precursor cells may be further differentiated into various myeloid or lymphoid lineages.

54 Claims, 13 Drawing Sheets

OTHER PUBLICATIONS

Kadaja-Saarepuu et al., "CD43 promotes cell growth and helps to evade FAS-mediated apoptosis in non-hematopoietic cancer cells lacking the tumor suppressors p53 or ARFCD43 promotes cell growth and inhibits FAS apoptosis," *Oncogene*, 27:1705-1715, 2007.

Karanu et al., "Differential response of primitive human CD34⁻ and CD34⁺ hematopoietic cells to the Nothc ligand Jagged-1," *Leukemia*, 17:1366-1374, 2003.

Kaufman et al., Hematopoietic colony-forming cells derived from human embryonic stem cell *Proc. Natl. Acad. Sci. USA*, 98(19):10716-10721, 2001.

Kiselyov et al., "Structural basis for a direct interaction between FGFR1 and NCAM and evidence for a regulatory role of ATP," *Structure*, 11(6):691-701, 2003.

Lappalainen et al., "A protocol for generating high numbers of mature and functional human mast cells from peripheral blood," *Clin. Experim. Allergy*, 37:1404-1414, 2007.

Lin et al., "Synthetic peptide F2A4-K-NS mimics fibroblast growth factor-2 in vitro and is angiogenic in vivo," *Int. J. Mol. Med.* 17:833-839, 2006.

Ludwig et al., "Derivation of human embryonic stem cells in defined conditions," *Nature Biotech.*, (2):185-187, 2006.

Ludwig et al., "Feeder-independent culture of human embryonic stem cells," *Nature Methods*, 3(8):637-646, 2006.

Maekawa et al., "Signaling from Rho to the Actin Cytoskeleton Through Protein Kinases ROCK and LIM-kinase ," *Science*, 285(5429):895-8, 1999.

Marshall et al., "Polarized expression of bone morphogenetic protein-4 in the human aorta-gonad-mesonephros region," *Blood*, 96:1591-1593, 2000.

Nakagawa et al. "Generation of induced pluripotent stem cells without Myc from mouse and human fibroblasts," *Nat. Biotechnol.*, 26(1):101-106, 2007.

Ng et al., "Forced aggregation of defined numbers of human embryonic stem cells into embryoid bodies fosters robust, repoducible hematopoietic differentiation," *Blood*, 106(5):1601-1603, 2005.

Pearson et al., "The stepwise specification of embryonic stem cells to hematopoietic fate is driven by sequential exposure to Bmp4, activin A, bFGF and VEGF," *Development*, 135:1525-1535, 2008.

Peng et al., "Effects of thymic polypeptides on the thymopoiesis of mouse embryonic stem cells," *Cell Biology International*, 32(10): 1265-1271, 2008.

Pick et al., "Differentiation of human embryonic stem cells in serum-free medium reveals distinct roles for bone mrophogenetic protein 4, vascular endothelial growth factor, stem cell factor, and fibroblast growth factor 2 in hematopoiesis," *Stem Cells*, 25(9):2206-2214, 2007.

Ratajczak et al., "Effect of basic (FGF-2) and acidic (FGF-1) fibroblast growth factors on early haemopoietic cell development," *Br. J. Haematol.*, 93(4):772-782, 1996.

Sasaki et al.; "The novel and specific Rho-kinase inhibitor (S)-(+)-2-methyl-1-[(4-methyl-5-isoquinoline)sulfonyl]-homopiperazine as a probing molecule for Rho-kinase-involved pathway," *Pharmacol. Ther.*, 93:225, 2002.

Schernthaner et al., "Expression, epitope analysis, and functional role of the LFA-2 antigen detectable on neoplastic mast cells," *Blood*, 98:3784-3792, 2001.

Slukvin et al. In: *Directed Production of Specific Blood Lineages from Human Embryonic Stem Cells*, #33, ASCI/AAP Joint Meeting Posters, 2007.

Takahashi et al., "Induction of pluripotent stem cells from adult human fibroblasts by defined factors," *Cell*, 131(5):861-872, 2007.

Takahashi et al., "Induction of pluripotent stem cells from fibroblast cultures," *Nat. Protoc.*, 2(12):3081-3089, 2007.

U.S. Appl. No. 61/015,813 entitled "Methods and Compositions for the Differentiation of Stem Cells," submitted to the United States Patent Office on Dec. 21, 2007.

Ungrin et al., "Reproducible, ultra high-throughput formation of multicellular organization from single cell suspension-derived human embryonic stem cell aggregates," *PloS ONE*, 3(2):e1565 (12 pages), Feb. 2008.

Vodyanik et al., "Leukosialin (CD43) defines hematopoietic progenitors in human embryonic stem cell differentiation cultures," *Blood*, 108(6):2095-105, 2006.

Wagemaker et al., "Interleukin-3," *Biotherapy*, 2(4):337-345, 1990.

Wang et al., "Derivation and characterization of hematopoietic cells from human embryonic stem cells," *Methods Mol. Biol.*, 331:179-200, 2006.

Wang et al., "Endothelial cells derived from human embryonic stem cells form durable blood vessels in vivo," *Nature Biotech.*, 25(3):317-318, 2007.

Yamamura et al., "Ex vivo culture of human cord blood hematopoietic stem/progenitor cells adversely influences their distribution to other bone marrow compartments after intra-bone marrow transplantation," *Stem Cells*, 26(2):543-9, 2008.

Yu et al., "Induced pluripotent stem cell lines derived from human somatic cells," *Science*, 318(5858):1917-1920, 2007.

Zambidis et al., "Expression of ACE (CD143) identifies and regulates primitive hemangioblasts derived from human pluripotent stem cells," *Blood*, prepublished online Sep. 5, 2008, doi:10.1182/blood-2008-03-144766, 40 pages.

Zambidis et al., "Expression of angiotenin-converting enzyme (CD143) identifies and regulates primitive hemangioblasts derived from human pluripotent stem cells," *Blood*, 112:3601-3614, 2008.

Zambidis et al., "Hematopoietic differentiation of human embryonic stem cells progresses through sequential hematodendothelial, primitive, and definitive stages resembling human yolk sac development," *Blood*, 106:860-870, 2005.

Zandstra et al., "Cytokine manipulation of primitive human hematopoietic cell self-renewal," *Proc. Natl. Acad. Sci., USA*, 94:4698-4703, 1997.

Bhatia, "Hematopoiesis from human embryonic stem cells," *Annals of the New York Academy of Sciences*, 1106:219-222, 2007.

Chute et al., "A comparative study of the cell cycle status and primitive cell adhesion molecule profile of human CD34+ cells cultured in stroma-free versus porcine microvascular endothelial cell cultures," *Experimental Hematology*, 27(2):370-379, 1999.

Kennedy et al., "Development of the hemangioblast defines the onset of hematopoiesis in human ES cell differentiation cultures," *Bood*, 109(7):2679-2687, 2007.

Mohamed et al., "Ex vivo expansion of stem cells: defining optimum conditions using various cytokines," *Laboratory Hematology: Official Publication of the International Society for Laboratory Hematology*, 12(2) 86-93, 2006.

Nakayama et al., "Vascular endothelial growth factor synergistically enhances bone morphogenetic protein-4-dependent lymphohematopoietic cell generation from embryonic stem cells in vitro," 95(7):2275-2283, 2000.

Norol et al., "Ex vivo expanded mobilized peripheral blood cd34+ cells accelerate haematological recovery in a baboon model of autologous transplantation," *British Journal of Haematology*, 109:162-172, 2000.

Park et al., "A hierarchical order of factors in the generation of FLK1- and SCL-expressing hematopoietic and endothelial progenitors from embryonic stem cells," *Development*, 131(11):2749-2462, 2004.

PCT International Search Report, issued in International application No. PCT/US2010/025776, mailed Jul. 14, 2010.

Purpura ety al., "Analysis of the temporal and concentration-dependent effects of BMP-4, VEGF, and TPO on development of embryonic stem cell-derived mesoderm and blood progenitors in a defined, serum-free media," *Experimental Hematology*, 36(9):1186-1198, 2008.

Shiozawa et al., "Human osteoblasts support hematopoietic cell development in vitro," *Acta Haematologica*, 120(3):134-145, 2008.

Slack et al., "Mesoderm induction by fibroblast growth factor in early xenopus development," *Philosophical Transactions of the Royal Society of London B Biological Sciences*, 327(1239):75-84, 1990.

Tian et al., "Differentiation of embryonic stem cells towards hematopoietic cells: progress and pitfalls," *Current Opinion in Hematology*, 1594):312-318, 2008.

Wang et al., "Endothelial and hematopoietic cell fate of human embryonic stem cells originates from primitive endothelium with emangioblastic properties," *Immunity*, 21(1):31-41, 2004.

Wang et al., "MBP4 and TGFbeta differentially regulate CD34+ progenitor development in human embryonic stem cells through SMAD-dependent pathway," *Blood (ASH Annual Meeting Abstracts)*, vol. 112, Abstract 889, 2008.

Wu et al., "Optimization of culture conditions to enhance transfection of human CD34+ cells by electroporation," *Bone Marrow Transplantation*, 27(11):1201-1209, 2001.

Yamashita et al., "Differentiation of arterial, venous, and lymphatic endothelial cells from vascular progenitors," *Trends in Cardiovascular Medicine*, 17(2):59-63, 2007.

Yang et al., "Hematopoietic reconstitution of fresh and cultured cord blood CD34+ cells in NOD/SCID mice," *Chinese Journal of Cellular and Molecular Immunology*, 24(10):947-949, 2008. (English abstract).

Zhang et al., "Short-term BMP-4 treatment initiates mesoderm induction in human embryonic stem cells," *Blood*, 111(4):1933-1941, 2008.

* cited by examiner

DIFFERENTIATION OF PLURIPOTENT CELLS

This application claims priority to U.S. Application No. 61/156,304 filed on Feb. 27, 2009, the entire disclosure of which is specifically incorporated herein by reference in its entirety without disclaimer.

BACKGROUND OF THE INVENTION

1. Field of the Invention

The present invention relates generally to the fields of molecular biology and medicine. More particularly, it concerns methods and compositions for the production of hematopoietic progenitor cells from embryonic stem cells.

2. Description of Related Art

Due to the significant medical potential of hematopoietic stem and progenitor cells, substantial work has been done to try to improve methods for the differentiation of hematopoietic progenitor cells from pluripotent stem cells. In the human adult, a small number of hematopoietic stem cells present primarily in bone marrow produce heterogeneous populations of actively dividing hematopoietic (CD34+) progenitor cells that differentiate into all the cells of the blood system. However, the CD34+ marker is an imprecise definition of hematopoietic cells since other cell types, notably endothelial cells (blood vessels), also express CD34. Other markers, such as the CD43 marker, may also be used to help identify hematopoietic progenitor cells (e.g., Kadaja-Saarepuu et al., 2007; Vodyanik et al., 2006). In an adult human, hematopoietic progenitors proliferate and differentiate resulting in the generation of hundreds of billions of mature blood cells daily. Hematopoietic progenitor cells are also present in cord blood. In vitro, human embryonic stem cells are capable of indefinite proliferation in culture and are thus capable, at least in principle, of supplying cells and tissues for the replacement of failing or defective human tissue.

The culture of human pluripotent cells with feeder cell lines such as mouse fibroblasts, presents the risk of unexpected transformations that have previously been associated with interspecies exposure during co-culture. Since one of the objectives of human pluripotent stem cell cultures is to create tissues which can ultimately be transplanted into a human body, it is highly desirable that the stem cells are not exposed to cells of another species or to a medium which has been used to culture cells of another species. Accordingly, defining a culture condition that will permit the differentiation of human pluripotent stem cells into the hematopoietic lineage without a co-culture step of any kind, is of great interest in the continued development of techniques for the production of human hematopoietic progenitor cells from human pluripotent stem cells.

Using serum in differentiation medium can also present certain drawbacks and limitations. Serum, e.g., as shown in Chadwick et al. (2003), is an animal product that presents uncertainties regarding the composition of serum across different batches (e.g., regarding variations in the presence and/or concentration of growth factors, etc.). These uncertainties may also contribute to increased variability in the proportion of hematopoietic cells produced across experiments. Additionally, the use of serum may present substantial regulatory issues during clinical development, further complicating commercialization.

There currently exists a clear need for methods of differentiating pluripotent stem cells into hematopoietic progenitor cells without exposing the cells to material from another animal species. Due to the complexities associated with the maintenance and differentiation of pluripotent cells, it is currently not clear how various pluripotent cells may respond to subsequent exposure to growth factors after maintenance in various defined media, as compared to maintenance on mouse feeder cells. Clearly, there is a need for improved methods for the differentiation of pluripotent cells into hematopoietic precursor cells.

SUMMARY OF THE INVENTION

Provided herein are methods for the in vitro differentiation pluripotent cells, which have been expanded and/or maintained under defined conditions, into hematopoietic precursor cells or endothelial cells. These methods overcome limitations in the prior art by providing a process which may be carried out under defined conditions. Accordingly, these methods may be advantageously used to produce, e.g., hematopoietic precursor cells (HPCs), or further differentiated myeloid or lymphoid lineages, which may be administered to a subject (e.g., a human patient) with reduced clinical concerns which would otherwise be associated with the use of cells which have been exposed to animal products such as mouse fibroblasts and/or serum.

An aspect of the present invention relates to a method of differentiating pluripotent cells into hematopoietic precursor cells or endothelial cells comprising the sequential steps of: (a) culturing or maintaining a plurality of substantially undifferentiated pluripotent cells in a first defined media comprising at least one growth factor, (b) incubating the cells in a second defined media which is essentially free of BMP4, VEGF, IL-3, Flt3 ligand, and GMCSF, (c) culturing the cells in a third defined media comprising an amount of BMP4 and VEGF sufficient to expand or promote differentiation in a plurality of the cells, and (d) culturing the cells in a fourth defined media comprising an amount of either (1) IL-3 and Flt3 ligand, or (2) VEGF, FGF-2 or an FGF-2 mimic, and IGF sufficient to expand or promote differentiation in a plurality of the cells; wherein a plurality of the pluripotent cells are differentiated into hematopoietic precursor cells or endothelial cells. In certain embodiments, combination (1) above may be used to promote differentiation into hematopoietic precursor cells. Combination (2) above may be used to promote differentiation into an endothelial cell or an endothelial progenitor cell. The second defined media may be free or essentially free of FGF-2, IL6, SCF and/or TPO. The third defined media may also include FGF-2 (e.g., from about 5-50 ng/ml or from about 10-25 ng/ml) or an FGF-2 mimic. As shown in the below examples, inclusion of FGF-2 in the third media can increase the efficiency of differentiation of pluripotent cells into hematopoietic precursor cells. In certain embodiments, the fourth defined media further comprises GMCSF, or at least one of IL-6, SCF, or TPO. In certain embodiments, the fourth defined media includes an amount of either: (1) IL-3, Flt3 ligand, and GMCSF, or (2) IL-3, Flt3 ligand, SCF, IL-6, and TPO sufficient to promote differentiation of the cells. The third defined media and/or the fourth defined media may further comprise BIT9500 or Serum Replacement 3. The method may comprise culturing cells in a defined media which includes BIT9500 or Serum Replacement 3. At least some of the cells may be at least partially separated or are substantially individualized prior to step (b). The cells may be substantially individualized using an enzyme, such as a trypsin. The cells may be contacted with a ROCK inhibitor and a trypsin inhibitor (e.g., a soybean trypsin inhibitor) subsequent to said individualization. The ROCK inhibitor may be selected from the list consisting of HA-100, H-1152, and Y-27632. A plurality of the pluripotent cells may form embryoid bodies (EBs). From about 200 to about 1000 cells per aggregate may be used to generate at least one of said EBs. The method may comprise culturing the cells at an atmospheric pressure of less than 20% oxygen or at an atmospheric pressure of about 5% oxygen. As shown in the below examples, differentiating cells under hypoxic conditions, such as at about 5% atmospheric $O_2$, can increase the differentiation of the cells, e.g., into hematopoietic and/or endothelial precursor cells.

In certain embodiments, said cells may be partially or substantially reaggregated at least once. The cells may be reaggregated after culture in the third defined media and prior to or during culture in the fourth defined media. The reaggregation may comprise exposing said cells to trypsin or TRYPLE. Said cells may be exposed to a ROCK inhibitor subsequent to the reaggregation, or said cells may be cultured in a media essentially free of a ROCK inhibitor subsequent to the reaggregation. The method may further comprise culturing the cells at an atmospheric pressure of less than about 20% oxygen, wherein from about 200 to about 1000 cells per aggregate are used to generate a plurality of embryoid bodies (EBs). The first defined media may comprise TeSR, mTeSR, or mTeSR1. Step (a) may comprise culturing the cells on a matrix-coated surface. The matrix may comprise laminin, vitronectin, gelatin, polylysine, thrombospondin or Matrigel™. The second defined media may comprise TeSR-GF or X-vivo15 media. The second defined media may further comprise about 0.1 ng/ml TGF-β and about 20 ng/ml FGF-2. Step (b) may comprise incubating the cells for a period of from about 12 hours to about 3 days. Step (c) may comprise culturing or differentiating the cells for a period of from about 4 to about 8 days. Step (d) may comprise culturing the cells for a period of at least about 4, or from about 4 to about 8 days. A plurality of the pluripotent cells may be differentiated into multipotent heamatopoietic, or myeloid progenitor cells. In certain embodiments, the myeloid progenitor cells co-express CD31, CD43, and CD45. The myeloid progenitor cells may be common myeloid progenitors. The third defined media comprises about 10-50 ng/ml BMP4 and about 10-50 ng/ml VEGF. In certain embodiments, the third defined media further comprises 10-50 ng/ml FGF-2. The third defined media comprises about 25 ng/ml BMP4 and about 25 ng/ml VEGF. The fourth defined media may comprise about 5-25 ng/ml IL-3 and about 10-50 ng/ml Flt3 ligand. The fourth defined media may further comprise about 5-25 ng/ml GMCSF, or about 10-100 ng/ml or about 10-50 ng/ml TPO, about 10-100 ng/ml SCF, about 5-25 ng/ml IL-6, and about 5-25 ng/ml IL-3. The fourth defined media may comprise about 10 ng/ml IL-3, about 25 ng/ml Flt3 ligand, and about 10 ng/ml GMCSF. A plurality of the hematopoietic precursor cells may express at least two cell markers selected from the list comprising CD43, CD34, CD31 and CD45. A plurality of the hematopoietic precursor cells may express CD34, CD43, CD45 and CD31. In certain embodiments, the hematopoietic precursor cells are multipotent hematopoietic precursor cells that co-express CD34, CD43, CD45 and CD31.

One or more of the hematopoietic precursor cells may be differentiated into a myeloid cell or a lymphoid cell. The myeloid cell may be a macrophage, mast cell, erythrocyte, megakaryocyte/platelet, dendritic cell, or polymorph nuclear granulocyte (e.g., a eosinophil, basophil, neutrophil, monocyte, or macrophage).

In certain embodiments, a fifth defined media may be used to further promote differentiation of the cells into a particular cell type; for example, various media may be used to promote differentiation of the hematopoietic precursor cells into a more differentiated cell type such as, for example, an erythroblast, a NK cell, or a T cell. The method may further comprise culturing a plurality of said cells in a fifth defined media comprising one or more growth factor selected from the list consisting of IL-3, IL-6, SCF, EPO, and TPO, in an amount sufficient to promote differentiation of a plurality of the cells into erythroblasts. A plurality of the cells are cultured in a fifth defined media comprising one or more growth factor selected from the list consisting of IL-7, SCF, and IL-2, in an amount sufficient to promote differentiation of the cells into NK cells. The method may further comprise culturing a plurality of said cells in a fifth defined media comprising Notch ligand and one or more growth factor selected from the list consisting of IL-7, SCF, and IL-2 in an amount sufficient to promote differentiation of the cells into T cells. The Notch ligand may be the Fc chimeric Notch DLL-1 ligand or Notch ligand produced by a stromal cell line which over-expresses the Notch ligand. In certain embodiments, a thymic peptide such thymosin alpha, thymopenin, or thymosin B4 may be used to further promote differentiation of the cells into T cells (e.g., as described in Peng et al., 2008). In certain embodiments, the plurality of said cells comprise hematopoietic precursor cells. The third defined media may comprise one or more growth factor selected from the list consisting of SCF, IL-6, G-CSF, EPO, TPO, FGF2, IL-7, IL-11, IL-9, IL-13, IL-2, or M-CSF in an amount sufficient to promote expansion or further differentiation of the cells. The fourth defined media may comprise one or more growth factor selected from the list consisting of SCF, IL-6, G-CSF, EPO, TPO, FGF2, BMP4, VEGF, IL-7, IL-11, IL-9, IL-13, IL-2, or M-CSF in an amount sufficient to promote expansion or further differentiation of the cells. In certain embodiments, the method may comprise incubating the cells in a fifth defined media which includes one or more growth factor selected from the list consisting of SCF, IL-6, G-CSF, EPO, TPO, FGF2, IL-7, IL-11, IL-9, IL-13, IL-2, or M-CSF in an amount sufficient to promote expansion or further differentiation of the cells.

Said pluripotent cells are preferably mammalian pluripotent cells. In certain embodiments the pluripotent cells are human pluripotent cells, such as human embryonic stem cells (hESC) or induced pluripotent cells (iPSC). The hESC comprise cells may be selected from the list consisting of H1, H9, hES2, hES3, hES4, hES5, hES6, BG01, BG02, BG03, HSF1, HSF6, H1, H7, H9, H13B, and H14. Said iPSC may be selected from the list consisting of iPS6.1, iPS 6.6, iPS, iPS 5.6, iPS iPS 5.12, iPS 5.2.15, iPS iPS 5.2.24, iPS 5.2.20, iPS 6.2.1, iPS-Bl-SONL, iPS-Bl-SOCK, iPS-TIPS1EE, iPS-TiPS IB, iPS-KIPS-5, and iPS 5/3-4.3.

Another aspect of the present invention related to hematopoietic precursor cell differentiated according to the methods described herein or derived from a separate hematopoietic precursor cell differentiated according to the methods described herein. The hematopoietic precursor cell may express two, three or all of CD34, CD43, CD45, and CD31. Yet another aspect of the present invention relates to a myeloid cell, a myeloid progenitor, or a common myeloid progenitor derived from a hematopoietic precursor cell differentiated according to the methods described herein. The myeloid cell may be selected from the list consisting of monocyte, macrophage, neutrophil, basophil, eosinophil, erythrocyte, megakaryocyte/platelet, and dendritic cell. In certain embodiments, the myeloid cell is an erythrocyte. The myeloid cell, myeloid progenitor, or the common myeloid progenitor may be comprised in a pharmaceutical preparation.

Another aspect of the present invention relates to a lymphoid cell derived from a hematopoietic precursor cell differentiated according to the methods described herein. The lymphoid cell may be a T-cell, B-cell, or a natural killer cell. The lymphoid cell may be comprised in a pharmaceutical preparation.

Yet another aspect of the present invention relates to an endothelial cell, endothelial precursor cell, or mesenchymal cell differentiated according to the methods described herein. It is anticipated that various groups of endothelial cells may be produced via the methods described herein. The endothelial cell may be of a particular endothelial cell type such as: lymphatic or vascular (e.g., expressing LYVE1 or podoplanum), vascular arterial (e.g., expressing Notch 1 and Notch, Jagged 1 and Jagged 2), vascular venous (e.g., expressing EphB4, Lefty 1 and Lefty 2), or organ-specific endothelial cells (e.g., endocardial cells, renal cells, cells in the lung or blood, and blood-brain barrier cells). Morphologically, the endothelial cell may be continuous, fenestrated or discontinuous.

"Individualizing cells," as used herein, refers to the disassociation or separation of cells into smaller groups of cells or individual cells, e.g., as a result of mechanical separation or exposure to a proteolytic enzyme such as trypsin or TrypLE™. In certain embodiments, cultures which have been individualized may still comprise small clumps of cells, e.g., clumps of cells comprising about 2-10 cells.

A media is said to be "essentially free" of a growth factor if the growth factor is absent from the media or if the growth factor is present in the media in an amount which is insufficient to promote any substantial expansion and/or differentiation of cells in the media, or is present at a concentration below a detectable limit. It will be recognized that a media which is essentially free of a growth factor may nonetheless contain trace amounts of the growth factor in the media.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
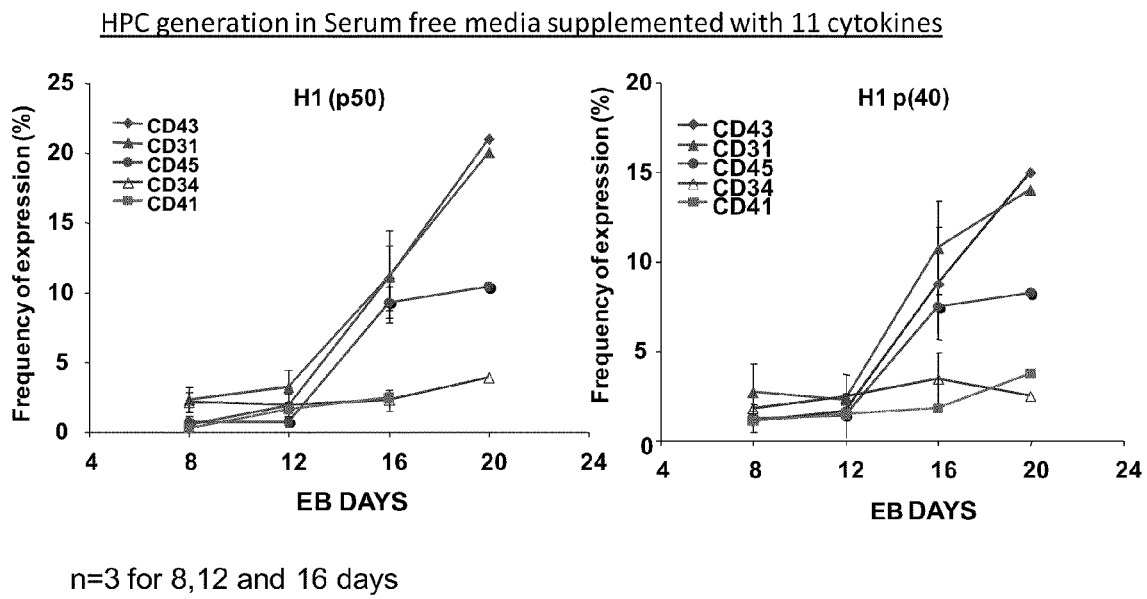
FIG. 1: Hematopoietic differentiation of H1 hESCs at passage 50 (A) and 40 (B) (n=3 experiments for 8, 12, and 16 days).

Provided herein are methods for the in vitro differentiation of pluripotent cells, such as human embryonic stem cells (hESC) or induced pluripotent cells (iPSC), into hematopoietic precursor cells and/or endothelial cells. The pluripotent cells may be both maintained, expanded, and differentiated under defined conditions; thus, the use of mouse feeder cells or serum is not required for the differentiation of the pluripotent cells into hematopoietic precursor cells and/or endothelial cells. The resulting hematopoietic precursor cells may be further differentiated into various myeloid (e.g., monocyte, macrophage, neutrophil, basophil, eosinophil, erythrocyte, megakaryocyte/platelet, or dendritic cell) or lymphoid (e.g., T-cell, B-cell, or natural killer cell) lineages. Pluripotent cells may be expanded and maintained in an essentially undifferentiated state under defined conditions (e.g., using a TeSR media) prior to differentiation of the pluripotent cells.

In particular, the inventor has discovered that certain growth factors are particularly important for the differentiation of pluripotent cells which have been maintained under defined conditions. In certain embodiments, pluripotent cells may be sequentially exposed to several defined media to promote differentiation into hematopoietic precursor cells. After culture and maintenance of the pluripotent cells in an essentially undifferentiated state in a first defined media (e.g., in a TeSR media), the cells may be exposed to a second defined media containing no or essentially no BMP4, VEGF, IL-3, Flt3 ligand, or GMCSF. The cells may then be exposed to a third defined media comprising BMP4, VEGF, IL-3, Flt3 ligand, and GMCSF to promote hematopoietic differentiation; alternately, the cells may be exposed to a third defined media comprising BMP4 and VEGF, and optionally FGF-2; followed by exposure to a fourth media comprising IL-3, Flt3 ligand, and GMCSF. The inventor has discovered that sequential exposure to a third defined media comprising BMP4 and VEGF, followed by exposure to a fourth media comprising IL-3, Flt3 ligand, and GMCSF can surprisingly result in substantial increases in the generation of hematopoietic precursor cells. As shown in the below examples, inclusion of FGF-2 in the third defined media resulted in a surprising increase in the differentiation of pluripotent cells into hematopoietic precursor cells. It has also been discovered that hypoxic conditions (e.g., exposure to an atmospheric pressure 5% $O_2$), at least partial reaggregation of cells (e.g., using trypsin or TrypLE™), and/or formation of aggregates using defined ranges of cells in the formation of embryoid bodies (e.g., from about 200-1000 cells per aggregate) can also be used to further promote differentiation into hematopoietic precursor cells.

I. Preparation and Maintenance of Embryonic Stem Cells

Pluripotent cells may be cultured and maintained in an undifferentiated state using a variety of methods prior to hematopoietic differentiation. In certain embodiments, pluripotent cells may be cultured and maintained in an essentially undifferentiated state using defined, feeder-independent culture system, such as a TeSR medium. Alternately, undefined conditions may be used; for example, pluripotent cells may be cultured on fibroblast feeder cells or a medium which has been exposed to fibroblast feeder cells in order to maintain the stem cells in an undifferentiated state.

Feeder-independent culture systems and media may be used to culture and maintain pluripotent cells, such as hESC or iPSC. These approaches allow human embryonic stem cells to remain in an essentially undifferentiated state without the need for mouse fibroblast "feeder layers." As described herein, various modifications may be made to these methods in order to reduce costs etc. as desired.

It is anticipated that virtually any pluripotent or human embryonic stem cell line may be differentiated into hematopoietic progenitor cells under defined conditions as described herein. For example, human embryonic stem cell line H1, H9, hES2, hES3, hES4, hES5, hES6, BG01, BG02, BG03, HSF1, HSF6, H1, H7, H9, H13B, and/or H14 etc. may be differentiated into hematopoietic precursor cells via methods described herein. It is anticipated that stem cell lines which subsequently become available may also be differentiated into hematopoietic precursor cells via the methods described herein. Although human pluripotent cells may be preferably used in certain embodiments, in some instances it may also be possible to use other pluripotent cells, such as mammal, mouse, primate, etc. for hematopoietic differentiation.

In addition to human embryonic stem cells, iPS cells may be cultured and/or differentiated into hematopoietic precursor cells via the methods described herein. iPS cells are reprogrammed somatic cells that act like stem cells (Takahashi et al., 2007; Takahashi et al., 2007; Nakagawa et al., 2007). As would be appreciated by one of skill, the term "pluripotent cells" includes both cells that naturally occur in or are derived from a blastocyst as well as cells that have been induced to de-differentiate into stem cells or return to a stem-cell-like state (see, e.g., Nakagawa et al., 2007; Yu et al., 2007).

A. TeSR Medium

TeSR media are defined media which may be used to culture undifferentiated human embryonic stem cells. TeSR media includes both TeSR1 media and mTeSR media. TeSR includes bFGF, LiCl, γ-aminobutyric acid (GABA), pipecolic acid and TGFβ, and various methods utilizing TeSR have been described previously, e.g., in U.S. Application 2006/0084168 and Ludwig et al. (2006a; 2006b), which are incorporated by reference in their entirety.

TeSR media typically include inorganic salts, trace minerals, energy substrates, lipids, amino acids, vitamins, growth factors and proteins, and other components. The complete formulation for TeSR1 medium is shown below in Table 1.

TABLE 1

Complete Formulation for TeSR1 Medium

| | mM |
|---|---|
| INORGANIC SALTS | |
| Calcium chloride (Anhydrous) | 8.24E−01 |
| HEPES | 1.18E+01 |
| Lithium Chloride (LiCl) | 9.80E−01 |
| Magnesium chloride (Anhydrous) | 2.37E−01 |
| Magnesium Sulfate (MgSO4) | 3.19E−01 |
| Potassium chloride (KCl) | 3.26E+00 |
| Sodium bicarbonate (NaHCO3) | 1.80E+01 |
| Sodium chloride (NaCl) | 9.46E+01 |
| Sodium phosphate, dibas (Anhydrous) | 3.92E−01 |
| Sodium phosphate, mono. (NaH2PO4—H2O) | 3.55E−01 |
| TRACE MINERALS | |
| Ferric Nitrate (Fe(NO3)3—9H2O) | 9.71E−05 |
| Ferric sulfate (FeSO4—7H2O) | 1.18E−03 |
| Cupric sulfate (CuSO4—5H2O) | 4.08E−06 |
| Zinc sulfate (ZnSO4—7H2O) | 1.18E−03 |
| Ammonium Metavanadate NH4VO3 | 1.09E−05 |
| Mangenous Sulfate Mn SO4 H2O | 1.97E−06 |
| NiSO4 6H2O | 9.70E−07 |
| Selenium | 1.77E−04 |
| Sodium Meta Silicate Na2SiO3 9H2O | 9.66E−04 |
| SnCl2 | 1.24E−06 |
| Molybdic Acid, Ammonium salt | 1.97E−06 |
| CdCl2 | 1.22E−05 |
| CrCl3 | 1.98E−06 |
| AgNO3 | 9.81E−07 |

TABLE 1-continued

Complete Formulation for TeSR1 Medium

| | mM |
|---|---|
| AlCl3 6H2O | 4.87E−06 |
| Ba (C2H3O2)2 | 9.79E−06 |
| CoCl2 6H2O | 9.81E−06 |
| GeO2 | 4.97E−06 |
| KBr | 9.89E−07 |
| KI | 1.00E−06 |
| NaF | 9.83E−05 |
| RbCl | 9.81E−06 |
| ZrOCl2 8H2O | 9.80E−06 |
| ENERGY SUBSTRATES | |
| D-Glucose | 1.37E+01 |
| Sodium Pyruvate | 3.92E−01 |
| LIPIDS | |
| Linoleic Acid | 1.88E−04 |
| Lipoic Acid | 4.00E−04 |
| Arachidonic Acid | 1.29E−05 |
| Cholesterol | 1.12E−03 |
| DL-alpha tocopherol-acetate | 2.90E−04 |
| Linolenic Acid | 6.99E−05 |
| Myristic Acid | 8.59E−05 |
| Oleic Acid | 6.94E−05 |
| Palmitic Acid | 7.65E−05 |
| Palmitoleic acid | 7.71E−05 |
| Stearic Acid | 6.89E−05 |
| AMINO ACIDS | |
| L-Alanine | 1.37E−01 |
| L-Arginine hydrochloride | 5.48E−01 |
| L-Asparagine-H2O | 1.37E−01 |
| L-Aspartic acid | 1.37E−01 |
| L-Cysteine-HCl—H2O | 7.83E−02 |
| L-Cystine 2HCl | 7.83E−02 |
| L-Glutamic acid | 1.37E−01 |
| L-Glutamine | 2.94E+00 |
| Glycine | 2.94E−01 |
| L-Histidine-HCl—H2O | 1.18E−01 |
| L-Isoleucine | 3.26E−01 |
| L-Leucine | 3.54E−01 |
| L-Lysine hydrochloride | 3.91E−01 |
| L-Methionine | 9.06E−02 |
| L-Phenylalanine | 1.69E−01 |
| L-Proline | 2.16E−01 |
| L-Serine | 2.94E−01 |
| L-Threonine | 3.52E−01 |
| L-Tryptophan | 3.46E−02 |
| L-Tyrosine 2Na 2H2O | 1.68E−01 |
| L-Valine | 3.55E−01 |
| VITAMINS | |
| Ascorbic acid | 2.53E−01 |
| Biotin | 1.12E−05 |
| B12 | 3.94E−04 |
| Choline chloride | 5.03E−02 |
| D-Calcium pantothenate | 3.69E−03 |
| Folic acid | 4.71E−03 |
| i-Inositol | 5.49E−02 |
| Niacinamide | 1.30E−02 |
| Pyridoxine hydrochloride | 7.62E−03 |
| Riboflavin | 4.56E−04 |
| Thiamine hydrochloride | 2.42E−02 |
| GROWTH FACTORS/PROTEINS | |
| GABA | 9.79E−01 |
| Pipecolic Acid | 9.84E−04 |
| bFGF | 5.77E−06 |
| TGF beta 1 | 2.35E−08 |
| Human Insulin | 3.92E−03 |
| Human Holo-Transferrin | 1.37E−04 |
| Human Serum Albumin | 1.95E−01 |
| Glutathione (reduced) | 6.38E−03 |
| OTHER COMPONENTS | |
| Hypoxanthine Na | 1.18E−02 |
| Phenol red | 1.69E−02 |

TABLE 1-continued

Complete Formulation for TeSR1 Medium

| | mM |
|---|---|
| Putrescine-2HCl | 3.95E−04 |
| Thymidine | 1.18E−03 |
| 2-mercaptoethanol | 9.80E−02 |
| Pluronic F-68 | 2.33E−02 |
| Tween 80 | 3.29E−04 |

Certain components in the above formulation may also be substituted, e.g., in order to facilitate the use of TeSR for research or save money. For example, the medium mTeSR1 may be used instead of TeSR1 and differs from TeSR1 in the following ways: bovine serum albumin (BSA) may be substituted for human serum albumin, and cloned zebrafish basic fibroblast growth factor (zbFGF) may be substituted for bFGF. TeSR1 is described, e.g., in Ludwig et al. (2006), which is incorporated by reference herein in its entirety.

"TeSR-GF" or "mTeSR-GF" refers to a TeSR media which lacks bFGF and TGF-β. "EB basal media" refers to a media containing: IMDM supplemented with about 20% BIT9500 (Stem Cell Technologies) or Serum Replacement 3 (Sigma-Aldri ch, St. Louis, Mo.), about 1% NEAA, about 1 mM L-glutamine, about 0.1 mM mercaptoethanol, about 0.75% BSA, and about 50 ug/ml ascorbic acid. The term "TeSR medium," as used herein, encompasses TeSR1 medium, TeSR2 medium, or mTeSR medium. TeSR2 medium is essentially identical to TeSR1 medium, with the exception that TeSR2 medium is humanized. TeSR1 medium, TeSR2 medium, or mTeSR medium may be used in the methods disclosed herein.

1. Preconditioning in a Defined Media with Reduced Growth Factor Content

After culture and/or maintenance of a pluripotent cell culture (e.g., in a two-dimensional culture system comprising a TeSR media and a matrix component such as Matrigel™ or fibronectin), and prior to hematopoietic differentiation, pluripotent cells may be advantageously exposed to or cultured in a defined media with reduced, essentially eliminated, or lacking growth factors, and in certain embodiments the media may be supplemented with TGF-13 and/or FGF-2. For example, a TeSR media with substantially reduced levels of growth factors (e.g., supplemented with about 0.1 ng/mL TGF-β and about 20 ng/mL FGF-2, but lacking all other non-insulin growth factors) may be used to culture or "precondition" cells prior to exposure to additional growth factors, e.g., to promote differentiation into hematopoietic cells.

This "preconditioning" culture step may comprise culturing pluripotent cells for a period of from about 12 hours to about 7 days or more. In certain embodiments, the preconditioning step may comprise culturing cells for from about 1 to about 7 days, from about 1 to about 3 days, or about 1, 2, 3, 4, 5, 6, or 7 days or any range derivable therein. As shown in the below examples, a preconditioning culture of from about 1 to about 3 days can be sufficient to significantly improve the subsequent hematopoietic differentiation of pluripotent cells.

The defined media used in a preconditioning culture may comprise FGF-2 and/or TGF-β. Typically, the amounts of FGF-2 and/or TGF-β supplemented in the preconditioning culture may be reduced as compared to the defined media used to maintain the cells in an essentially undifferentiated state. In certain embodiments, from about 10 pg/mL to about 5 ng/mL, or from about 0.05 ng/mL to about 0.5 ng/mL, or any range derivable therein, of TGF-β may be included in a defined media during a preconditioning culture. In various embodiments, from about 1 ng/mL to about 100 ng/mL, about 5 ng/mL to about 50 ng/mL, or about 10 ng/mL to about 25 ng/mL, or about 20 ng/mL of FGF-2 may be included in a defined media during a preconditioning culture. The FGF-2 may be a recombinantly produced human or zebrafish FGF-2.

B. Matrix Component

A matrix component may be advantageously included in a defined media for culturing and maintaining pluripotent cells in a substantially or essentially undifferentiated state. When cultured in a suitable semi-solid matrix, individual progenitors called colony-forming cells (CFCs) can proliferate to form discrete cell clusters or colonies. CFC assays may be performed by placing a cell suspension into a semi-solid medium, such as methylcellulose or collagen supplemented with nutrients and cytokines, followed by incubation, e.g., at about 37° C.

Various matrix components may be used to culture and maintain pluripotent cells, such as hESC or iPSC. For example, collagen IV, fibronectin, laminin, and vitronectin in combination may be used to provide a solid support for embryonic cell culturing and maintenance, as described in Ludwig et al. (2006), which is incorporated by reference in its entirety.

Matrigel™ may also be used to provide a substrate for cell culture and maintenance of pluripotent cells. Matrigel™ is a gelatinous protein mixture secreted by mouse tumor cells and is commercially available from BD Biosciences (New Jersey, USA). The mixture resembles the complex extracellular environment found in many tissues and is used by cell biologists as a substrate for cell culture. Methods for human embryonic stem cell culture and maintenance in defined media with Matrigel™ are described, e.g., in Ludwig et al. (2006), and may be used to culture pluripotent cells prior to hematopoietic differentiation. It is appreciated that additional methods for the culture and maintenance of human embryonic stem cells, as would be known to one of skill, may be used with the present invention.

II. Seeding and Differentiation of ES Cells

Pluripotent cells may be partially, essentially, or completely dissociated or individualized prior to hematopoietic differentiation. Pluripotent cells may be seeded as a single colony or clonal group, as clumps of cells dissociated from cultured tissues, or as individualized cells to promote hematopoietic differentiation. Pluripotent cells may be individualized or separated into essentially individual cells using mechanical or enzymatic methods, such as exposure of the tissue comprising pluripotent cells to trypsin or TrypLE™. A proteolytic enzyme may be used to dissociate cells from a culturing surface, and to separate the cells themselves. Enzymes which may be used to individualize ES cells for differentiation include serine proteases such as trypsin, as well as mixtures of enzymes such as those found in Accutase™.

Pluripotent cells may be added or seeded as essentially individual (or dispersed) cells to a seeding media. In certain embodiments, dispersed ES cells are seeded into a seeding media at a density of about 0.5-3 million cells per ml on a surface, such as a low attachment surface. In certain embodiments, the seeding media is a defined media. It is anticipated that essentially any material which is compatible with standard aseptic cell culture may be used culturing surface, although in certain embodiments low attachment surfaces may be advantageously used. The seeding media may comprise TeSR media or mTeSR media, a matrix component, and a ROCK inhibitor.

Pluripotent cells may be cultured in or exposed to seeding medium with or without a ROCK inhibitor, a protease inhibitor (e.g., a trypsin inhibitor), and/or a PKC inhibitor, and the cells may be cultured under a hypoxic atmosphere in a defined culture media comprising one or more growth factors. In certain embodiments, Soybean trypsin inhibitor (e.g., about 0.25 mg/mL-0.5 mg/ml) may be included in a seeding media. The seeding media and the defined culture media may each be free or essentially free of feeder cells. Further differentiated cells may be subsequently harvested. For example, hematopoietic precursor cells or CD34+ cells may result at about 8 days to about 12 days or more, or at from about 6 days to about 9 days, of culturing after seeding.

Optionally, poly vinyl alcohol (PVA) may be included in media comprising a ROCK inhibitor during the formation of embryoid bodies (EBs). The inventor has observed that, while PVA is not required for formation of EBs in a media comprising a ROCK inhibitor, PVA can nonetheless be included in a media (e.g., a TeSR media lacking growth other than reduced levels of TGF-β and FGF-2) during EB formation. TrypLE™, or other enzymatic digestion, may be used to substantially individualize or break apart the pluripotent cells prior to exposure to a ROCK inhibitor and/or a trypsin inhibitor (and/or, optionally, PVA) and EB formation.

III. Differentiation of Pluripotent Cells into Hematopoietic Precursor Cells

After partially, essentially, or completely dissociating or individualizing pluripotent cells, the cells may be further cultured in a defined media to promote hematopoietic differentiation. It has been discovered that specific combinations of growth factors can substantially promote differentiation of the pluripotent cells into hematopoietic precursors and hematopoietic cell lineages. It has further been discovered that the sequential application of specific combinations of growth factors may be used to further promote differentiation of pluripotent cells. In certain embodiments, specific combinations of growth factors are critical for the hematopoietic differentiation of pluripotent cells. For example, it is shown herein that combinations of BMP4, VEGF, Flt3 ligand, IL-3, and GMCSF may be used to promote hematopoietic differentiation. In certain embodiments, the inventor has discovered that the sequential exposure of cell cultures to a first media that includes BMP4 and VEGF (and optionally FGF-2), followed by culture in a second media that includes Flt3 ligand, IL-3, and GMCSF can surprisingly increase the differentiation of pluripotent cells into hematopoietic precursor cells and hematopoietic cells. For example, as shown in the below examples, this sequential exposure resulted in approximately a doubling in the number of hematopoietic precursor cells produced over the same time period under defined conditions. Further, inclusion of FGF-2 (50 ng/ml) in the media containing BMP4 and VEGF resulted in at least a doubling of the efficiency of the generation of hematopoietic precursor cells from pluripotent cells.

Differentiation of pluripotent cells into hematopoietic precursor cells may be performed using defined or undefined conditions. Generally, it will be appreciated that defined conditions are generally preferable in embodiments where the resulting cells are intended to be administered to a human subject. Hematopoietic stem cells may be cultured from pluripotent stem cells under defined conditions (e.g., using a TeSR media and a matrix component such as Matrigel™), and hematopoietic cells may be generated from embryoid bodies derived from the from pluripotent cells. In other embodiments, pluripotent cells may be co-cultured on OP9 cells or mouse embryonic fibroblast cells and subsequently differentiated.

Pluripotent cells may be allowed to form embryoid bodies as a part of the differentiation process. The formation of "embryoid bodies" (EBs), or clusters of growing cells, in order to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins. Three-dimensional EBs can thus be used to produce some fraction of hematopoietic cells and endothelial cells.

EBs may be formed using the following protocol. Undifferentiated hESC or iPSC adapted to feeder free growth on Matrigel™ coated plates may be harvested at confluence using collagenase IV (1 mg/ml) treatment for about 10 minutes at about 37 C. The wells may be washed free of collagenase after the incubation and the EBs may be formed by scraping the wells in EB basal media. The media may be changed the next day to EB differentiation media containing different cytokine formulations.

To promote EB formation, the cells may be transferred to a low-attachment plates for an overnight incubation in "EB basal media" containing IMDM supplemented with about 20% BIT9500 (Stem Cell Technologies) or Serum Replacement 3, about 1% NEAA, about 1 mM L-glutamine, and about 0.1 mM mercaptoethanol, about 0.75% BSA, and about 50 ug/ml ascorbic acid. The next day the cells may be collected from each well and centrifuged. The cells may then be resuspended in "EB differentiation media," which consists of EB basal media supplemented with about 50 ng/ml bone morphogenetic factor (BMP-4), about 50 ng/ml vascular endothelial growth factor (VEGF), about 25 ng/ml stem cell factor (SCF), about 25 ng/ml Flt-3 ligand (Flt-3L), about 10 ng/ml interleukin-3 (IL-3), about 10 ng/ml interleukin-6 (IL-6), about 20 ng/ml granulocyte colony-stimulating factor (G-CSF) about 20 ng/ml granulocyte macrophage colony-stimulating factor (GM-CSF), about 0.2 U/ml erythropoietin (EPO), about 25 ng/ml thrombopoieitin (TPO), and about 25 ng/ml FGF-2. The media may be changed every four days by transferring the EB's into a 15-mL tube and letting the aggregates settle for about 5 minutes. In certain embodiments, the EB differentiation media may include about BMP4 (e.g., about 50 ng/ml), VEGF (e.g., about 50 ng/ml), and optionally FGF-2 (e.g., about 25-75 ng/ml or about 50 ng/ml). The supernatant may be aspirated and replaced with fresh differentiation medium. Alternately the cells may be half fed every two days with fresh media. The cells may be harvested at different time points during the differentiation process.

Hematopoietic precursor cells may be cultured from pluripotent stem cells using a defined medium. Methods for the differentiation of pluripotent cells into hematopoietic CD34+ stem cells using a defined media are described, e.g., in U.S. Application 61/015,813, which is incorporated by reference in its entirety without disclaimer. It is anticipated that these methods may be used with the present invention.

For example, a defined medium may be used to induce hematopoietic CD34+ differentiation. The defined medium may contain the growth factors BMP-4, VEGF, Flt3 ligand, IL-3 and/or GMCSF. Pluripotent cells may be cultured in a first defined media comprising BMP4, VEGF, and optionally FGF-2, followed by culture in a second media comprising either (Flt3 ligand, IL-3, and GMCSF) or (Flt3 ligand, IL-3, IL-6, and TPO). The first and second media may also comprise one or more of SCF, IL-6, G-CSF, EPO, FGF-2, and/or TPO. Substantially hypoxic conditions (e.g., less that 20% O2) may further promote hematopoietic or endothelial differentiation.

Cells may be substantially individualized via mechanical or enzymatic means (e.g., using a trypsin or TrypLE™). A ROCK inhibitor (e.g., H1152 or Y-27632) may also be included in the media. It is anticipated that these approaches may be automated using, e.g., robotic automation.

Although the use of defined methods for the differentiation of pluripotent cells into hematopoietic precursor cells may be preferred in certain instances, undefined approaches may nonetheless be used in various embodiments. One undefined method for the differentiation of hematopoietic stem cells from human ESCs involves culturing the ESCs on feeder cells, such as a mouse embryonic fibroblast (MEF) feeder layer or the mouse stromal cell line OP9, which induces robust differentiation to CD34+. Briefly, ESCs may be grown on MEFs in the presence of growth factors, and the MEFs provide a substrate and likely some nourishment for the cells. In contrast to defined conditions, use of OP9 cells generally does not require extra growth factors to induce CD34+ differentiation. The mechanisms by which these processes occur are not fully understood. This approach may also be used in combination with certain growth factors and serum (Wang, 2007). MEFs are also often used for culturing and maintaining human ESCs. Methods that utilize culture on mouse embryonic fibroblasts, such as the below protocol, may be modified to include Knockout™ serum replacement instead of FBS.

The following undefined protocol may be used for differentiation of pluripotent cells into hematopoietic cells. H1 cells may be routinely maintained on MEFs, and then passed onto almost confluent OP9 stromal cells in aMEM+20% defined FBS+100 ng/ml TPO at $1\times10^5$ cells/well (1 well is 9.6 $cm^2$). Cells may be fed with fresh medium at days 2 and 4. On day 7, cells may be split 1:3 onto fresh OP9 cells using collagenase IV. Cells may be fed with fresh medium at days 8 and 10. On day 11, cells may be split 1:1 onto fresh OP9 cells using collagenase IV, followed by Trypsin/EDTA to get single cells, and the medium may be changed to αMEM+10% defined FBS+100 ng/ml TPO. Cells may be fed by adding an additional 1 ml of this medium daily from days 14-16. In certain embodiments, methods for differentiation involving OP9 cells may be performed as described in Gaur et al., 2006, which is specifically incorporated by reference in its entirety.

IV. Differentiation of Hematopoietic Precursor Cells into Myeloid or Lymphoid Lineages Various approaches may be used with the present invention to further differentiate hematopoietic precursor stem cells into cell lineages including erythrocyte, granulocyte, macrophage, and megakaryocyte. These approaches may include the use of erythroid differentiation medium, methylcellulose, and megakaryocyte differentiation medium. In certain embodiments, hematopoietic progenitor cells may also be differentiated into endothelial cells or used to produce blood vessels.

These cell lineages may be used in a variety of medical treatments and applications. For example, erythrocyte lineages may be used in the production of blood for blood transplants. In other embodiments, endothelial cells may be used to produce new blood vessels that may be used to treat a regional ischemia. Alternately, in certain embodiments, hematopoietic cells differentiated according to the invention may be administered to treat a disease such as sickle cell anemia (Hanna et al., 2007).

In vitro assay systems have been developed to quantify multi-potential progenitors and lineage-restricted progenitors of the erythrocyte, granulocyte, monocyte-macrophage, and megakaryocyte myeloid cell lineages. The colony-forming cells (CFCs) may be classified and enumerated based on the morphological recognition of one or more types of hematopoietic lineage cells within the colony. Colony evaluation and enumeration can be done in situ by light microscopy or by plucking individual colonies and then staining the cells using cytochemical and immunocytochemical methods. Various gelling agents including agar, agarose, methylcellulose, collagen and fibrin clots have been used for CFC assays.

A. Erythroid Differentiation

Hematopoietic progenitor cells may be differentiated into erythroid cells using, e.g., an erythroid differentiation medium. An erythroid differentiation medium may a serum-free or defined medium, and the medium may contain SCF, EPO, TPO, insulin, dexamethasone or hydrocortisone, and transferrin (Slukvin et al., 2007).

The following protocol may be used to differentiate hematopoietic precursor cells into erythroid cells. Erythroid progenitors may be generated by placing the hematopoietic precursor cells derived from IL-3, FLT-3, SCF, and TPO in media containing hydrocortisone (10-6M), holotransferrin, and EXCYTE. As shown in the below examples, one million hESCs were capable of generating 2 million erythroid progenitors.

B. Methylcellulose

Methylcellulose may be used to induce differentiation of erythrocytes, macrophages and/or granulocytes from hematopoietic progenitor cells. Methylcellulose is a relatively inert polymer that forms a stable gel with good optical clarity. It is commonly used at a final concentration of 0.9-1.2% in culture medium supplemented with compounds including fetal bovine serum (FBS), bovine serum albumin (BSA), 2-mercaptoethanol, insulin, transferrin and recombinant cytokines or conditioned medium as a source of colony-stimulating factors. Methods involving methylcellulose differentiation of cells are described, e.g., in Kaufman et al. (2001).

Methylcellulose-based medium permits better growth of erythroid lineage cells than other types of semi-solid matrices, thus allowing the assay of erythroid, granulocyte, monocyte and multi-potential CFCs within the same culture. Megakaryocyte progenitors are suitably cultured in supplemented collagen-based medium and specifically identified using immunocytochemical staining.

C. Megakaryocyte Differentiation

Hematopoietic precursor cells may be further differentiated into megakaryocytes. In the body, megakaryocytes are found in the blood marrow and produce platelets from processes, or proplatelets, which form on the cells. Megakaryocyte cells in the human body only represent a small fraction of bone marrow cells but can increase in number up to 10-fold in response to certain diseases. In the body, megakaryocytes typically differentiate from hematopoietic cells as follows: hemacytoclasts differentiate into megakaryoblasts, megakaryoblasts then differentiate into promegakaryocytes, and promegakaryocytes then differentiate into megakaryocytes.

Various media and methods may be used to differentiate pluripotent cells or hematopoietic precursor cells into megakaryocytes. For example, methods and media for differentiating pluripotent cells into megakaryocytes as described in US 2007/0077654, which is incorporated by reference in its entirety without disclaimer, may be used with the present invention.

Growth factors are preferentially included in a megakaryocyte differentiation medium. For example, a megakaryocyte differentiation medium may contain one, two, three, four, or all of FLT-3 ligand, stem cell factor (SCF), thrombopoietin (TPO), interleukin-3 (IL-3), and interleukin-6 (IL-6). In certain embodiments, only SCF may be included in a megakaryocyte differentiation medium. In other embodiments, SCF may be used in combination with one or both of IL-3 and/or IL-6. In various embodiments, FLT-3 ligand and/or TPO may be excluded from a megakaryocyte differentiation medium of the present invention.

Hematopoietic cells may be differentiated into megakaryocytes via the following protocol. Megakaryocytes may be produced by placing the hematopoietic precursor cells in media-containing (100 ng/ml TPO, SCF, FLT-3, 20% BIT9500). As shown in the below examples, one million hESCs were capable of generating 0.06 million megakaryocytes.

A megakarocyte differentiation medium may be used to induce generation of megakarocytes. Various products and approaches for the generation of megakarocytes have been described and may be used with the present invention, such as described in WO2006/050330. Additionally, Megacult™ is available from Stem Cell Technologies and may be used for producing/differentiating megakaryocytes. In various embodiments, thrombopoeitin (TPO), interleukin 3 (IL-3), interleukin 6 (IL-6) and/or stem cell factor may be included in a megakarocyte differentiation medium. Methods for megakarocyte differentiation of cells are described, e.g., in Kaufman et al. (2001).

D. Endothelial Cell Differentiation

Hematopoietic cells may also be differentiated into endothelial cells. Endothelial cells may be generated, for example, using the following protocol for implantation into an animal or human subject. Human ES cell-derived CD31+ cells may be cultured in either EGM™-2 medium (Lonza, Switzerland) or differentiation medium with 50 ng/mL rhVEGF and 5 ng/mL rhFGF-2 for 7 to 10 days.

For further expansion and differentiation of endothelial cells, isolated CD31+ cells may be cultured in endothelial differentiation medium (Lonza catlalog #CC3202) containing VEGF, FGF, EGF, IGF, ascorbic acid and FBS or differentiation medium containing 50 ng/ml, vasular endothelial growth factor (VEGF), and FGF-2 (e.g., 50 ng/ml zebrafish FGF-2). Cells may be cultured for 2 to 3 weeks.

The following protocol may be used to induce endothelial differentiation. For expansion and differentiation of endothelial cells, isolated CD34+ cells may be seeded on gelatin-coated wells (1.5 to $2 \times 10^4$ cells/cm$^2$) in EGM-2MV medium (Cambrex). Collagen I-coated wells (BD labware) may also be used, although gelatin is typically less expensive than collagen I-coated wells. CD34+ cells may be cultured in hESC differentiation medium containing the endothelial growth factors, hVEGF$_{165}$ (50 ng/mL) and FGF-2 (5 ng/mL). After about 7-10 days of incubation, the adherent cells may be harvested by trypsin-treatment and used for analyses.

Endothelial cells may be evaluated by imaging a Matrigel plug. For example, the following protocol may be used to image cells: endothelial cells (ECs) derived from hESCs or iPSCs may be suspended in Matrigel (e.g., about 1 million cells in 1 ml) and injected subcutaneously into SCID Beige mice. FITC Dextran can then be injected intravenously at about day 14 before the removal of the matrigel plug. The plugs may be harvested and subjected to imaging using fluorescence imaging techniques, and the plug may be analyzed for the presence or absence of neovascularization.

E. Mast Cell Generation

Hematopoietic precursor cells may be further differentiated into mast cells. Exposure of pluripotent cells to stem cell factor (SCF), IL-6, IL-3, IL-4, IL-9 and/or IL-10 may promote mast cell differentiation.

In certain embodiments the following protocol may be used to promote differentiation into mast cells. Hematopoietic cells may be first differentiated in to megakaryocytes by placing hematopoietic precursor cells in media "MK3" containing (100 ng/ml TPO, SCF, FLT-3, 20% BIT9500). Mast cells may be subsequently produced by expanding the precursor in MK3 expansion followed by 50 ng/ml SCF, 50 ng/ml IL-6 containing media.

In various embodiments, methods for differentiation of cord blood or peripheral blood into mast cells may also be used to promote megakaryocyte differentiation. For example, Schernthaner et al. (2001) describes methods for differentiating cord blood progenitors into mast cells using SCF in combination with IL-6 or (IL-4, IL-6, and IL-10) at various time points. Lappalainen et al. (2007) provides methods for differentiating peripheral blood into mast cells by culturing cells using SCF and other cytokines (IL-3, IL-6, IL-9, and IL-4) added for various periods of time. It is anticipated that either of these methods may be successfully used with the present invention.

F. Macrophages and Dendritic Cells

Hematopoietic precursor cells may be further differentiated into dendritic cells. For example, hematopoietic precursor cells may be placed for 8 days in media containing 200 ng/ml GMCSF. These cells may then be further differentiated into either macrophages by placing the cells in M-CSF (10 ng/ml) and IL-1β (20 ng/ml) containing media for 2 weeks, or dendritic cells by placing the cells in (20 ng/ml GMCSF, 20 ng/ml IL-4). As shown in the below examples, one million hESCs were capable of generating about 0.2-2.5 million dendritic cells and about 0.5-2.5 million macrophages.

V. Differentiation of Pluripotent Cells into Endothelial Cells

Pluripotent cells, such as iPSC or hESC, may be differentiated into endothelial cells in various embodiments of the present invention. As endothelial cells compose part of blood vessels, these cells may be particularly useful, e.g., for screening or testing a compound to determine the effects, pharmacology, or toxicology of the compound on the blood vessels or endothelial cells. The endothelial cells may also be used for the evaluation or identification with one or more of the following properties: vasoconstriction or vasodilation, control of blood pressure, blood clotting (e.g., thrombosis or fibrinolysis), promoting or reducing atherosclerosis, angiogenesis, inflammation, and/or effects on barrier function (e.g., blood-brain barrier function or transport of compounds. The endothelial cells may also be useful for screening or identifying compounds that may promote or reduce coronary artery disease, diabetes mellitus, hypertension, or hypercholesterolemia.

In certain embodiments, a pluripotent cell may be preconditioned for about 12-36 hours or about 24 hours in a defined media (e.g., a TeSR media) supplemented with TGF (e.g., about 0.1 ng/ml) and FGF (e.g., 20 ng/ml). The cells may then be harvested at confluence, e.g., using TrypLE treatment for about 5 minutes at about 37° C. The cells may be collected in EB basal media (e.g., containing IMDM supplemented with about 20% BIT9500 (Stem Cell Technologies) or Serum Replacement-3™, about 1% NEAA, about 1 mM L-glutamine, about 0.1 mM mercaptoethanol, about 0.75% BSA, about 50 ug/ml ascorbic acid, and a ROCK inhibitor such as 1 μM of H-1152). Cells may then be cultured on a low-attachment culture surface or plate, bioreactor, or spinner flask, etc.

After about 12-24 hours of culture the cells may be collected and resuspended in EB basal media supplemented with BMP-4 (e.g., 50 ng/ml), VEGF (e.g., 50 ng/ml), and FGF-2 (e.g., 50 ng/ml). The media may be at least partially replaced with fresh media on about day four. On about day 7 of EB differentiation, the cells may be placed in an endothelial differentiation medium, such as EGM-2MV, Lonza catlalog #CC3202. In certain embodiments, the endothelial differentiation medium includes at least one, two, three, four, five or all of VEGF, FGF, EGF, IGF, Ascorbic acid and/or FBS. Endothelial cells may subsequently be collected, e.g., on day 10 of culture. One or more cell marker, such as CD31 and/or CD105, may be used to substantially purify a population of endothelial cells from the cell population using, e.g., MACS of FACS. As shown in the below examples, endothelial cells may be successfully generated from iPSC or hESC in certain embodiments of the present invention. Cell markers which may be used to identify or substantially purify endothelial cells include CD31, CD105, CD144 (VE-cadherin), CD106, CD146, and ZO1 (tight junction protein).

VI. Hypdxia and Differentiation

In certain embodiments, substantially hypoxic conditions may be used to promote differentiation of pluripotent cells into hematopoietic progenitor cells. As would be recognized by one of skill in the art, an atmospheric oxygen content of less than about 20.8% would be considered hypoxic. Human cells in culture can grow in atmospheric conditions having reduced oxygen content as compared to ambient air. This relative hypoxia by may be achieved by decreasing the atmospheric oxygen exposed to the culture media. Embryonic cells typically develop in vivo under reduced oxygen conditions, generally between about 1% and about 6% atmospheric oxygen, with carbon dioxide at ambient levels. Without wishing to be bound by theory, it is anticipated that hypoxic conditions may mimic an aspect of certain embryonic developmental conditions. As shown in the below examples, hypoxic conditions can be used in certain embodiments to promote additional differentiation of pluripotent cells, such as iPSC or hESC, into a more differentiated cell type, such as hematopoietic precursor cells.

The following hypoxic conditions may be used to promote differentiation of pluripotent cells into hematopoietic progenitor cells. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

VII. Defined Culture Media

As described herein, one or more defined culture medium may be advantageously used to promote the differentiation of pluripotent cells into hematopoietic precursor cells; in particular, the elimination of animal products such as serum and mouse feeder layers can reduce the risks associated with exposure of cells to animal products and allow for the generation of cells that could be more safely administered to a human subject. As traditional stem cell culture development has relied on serum products and mouse feeder layers for differentiating stem cells into a variety of cell types, these traditional procedures have limited the scale on which differentiation can be conducted, increased biological variability and potential contamination, and severely hampered the use of ES cells in translational therapies in which they might otherwise prove useful.

In particular, the inventor has identified that exposure of pluripotent cells to a defined culture medium comprising a very limited number of cytokines (e.g., BMP4, VEGF, FLT-3, and IL-3, optionally in combination with GMCSF, IL-3. IL-6, TPO and/or FGF-2), which are included in the medium simultaneously or sequentially, can be used to promote differentiation into hematopoietic precursor cells. It has been surprisingly observed that, while BMP-4 alone and VEGF alone in a cell culture media did not promote hematopoietic differentiation, the inclusion of both BMP4 and VEGF in the cell culture medium synergized, and in certain embodiments were necessary, to promote the differentiation of precursor cells into hematopoietic cells. Inclusion of FGF-2 in the defined media with BMP4 and VEGF can promote differentiation of pluripotent cells; for example and as illustrated in the below experiments, inclusion of FGF-2 in this media resulted in at least a doubling in the efficiency of generation of hematopoietic precursor cells (HPCs) from pluripotent cells.

The inventor has further identified that, in certain embodiments, sequentially exposing precursor cells to first the combination of (BMP4, VEGF, and optionally FGF-2), followed by the exposure of the cells to either (FLT-3, IL-3, and GMCSF) or (FLT-3, IL-3, TPO, IL-3, and IL-6) can surprisingly further promote differentiation (e.g., differentiation into hematopoietic precursor cells), as compared to the simultaneous exposure of the cells to all of these cytokines over the same period of time. The cells may be allowed to re-aggregate after exposure to (BMP4 and VEGF) and prior to exposure to (FLT-3 and IL-3) to promote or improve exposure of the cells to the subsequent growth factors. Without wishing to be bound by any theory, it is anticipated that this step of re-aggregation may further promote differentiation of the cells into hematopoietic precursor cells.

Culture media typically contain additional nutrients, amino acids, antibiotics, buffering agents, and the like. In certain embodiments, the defined culture medium contains one or more of the components listed below in Table 1. The below culture medium may include about 25 ng/ml of Flt-3, about 10 ng/ml IL-3 and about 10 ng/ml GMCSF. The media may include one or more antibiotics, although differentiation methods may be performed on cells in the absence of antibiotics. As illustrated in the below examples, inclusion of Serum Replacement 3 in the IMDM culture media can further promote differentiation of pluripotent cells, and increases.

TABLE 2

IMDM Defined Culture Medium

20% BIT 9500 or Serum Replacement 3
25-50 ng/mL BMP4
25-50 ng/mL VEGF
5-25 ng/ml FGF2
2 mM L-glutamine
0.1 mM Non essential amino acids
450 µM Monothioglycerol
50 µg/ml Ascorbic acid
0.75% BSA A. Growth Factors Various growth factors may be used to promote the differentiation of pluripotent cells into hematopoietic precursor cells. In certain embodiments, a defined culture medium of the present invention may contain one, two, or more growth factors such as, for example, (BMP-4 and VEGF) or (BMP-4, VEGF, FLT-3, IL-3, and GMCSF).

Growth factors which may be comprised in a defined culture medium of the present invention include, but are not limited to, BMP-4, VEGF, bFGF, stem cell factor (SCF), Flt3 ligand, interleukin 3 (IL-3), interleukin 6 (IL-6), interleukin 9 (IL-9), interleukin 11 (IL-11), insulin related growth factor 1 (IGF1), insulin related growth factor 2 (IGF2), erythropoietin (EPO), thrombopoietin (TPO), granulocyte-macrophage-colony-stimulating factor (GMCSF or GM-CSF), and granulocyte colony-stimulating factor (GCSF or G-CSF). A defined culture medium of the present invention may contain one, two, three, or more of these factors; for example, other growth factors may be included in a defined medium in order to increase proliferation or modulate the differentiation state of the cells. In certain embodiments, a defined media may contain at least (BMP-4 and VEGF, and optionally FGF-2) or (FLT-3, IL-3, and GMCSF); in these embodiments, while not necessary, one or more additional growth factor may be included in the defined media. For example, GMCSF can be substituted using TPO or SCF at about 25 ng/ml in the second step of the differentiation process. Various amounts of these factors may be used to stimulate cellular responses (e.g., in the amounts described in Yamamura et al., 2008; Fadilah et al., 2007; Bashey et al., 2007). For example, about 1-50 ng/mL, about 5-25 ng/mL, or about 10 ng/mL of TPO may be included to promote cell expansion or differentiation of cells. In various embodiments, SCF may be included in a defined media at a concentration of from about 5-100 ng/mL, about 10-50 ng/mL, or about 25 ng/mL. In various embodiments, IL-6 may be included in a defined media at a concentration of from about 5-50 ng/mL, about 5-25 ng/mL, or about 10 ng/mL. Granulocyte colony stimulating factor (G-CSF) may be used for generating granulocytes from hematopoietic precursor cells.

1. BMP-4

Bone morphogenetic protein-4 (BMP-4) is a member of the group of bone morphogenic proteins and a ventral mesoderm inducer. BMPs are expressed in adult human bone marrow (BM) and are important for bone remodeling and growth. In certain embodiments, inclusion of BMP4 is only needed for the first two to three days in culture, after which time it can be removed from the system with no detrimental effect on differentiation.

BMP-4 is important for the modulation of the proliferative and differentiative potential of hematopoietic progenitor cells (Bhardwaj et al., 2001; Bhatia et al., 1999; Chadwick 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). For example, BMP-4 can regulate the proliferation and differentiation of highly purified primitive human hematopoietic cells from adult and neonatal sources (Bhatia et al., 1999), and BMP-4 can promote hematopoietic differentiation in human embryonic stem cells (Chadwick, 2003).

BMP-4 may be included in a defined culture medium at a concentration of about 5-100 ng/mL, about 20-100 ng/mL, about 20-50 ng/mL, about 10-30 ng/mL, about 15-30 ng/mL, about 20-30 ng/mL, or any range derivable therein. In certain embodiments, BMP-4 is included in the defined culture media at a concentration of about 5, 10, 15, 20, 25, 30, 35, 40, 45, or about 50 ng/mL.

2. VEGF

Vascular endothelial growth factor (VEGF) is an important signaling protein which is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function has also been shown to be important in a variety of disease states including cancer, diabetes, autoimmune diseases, and ocular vascular diseases.

VEGF may be included in a defined culture medium at a concentration of from about 10-100 ng/mL, about 20-100 ng/mL, about 10-50 ng/mL, about 15-30 ng/mL, about 20-30 ng/mL, about 20-50 ng/mL, or any range derivable therein. In certain embodiments, VEGF is included in the defined culture media at a concentration of about 2.5, 5, 10, 15, 20, 25, 30, 35, 40, 45, or about 50 ng/mL.

3. FGF-2

Basic fibroblast growth factor, also referred to as bFGF or FGF-2, is a growth factor which has been implicated in diverse biological processes, including limb and nervous system development, wound healing, and tumor growth. Previous studies have indicated that bFGF is unlikely to affect hematopoietic cell development or survival (Ratajczak et al., 1996.), although bFGF has been used to support feeder-independent growth of human embryonic stem cells (Ludwig et al., (2006). In certain embodiments, bFGF is not required to induce differentiation; thus, in various embodiments it may be included or excluded in a medium of the present invention.

bFGF may be included in a defined culture medium at a concentration of from about 5 to about 100 ng/mL, 5 to about 50 ng/mL, from about 5 to about 25 ng/mL, from about 25 to about 50 ng/mL, or any range derivable therein. In certain embodiments, bFGF is included in the defined culture media at a concentration of about 2.5, 5, 10, 15, 20, 25, 30, 35, 40, 45, 50, 55, 60, 65, 70, or about 75 ng/mL. These concentrations may be particularly useful for media used for the maintenance of pluripotent cells in an undifferentiated or substantially undifferentiated state. In various embodiments, FG2 (e.g., at about 100 ng/ml) may be used for maintenance of pluripotency of cells. To promote hematopoietic differentiation, cells may be exposed to FGF2 at a concentration between about 5-50 ng/ml.

It has been discovered by the inventor that, in various embodiments, lower concentrations of bFGF may be included in a defined media in a "preconditioning" culture phase prior to hematopoietic differentiation. For example, from about 5 ng/mL to about 50 ng/mL, from about 10 ng/mL to about 30 ng/mL, from about 15 ng/mL to about 25 ng/mL, less than about 50 ng/mL, less than about 40 ng/mL, less than about 30 ng/mL, or about 10, 15, 20, 25, or 30 ng/mL bFGF may be included in a defined media in a preconditioning culture of pluripotent cells prior to differentiation of the cells into hematopoietic precursor cells. In certain embodiments, a TeSR media without growth factors which has been supplemented with bFGF (e.g., about 25-75 ng/mL or about 50 ng/ml) or FGF-2 and 0.1 ng/mL TGF-β may be used in a preconditioning culture of pluripotent cells prior to hematopoietic differentiation. In certain embodiments, this preconditioning step can be essential to promote subsequent hematopoietic differentiation.

After pluripotent cells have been preconditioned (e.g., in a TeSR media without growth factors supplemented with TGF-β and FGF-2 for about 1 day), cells may then be placed in an EB differentiation media comprising BMP4, VEGF, and FGF-2 (e.g., at about 25-50 ng/ml). As shown in the below examples, the inclusion of FGF-2 can result in at least a doubling in the efficiency for differentiation of pluripotent cells, such as hESC or iPSC, into hematopoietic precursor cells.

It is envisioned that, in certain embodiments, other fibroblast growth factors such as acidic FGF (aFGF), FGF4, FGF9, FGF17 or FGF18 may substituted for or included with bFGF, e.g., at the concentrations described above. Alternately, an FGF-2 mimicking compounds may be substituted for FGF-2 to produce substantially or essentially the same effect. FGF-2 mimics include FGF-2 mimicking peptides, antibodies, and small molecules. For example, synthetic peptide F2A4-K-NS mimics the effects of FGF-2 in vitro and in vivo (Lin et al., 2006) and may be substituted for FGF-2 in various embodiments of the present invention.

FG loop (FGL) peptide is another example of a FGF-2 mimetic which may be used in certain embodiments of the present invention. FGL is a 15 amino acid sequence in the second F3 module of NCAM that represents a part of the binding site of NCAM to the FGFR1. FGL has been shown to bind to and activate FGFR1 and to stimulate neurite outgrowth (Kiselyov et al., 2003).

The BioSET F2A peptide may also be substituted for FGF-2. The BioSET F2A peptide is a synthetic mimetic of the natural human FGF-2 growth factor. The BioSET F2A peptide and the F2A4-KNS peptide are available from FYI Tornier, Inc., or BioSurface Engineering Technologies, Inc. ("BioSET"). It is envisioned that combinations of FGF-2 mimicking compounds may also be substituted for FGF-2 in various embodiments of the present invention.

4. IL-3

Interleukin-3 (IL-3) is a hematopoietic growth factor involved in the survival, proliferation and differentiation of multipotent hematopoietic cells. In five mammalian species, including man, the gene encoding IL-3 has been isolated and expressed to yield the mature recombinant proteins. The human IL-3 gene encodes a protein of 133 amino acids with two conserved cysteine residues and 2 potential N-linked glycosylation sites (Wagemaker et al., 1990).

In certain embodiments, IL-3 is included in a culture medium of the present invention at a concentration of from 2.5 to about 50 ng/mL, 2.5 to about 50 ng/mL, from about 5 to about 50 ng/mL, from about 5 to about 25 ng/mL, from about 5 to about 15 ng/mL, or any range derivable therein. In certain embodiments, IL-3 is included in the defined culture media at a concentration of about 2.5, 5, 10, 15, 20, 25, or about 30 ng/mL. As shown in the below examples, Flt3 ligand and IL-3 can exert a synergistic action on differentiation of pluripotent cells into hematopoietic precursor cells. In certain embodiments, inclusion of IL-3 is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

5. FLT3 Ligand

Flt3 ligand, also referred to as FLT-3 ligand, is the endogenous ligand for FLT3. FLT3 is a receptor tyrosine kinase expressed by immature hematopoietic progenitor cells. The ligand for FLT3 is a transmembrane or soluble protein and is expressed by a variety of cells including hematopoietic and marrow stromal cells; in combination with other growth factors, Flt3 ligand can stimulate the proliferation and development of stem cells, myeloid and lymphoid progenitor cells, dendritic cells and natural killer cells. Activation of the receptor leads to tyrosine phosphorylation of various key adaptor proteins known to be involved in different signal transduction pathways that control proliferation, survival and other processes in hematopoietic cells. FLT3 and mutations affecting FLT3 are also important in pathological diseases, such as the prognosis and therapy of leukemia (Drexler et al., 2004).

In certain embodiments, Flt3 ligand is included in a culture medium of the present invention at a concentration of from 5 to about 100 ng/mL, 5 to about 50 ng/mL, from about 10 to about 30 ng/mL, from about 15 to about 30 ng/mL, from about 20 to about 30 ng/mL, or any range derivable therein. In certain embodiments, Flt3 ligand is included in the defined culture media at a concentration of about 2.5, 5, 10, 15, 20, 25, 30, 35, 40, 45, or about 50 ng/mL. In certain embodiments, Flt3 ligand is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

6. Granulocyte-Macrophage Colony-Stimulating Factor

Granulocyte-macrophage colony-stimulating factor, also abbreviated as GM-CSF or GMCSF, is a protein secreted by macrophages, T cells, mast cells, endothelial cells and fibroblasts. GMCSF is a cytokine that can function as a white blood cell growth factor, and GMCSF can stimulate stem cells to produce granulocytes (neutrophils, eosinophils, and basophils) and monocytes. Monocytes can exit the circulation and mature into macrophages. Thus, GMCSF can play a role in the immune/inflammatory cascade, by which activation of a small number of macrophages can rapidly lead to an increase in their numbers, a process crucial for fighting infection. The active form of GMCSF is typically found in vivo extracellularly as a homodimer. GMCSF is also referred to as molgramostim or sargramostim (Leukine) when expressed in yeast cells. In certain embodiments, recombinantly produced growth factors may be used to promote hematopoietic differentiation of pluripotent cells.

In certain embodiments, GMCSF is included in a culture medium of the present invention at a concentration of from about 2.5 to about 100 ng/mL, 2.5 to about 50 ng/mL, from about 5 to about 50 ng/mL, from about 5 to about 25 ng/mL, from about 5 to about 15 ng/mL, or any range derivable therein. In certain embodiments, GMCSF is included in the defined culture media at a concentration of about 2.5, 5, 10, 15, 20, 25, or about 30 ng/ml. In certain embodiments, inclusion of GMCSF ligand is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

7. Stem Cell Factor

Stem cell factor (SCF) is a cytokine which binds CD117 (c-Kit). SCF is also known as "KIT ligand," "c-kit ligand," or "steel factor." SCF exists in two forms: cell surface bound SCF and soluble (or free) SCF. Soluble SCF is typically produced in vivo by the cleavage of surface bound SCF by metalloproteases. SCF can be important for the survival, proliferation, and differentiation of hematopoietic stem cells and other hematopoietic progenitor cells. In vivo, SCF can change the BFU-E (burst-forming unit-erythroid) cells, which are the earliest erythrocyte precursors in the erythrocytic series, into the CFU-E (colony-forming unit-erythroid).

In certain embodiments, SCF is included in a culture medium of the present invention at a concentration of from about 5 to about 100 ng/mL, 5 to about 50 ng/mL, from about 10 to about 30 ng/mL, from about 15 to about 30 ng/mL, from about 20 to about 30 ng/mL, or any range derivable therein. In certain embodiments, SCF is included in the defined culture media at a concentration of about 2.5, 5, 10, 15, 20, 25, 30, 35, 40, 45, or about 50 ng/mL.

8. IL-6

Interleukin-6 (IL-6) is a pro-inflammatory cytokine In vivo, IL-6 is secreted by T-cells and macrophages and stimulates immune responses to trauma or other tissue damage leading to inflammation. IL-6 can also play a role in responses to certain bacterium, and osteoblasts secrete IL-6 in vivo to stimulate osteoclast formation. In humans, smooth muscle cells in the tunica media of many blood vessels can produce IL-6 as a pro-inflammatory cytokine, and IL-6 is an important in vivo mediator of fever.

In certain embodiments, IL-6 is included in a culture medium of the present invention at a concentration of from about 2.5 to about 100 ng/mL, 2.5 to about 50 ng/mL, from about 5 to about 50 ng/mL, from about 5 to about 25 ng/mL, from about 5 to about 15 ng/mL, or any range derivable therein. In certain embodiments, IL-6 is included in the defined culture media at a concentration of about 2.5, 5, 10, 15, 20, 25, or about 30 ng/mL.

9. TPO

Thrombopoietin, or TPO, is a glycoprotein hormone which is primarily produced in vivo by the liver and kidney and is involved in the in vivo generation of platelets in the bone marrow. In certain embodiments, TPO is included in a culture medium of the present invention at a concentration of from about 2.5 to about 100 ng/mL, 5 to about 75 ng/mL, from about 10 to about 50 ng/mL, from about 15 to about 35 ng/mL, at about 25 ng/ml, or any range derivable therein. In certain embodiments, TPO is included in the defined culture media at a concentration of about 2.5, 5, 10, 15, 20, 25, 30, 35, 40, 45 or about 50 ng/mL.

B. Matrix Component

A culture media may contain one or more matrix components, such as fibronectin or a RGD peptide. Without wishing to be bound by any theory, a matrix component may provide a solid support for the growth of embryonic stem cells. In certain embodiments, a matrix component may be applied to a culturing surface and contacted with culture media prior to seeding cells into the media. For example, cells may be cultured in a defined media (e.g., a TeSR media) on plates coated with fibronectin or Matrigel™ prior to mechanically separating the cells into clumps or individualizing cells and inducing differentiation into hematopoietic precursor cells.

Various matrix components may be used to culture pluripotent cells including a collagen (e.g., collagen IV), laminin, vitronectin, Matrigel™, gelatin, polylysine, thrombospondin (e.g., TSP-1, -2, -3, -4 and/or -5), and/or ProNectin-F™. In certain embodiments, the use of only Matrigel™, collagen IV, or laminin with cells previously cultured using TeSR may be avoided due to possible adverse effects on cell viability; nonetheless, these compositions may be advantageously used in combination with other matrix components. Combinations of these matrix components may provide additional benefit for promoting cell growth and cell viability. In certain embodiments, 1, 2, 3, 4, 5, 6, or more of the above matrix components may be used to culture cells, e.g., prior to hematopoietic differentiation.

1. RGD Peptides

RGD peptides may be used as a matrix component in a defined cell culture medium. RGD peptides are adhesive proteins which contain the Arg-Gly-Asp(RGD) sequence, and certain RGD peptides may play an important role in cell adhesion, migration and growth. Without wishing to be bound by any theory, RGD peptides may provide a physical substrate for embryonic stem cells, similar to fibronectin, to allow for the differentiation and growth of embryonic stem cells. In certain embodiments, synthetic RGD peptides may be utilized with the present invention.

RGD peptides may be included in a defined culture medium at a concentration of about, for example, about 0.05-0.2 mg/mL or about 0.1 mg/mL. In certain embodiments, ProNectin F may be used to coat a surface for the culture of cells. PRONECTIN F (PnF) is a commercially available RGD peptide which typically contains 13 sites of an arginine-glycine-aspartic acid (RGD).

C. ROCK Inhibitors and PKC inhibitors

In still further aspects of the invention additional media components may be included in ES cell growth media such as molecules that reduce ES cell apoptosis or promote survival after the disassociation of cells (e.g., during splitting of cell populations or prior to the formation of EBs). A defined culture medium may be used to seed, culture, maintain, or differentiate ES cells and may contain an inhibitor of Rho-independent kinase (ROCK) and/or an inhibitor of protein kinase C (PKC). In certain embodiments, a ROCK inhibitor and/or a PKC inhibitor may be used to enhance the survival and differentiation efficiency of pluripotent cells after individualization. In certain embodiments, a ROCK inhibitor and/or a PKC inhibitor may be included in a seeding medium comprising TeSR or mTeSR media and a matrix component.

In certain embodiments, a defined culture media may comprise one or more Rho-associated kinase (ROCK) inhibitor such as Y-27632 or a derivative thereof. Furthermore, in some aspects, a defined media may comprise HA-100:

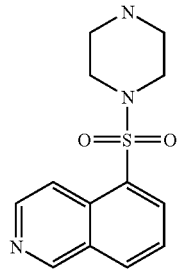

HA-100 or a derivative thereof.

The HA-100 or Y-27632 may be present in an ES cell growth media, e.g., at a concentration of about 1-15 µM, 5-15 µM, 1-30 µM, 5-30 µM, or about 5, 6, 7, 8, 9, 10, 11, 12, 13, 14, 15, 16, 17, 18, 19, 20, 21, 22, 23, 24, 25, 26, 27, 28, 29, or 30 µM, or any range derivable therein. In certain embodiments, HA-100 or Y-27632 is present in an ES cell growth media at about 10-20 µM.

Other ROCK inhibitors which may be included in an ES cell growth media according to the present invention include H-1152 ((S)-(+)-2-Methyl-1-[(4-methyl-5-isoquinolinyl)sulfonyl]homopiperazine). H-1152 exhibits an approximately ten-fold greater potency than HA-100. Thus, H-1152 may be present in an ES cell growth media, e.g., at a concentration of about 0.1-10 µM, about 0.5-5 µM, about 1-3 µM, or about 0.5, 0.6, 0.7, 0.8, 0.9, 1, 2, 3, 4, or 5 µM, or any range derivable therein. In certain embodiments H-1152 is present in an ES cell growth media at about 1 µM. H-1152, which allows for very efficient seeding of individualized human ES cells in 96-well plates (similar to HA-100 but at 10-fold lower concentration). Individualized HES cells that are otherwise passaged in cell clumps allow more uniform cell densities per well, which is a stringent prerequisite for cell-based small molecule screening. H-1152 can thus be used in protocols for ES cell-based small molecule screening which involve automated cell culture according to the present invention. H-1152 has been previously described in, e.g., Ikenoya et al. (2002) and Sasaki et al. (2002), which are incorporated herein by reference.

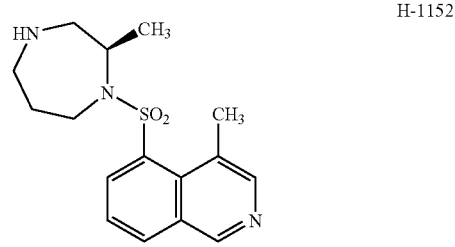 [SMILES: Cc1cncc2cccc(S(=O)(=O)N3CCCNC[C@H]3C)c12]

H-1152

Other ROCK inhibitors which may be included in an ES cell growth media include Y-27632, N-(4-Pyridyl)-N'-(2,4,6-trichlorophenyl)urea, 3-(4-Pyridyl)-1H-indole, glycyl-H1152 ((S)-(+)-2-Methyl-4-glycyl-1-(4-methylisoquinolinyl-5-sulfonyl)homopiperazine) and/or HA1100 (Hydroxyfausdil). Y-27632 ((R)-(+)-trans-4-(1-Aminoethyl)-N-(4-Pyridyl)cyclohexanecarboxamide) is commercially available from Sigma-Aldrich and has been described previously (see, e.g., Maekawa et al., 1999; Davies et al., 2000).

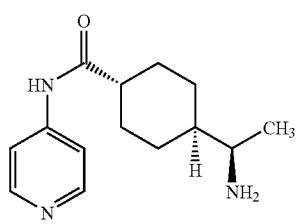

Y-27632

Exemplary ROCK inhibitors which may be used to promote cell survival include, but are not limited to, HA100, H1152, (+)-trans-4-(1-aminoethyl)-1-(pyridin-4-ylaminocarbonyl)cyclohexane dihydro-chloride monohydrate (e.g., WO00078351, WO00057913), imidazopyridine derivatives (e.g., U.S. Pat. No. 7,348,339), substituted pyrimidine and pyridine derivatives (e.g., U.S. Pat. No. 6,943,172) and substituted isoquinoline-sulfonyl compounds (e.g., EP00187371).

It is anticipated that a PKC inhibitor may be used in combination with or as a substitute for a ROCK inhibitor. For example a PKC inhibitor may be used to promote cell survival, e.g., after dissociation or individualization of pluripotent cells prior to differentiation into hematopoietic precursor cells. PKC inhibitors which may be used include, for example, a V5 peptide (e.g., U.S. Pat. No. 7,459,424), polymyxin B, calphostin C, palmitoyl-DL-carnitine, stearoylcarnitine, hexadecylphosphocholine, staurosporine and its derivatives, sangivamycin; safingol, D-erythro-sphingosine; chelerythrine chloride, melittin; dequalinium chloride; ellagic acid, HBDDE, 1-O-hexadecyl-2-O-methyl-rac-glycerol, Hypercin, K-252, NGIC-J, Phloretin, piceatannol, tamoxifen citrate, substituted piperazines and thiazines (e.g., U.S. Pat. No. 6,815,450).

D. Other Components

A defined culture medium may also contain additional components such as nutrients, amino acids, antibiotics, buffering agents, and the like. In certain embodiments a defined culture medium of the present invention may contain nonessential amino acids, L-glutamine, Pen-strep, and monothioglycerol.

BIT 9500 (StemCell Technologies Inc., Vancouver, Canada) may also be included in a defined culture medium of the present invention, e.g., in an amount of about from about 10% to about 30%, or in an amount of about 20%. BIT 9500 contains pre-tested batches of bovine serum albumin, insulin and transferrin (BIT) in Iscove's MDM. BIT 9500 contains 50 mg/mL bovine serum albumin (buffered with NaHCO3), 50 µg/mLrh insulin, 1 mg/mL human transferrin (iron-saturated). In certain embodiments, KOSR may be substituted for BIT 9500 in embodiments where a defined medium is not required. KOSR is an undefined medium which is commercially available (e.g., from Gibco/Invitrogen, catalog #10828) and has been described previously in WO98/30679.

The use of BIT, as described above, may be replaced by HIT; HIT includes the compositions described about in BIT, with the exception that the components, such as serum albumin, are human components (e.g., human serum albumin). For example, the use of HIT may be preferable in embodiments where the risk of a possible infection etc. is of particular concern.

Serum Replacement 3 (Sigma-Aldrich, St. Louis, Mo.) may also be substituted for BIT 9500. Serum Replacement 3 contains only human proteins (i.e., human serum albumin, human transferrin, human recombinant insulin). Serum Replacement 3 does not contain growth factors, steroid hormones, glucocorticoids, cell adhesion factors, detectable Ig or mitogens. As shown in the below examples, inclusion of Serum Replacement 3 can, in certain embodiments, further promote differentiation.

In various embodiments, a defined culture medium may contain one or more vitamin, mineral, salt, lipid, amino acid, or other component. For example, a defined medium of the present invention may contain one or more component present in TeSR medium, e.g., at the same or a comparable concentration as is included in TeSR.

VIII. Separation of Cells

After preparation of hematopoietic (e.g., CD34+, CD43+) precursor cells or endothelial cells (e.g., CD31+) from embryonic stem cells, it may be desirable to substantially purify or separate one or more sub-population of further or substantially differentiated cells (e.g., hematopoietic precursor cells, endothelial cells, etc.) from the cell population. Methods for separation of cells using flow cytometry, such as FACS, or magnetic activated cell sorting may be used to separate hematopoietic cells from a heterogeneous cell population.

A. Magnetic Activated Cell Sorting (MACS)

CD34+, CD43+, CD31+, and/or CD45+ cells may be isolated from differentiated hESCs using a magnetic activated cell sorter (MACS). MACS typically utilizes an antibody, such as a anti-CD34 antibody, in combination with magnetic beads to separate cells over a column. MACS may, in certain embodiments, be more gentle on cells and favorably affect cell viability and integrity as compared to FACS, possibly due to the laser illumination of cells involved with FACS.

Various MACS products are commercially available, including MACS MicroBeads™ columns or AutoMACS™ (Miltenyi Biotec, CA, USA), which may be used according to the manufacturer's instructions. PBS/0.5% BSA (without EDTA) may used as the buffer for cell isolation. In some experiments, a Dead Cell Removal Kit (Miltenyi Biotec) may be used to remove dead cells prior to isolation of CD34+ cells. Repeated MACS columns may be used if necessary.

B. FACS

Fluorescence activated cell sorting (FACS) may also be used to separate CD34+ cells. FACS utilizes the degree or fluorescence exhibited by a cell, e.g., due to bound an anti-CD34 antibodies comprising a fluorescent tag, to separate cells. In this way FACS may be used to separate hematopoietic CD34+ cells from a heterogeneous cell population.

For example, the following protocol may be used to perform FACS to quantify hematopoietic cells. Cells may be prepared in PBS containing 1% FBS or 0.5% BSA, and labeled for 15-30 minutes at 4° C. with a combination of monoclonal antibodies (mAbs), such as CD31-PE (clone WM-59), CD34-APC (clone 581, 8G12), CD45-FITC (clone HI30) (all from BD PharMingen), and KDR-PE (clone 89106) (R&D system). A 1:50 dilution for specific antibodies, and 1:200 dilution for IgG control may be used. The samples may be analyzed by a FACSCalisbur™ (Becton-Dickson, New Jersey, U.S.A.).

IX. Bioreactors and Robotic Automation

One or more steps for the culture of stem cells and/or differentiation of hematopoietic progenitor cells from embryonic stem cells may be automated. Automating a process using robotic or other automation can allow for more efficient and economical methods for the production, culture, and differentiation of cells. For example, robotic automation may be utilized in conjunction with one or more of the culture of human embryonic stem cells, passaging, addition of media, addition of differentiation media, culture in differentiation media, and separation of cell type, e.g., using magnetic separation or FACS.

A bioreactor may also be used in conjunction with the present invention to culture, maintain, and/or differentiate cells (e.g., human embryonic stem cells, CD34+ cells, hematopoietic cells, etc.) according to the present invention. Bioreactors provide the advantage of allowing for the "scaling up" of a process in order to produce an increased amount of cells. Various bioreactors may be used with the present invention, including batch bioreactors, fed batch bioreactors, continuous bioreactors (e.g., a continuous stirred-tank reactor model), and/or a chemostat.

For example, spinner flasks may be used to scale up methods for the maintenance and/or differentiation of pluripotent cells to allow for the generation of increased numbers of cells. In certain embodiments, the following protocol may be used to promote EB formation in spinner flasks: Undifferentiated hESC's and iPSC's may be adapted to feeder free growth on Matrigel coated plates and harvested at confluence, e.g., using TrypLE treatment for about 5 minutes at about 37° C. The cells may be harvested in EB basal media containing IMDM supplemented with about 20% BIT9500 (Stem Cell Technologies) or Serum Replacement-3 (Sigma Aldrich), about 1% NEAA, about 1 mM L-glutamine, and about 0.1 mM mercaptoethanol, about 0.75% BSA, about 50 ug/ml ascorbic acid and about 1 µM ROCK inhibitor (e.g., H-1152). The cells may then be placed in spinner flasks (e.g., 125 ml Corning) at a density of about 0.5-2 million cells per ml. The spinners may be set to 30-40 rpm overnight to facilitate EB formation. Alternately the cells could be placed under static conditions for 24 hours in low attachment plates. It is generally recognized that the cell density and/or speed of spinner flask movement may be varied depending on the particular spinner flask or bioreactor used. After about 12-24 hrs of culture the cells may be placed in an EB differentiation media containing cytokines without the ROCK inhibitor on a magnetic stir platform in a spinner flask, e.g., rotating at a speed of about 60 RPM. The side caps of the spinner flasks may be loosened to allow gas transfer. The cells may be placed in EB basal media supplemented with about 50 ng/ml bone morphogenetic factor (BMP-4), about 50 ng/ml vasular endothelial growth factor (VEGF), and about 25 ng/ml zebrafish FGF-2. On about the fourth day of differentiation the cells may be fed by allowing the spinner flask to remain still so that the suspended EB aggregates can settle to the bottom of the flask for 15-20 minutes. The spent media may then be aspirated (e.g., with allowing about 20 mL to remain in a 125 ml spinner). The cells may then be gently swirled and fresh media containing about 50 ng/ml bone morphogenetic factor (BMP-4), about 50 ng/ml, vasular endothelial growth factor (VEGF), and about 25 ng/ml zebrafish FGF-2 may be added to the cells. The spinner flasks may be set to a speed of about 40-60 rpm throughout the entire process of hematopoietic differentiation, although it is anticipated that substantially higher or lower speeds of rotation may be utilized. On about day 5-6 of differentiation the spent media was aspirated as described above and the cells may be placed in EB basal media supplemented with, e.g., either: (1) about 25 ng/ml of Flt-3 ligand, about 10 mg/ml of IL-3 and about 10 ng/ml GMCSF, or with (2) about 25 ng/ml of Flt-3 ligand, about 25 ng/ml of SCF, about 25 ng/ml of TPO, about 10 ng/ml IL-3, and about 10 ng/ml IL-6. Spent media may be aspirated on about day 8 and 10 as described above. The EB cultures may be harvested on about day 12 of differentiation. Cells may be stained for the phenotypic expression of surface markers (e.g., CD34+, CD45+, CD43+, CD41+, CD235a+, CD31+) to quantify the hematopoietic progenitor content of the population. As shown in the below examples, these approaches can be successfully used to generate a variety of cell lineages (e.g., erythroid, megakaryocyte, macrophage, dendritic cells, mast cells, granulocyte), and similar results may be obtained using iPS cells or hESC.

Robotic automation specifically envisioned for use with the present invention may be obtained from, for example, Tecan (CA, USA). Robotics may include liquid handling tools such as cap-piercing probes and disposable tips to minimize carry-over between samples. In various embodiments, robotics may be utilized in conjunction with one or more bioreactor for culturing cells (e.g., during the maintenance or growth of hESCs, the differentiation of hESCs into hematopoietic cells, or the differentiation of hematopoietic cells into subsequent lineages such as erythrocytes, etc.). As shown in the below examples, conditions for the maintenance and generation of hematopoietic precursor cells may be at least partially or completely automated using the Tecan Cellerity™ system (an industrially relevant robotic platform). The Tecan Cellerity™ is equipped with Tecan liquid handling robot (Freedom EVO 200), an automated incubator (Storex500) with a capacity for 500 Roboflasks™, a media storage refrigerator, a Cedex cell counter, spinner flasks for expansion and seeding of suspension cells' and a ROMA robotic arm to handle plates and an 8-channel fixed tip pipette. Part, essentially all, or all of EB differentiation protocol may be automated. For example, on day 12 of differentiation the cells may be harvested by the Tecan Cellerity system and washed manually for cell surface staining of markers. Post staining, the cells may be analyzed using the Hypercyt connected to the Accuri flow cytometer. This process may be used for high-throughput screening of hematopoietic precursor populations. In certain embodiments, undifferentiated hESCs or iPSCs may be cultured on the robot, e.g., using Matrigel™ coated roboflasks (Corning) via the method described above. The maintenance, seeding, feeding and/or harvesting of the EBs may be partially or completely automated, e.g., using the Tecan Cellerity™ system. This robot has the capacity to include spinner flasks or a bioreactor may be used to generate large numbers of cells.

In certain embodiments, it may be useful to miniaturize or "scale down" methods of the present invention. These approaches may be particularly useful, e.g., where the methods comprise a high-throughput screen of compounds, e.g., which may promote de-differentiation or differentiation of cells towards a particular lineage. High-throughput screens may also be used to evaluate one or more property of a candidate substance (e.g., toxicity, ability to promote or reduce differentiation, etc.). Miniaturization of the methods may involve the use of low-attachment plates (e.g., 96 well plates) and/or culture of cells under low oxygen (e.g., less than about 25% $O_2$ or about 5% $O_2$) conditions. In certain embodiments, the following methods may be used: Undifferentiated hESC's or iPSC's adapted to feeder free growth on Matrigel coated plates may be preconditioned for 24 hours using TeSR without growth factors supplemented with about 0.1 ng/ml TGF and about 20 ng/ml zebrafish FGF. The cells may be harvested at confluence, e.g., using TrypLE treatment for about 5 minutes at about 37° C. The cells may be collected in EB basal media containing IMDM supplemented with about 20% BIT9500 or Serum Replacement-3, about 1% NEAA, about 1 mM L-glutamine, and about 0.1 mM mercaptoethanol, about 0.75% BSA, about 50 µg/ml ascorbic acid and about 1 µM ROCK inhibitor (e.g., H-1152). To initiate EB formation, the cells may be placed in low attachment 96 well plates at a density of about 0.1 million cells per well in EB basal containing a ROCK inhibitor. It is anticipated that the exact concentration of cells used may be varied to achieve a similar effect. EB formation may also be facilitated by incubating the plated at low $O_2$ conditions. After about 12-24 hrs the cells may be placed in EB differentiation media containing about 50 ng/ml bone morphogenetic factor (BMP-4), about 50 ng/ml vasular endothelial growth factor (VEGF), and about 25 ng/ml zebrafish FGF-2. About 300 µl of media was may be used per well in, e.g., a 96 well plate. On about day 3-4 of differentiation, the cells may be half fed by gently removing half the volume of spent media (e.g., between 100-150 µl) and adding equal volume of fresh media. On about day 5-6 of differentiation, the spent media may be aspirated as described above and the cells may be placed in EB basal media, e.g., supplemented with either: (1) about 25 ng/ml of Flt-3 ligand, about 10 mg/ml of IL-3 and about 10 ng/ml GMCSF, or (2) media containing about 25 ng/ml of Flt-3 ligand, about 25 ng/ml of SCF, about 25 ng/ml of TPO, about 10 ng/ml IL-3, and about 10 ng/ml IL-6. The differentiating EB cultures may be half fed with fresh media on about day 8 and 10 of differentiation as described above. EB cultures may be harvested on about day 12 of differentiation. As shown in the below examples, these approaches can be successfully used to generate a variety of cell lineages (e.g., erythroid, megakaryocyte, macrophage, dendritic cells, mast cells, granulocyte), and similar results may be obtained using iPS cells or hESC.

Methods of the present invention may be utilized in a single cell assay, using robotic automation, by including the ROCK inhibitors HA100 and/or H1152 in the media to induce cells to adhere single cells to a plate. On the robot, the addition of the small molecules HA100 or H1152 or Y-27632 to the culture system can greatly improve the viability of pluripotent cells, including ES, hESC, and iPS cells. In certain embodiments, survival of pluripotent cells in a TeSR media can be improved by the inclusion of a ROCK inhibitor or a PKC inhibitor, particularly after the cells are proteolytically or mechanically separated into clumps or individualized. The ROCK inhibitors can promote individualized hES cells to attach to a surface and grow. Some or all of the process of maintenance or proliferation of pluripotent cells, as well as differentiation into hematopoietic precursor cells or a specific hematopoietic lineage may be automated. Part of all of the automated methods may utilize defined conditions.

X. Kits

The present invention also contemplates kits for use in accordance with the present invention. For example, a kit may comprise a differentiation medium described herein in one or more sealed vials. The kit may include a cell, such as a pluripotent stem cell, progenitor cell, hematopoietic progenitor cell, or endothelial progenitor cell.

The kit may also include instructions for producing progenitor cells, such as hematopoietic progenitor cells or endothelial progenitor cells. Alternatively, the instructions may be directed to producing hematopoietic cells, endothelial cells, mast cells, dendritic cells, megakaryocytes, granulocytes, macrophages, or erythrocytes.

Suitable kits include various reagents for use in accordance with the present invention in suitable containers and packaging materials, including tubes, vials, and shrink-wrapped and blow-molded packages. Materials suitable for inclusion in a kit in accordance with the present invention include, but are not limited to, one or more defined media as described herein and one or more cell, wherein the cell is a pluripotent cell or a pluripotent cell that has been at least partially differentiated according to the methods presented herein. In certain preferred embodiments, a plurality of pluripotent cells or at least partially differentiated cells are included in a kit in accordance with the present invention.

XI. Screening Assays

The invention contemplates screening assays, such as a screening assay useful for identifying a candidate substance for ability to promote differentiation of a pluripotent stem cell into a progenitor cell. For example, hematopoietic cells, hematopoietic precursor cells, and/or endothelial cells may be used to evaluate the pharmacology and/or toxicology of a candidate substance. Thus, screening methods using cells differentiated via methods described herein may be used to identify a therapeutic compound which may alleviate one or more symptom associated with a disease which can affect the cells. In other embodiments, the differentiated cells may be utilized to identify a compound which results in toxicity in the cells. Alternately, the screening methods may comprise exposing the cells to a candidate substance which can promote the differentiation or de-differentiation of cells.

As used herein the term "candidate substance" refers to any substance that promotes differentiation of a pluripotent stem cell into a progenitor cell. Candidate substances can include fragments or parts of naturally-occurring compounds or may be only found as active combinations of known compounds that are otherwise inactive. In one embodiment, the candidate substances are small molecules. In yet other embodiments, candidate substances may include, but are not limited to, small organic molecules, peptides or fragments thereof, peptide-like molecules, nucleic acids, polypeptides, peptidomimetics, carbohydrates, lipids, proteins, enzymes, salts, amino acids, vitamins, matrix components, inhibitors, antibiotics, antibodies, antibody fragments, minerals, lipids, or other organic (carbon-containing) or inorganic molecules.

XII. Pharmaceutical Preparations

Cells differentiated via methods described herein, or derived from cells differentiated via the methods described herein, may be included in a pharmaceutical preparation and administered to a subject, such as a human patient. The pharmaceutical preparation may be administered, in certain embodiments, parenterally or intravenously.

Pharmaceutical compositions of the present invention comprise an effective amount of one or more hematopoietic, myeloid, or erythroid cell or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one hematopoietic, myeloid, or erythroid cell or additional active ingredient will be known to those of skill in the art in light of the present disclosure, as exemplified by Remington: The Science and Practice of Pharmacy, 21$^{st}$ Ed., by University of the Sciences in Philadelphia, which is incorporated herein by reference. Moreover, for animal (e.g., human) administration, it will be understood that preparations should meet sterility, pyrogenicity, general safety and purity standards as required by FDA Office of Biological Standards. Generally, it will be appreciated that the pharmaceutical preparation will typically be formulated to promote the viability of the hematopoietic, myeloid, or erythroid cells present in the formulation. For example, in certain embodiments, the composition may comprise red blood cells in a solution for intravenous administration to a human patient.

The present invention further contemplates methods of treating a disease, disorder, or injury by administering to a subject a pharmaceutically effective amount of progenitor cells, hematopoietic cells, or endothelial cells obtained by methods disclosed herein. Administration of these compositions according to the present invention will be via any common route so long as the target tissue is available via that route. This includes administration by systemic or parenteral methods including intravenous injection, intraspinal injection, or intracerebral, intradermal, subcutaneous, intramuscular, or intraperitoneal methods. Depending on the nature of the therapeutic, administration may also be via oral, nasal, buccal, rectal, vaginal or topical means.

Diseases or disorders that may be treated by methods disclosed here include, but are not limited to, a vascular disease or disorder, an immunological disease or disorder, a neuronal disease or disorder, a blood disease or disorder, or an injury.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Making EBs: Undifferentiated hESC's and iPSC's that were adapted to feeder free growth on Matrigel™ coated plates were harvested at confluence using collagenase IV (1 mg/ml) treatment for 10 minutes at 37 C. The wells were washed free of collagenase after the incubation and the EBs were formed by scraping the wells in EB basal media. The media was changed the next day to EB differentiation media containing different cytokine formulations.

Undifferentiated hESC's and iPSC's that were adapted to feeder free growth on Matrigel™ coated plates were harvested at confluence using TrypLE™ treatment for 6 minutes at 37 C. TrypLE™ in the wells was neutralized using "EB basal media" containing 1 µM ROCK inhibitor, Soybean trypsin inhibitor (0.25 mg/ml). The cells were collected and washed in EB basal media containing 1 µM ROCK inhibitor, Soybean trypsin inhibitor (0.25 mg/ml). The cells were counted to check viability and plated in low attachment plates in EB basal media containing 1 µM ROCK inhibitor, Soybean trypsin inhibitor (0.25 mg/ml). The media was changed the next day to EB differentiation media containing different cytokine formulations.

EB formation and differentiation protocol: To promote EB formation using the abovementioned enzymes, the cells were transferred to 6-well low-attachment plates for an overnight incubation in "EB basal media" containing IMDM supplemented with 20% BIT9500 (Stem Cell Technologies), 1% NEAA, 1 mM L-glutamine, and 0.1 mM mercaptoethanol (all from Invitrogen, Carlsbad, Calif.), 0.75% BSA, 50 ug/ml ascorbic acid. On the next day the cells were collected from each well and centrifuged. The cells were resuspended in "EB-differentiation media," which consists of EB basal media supplemented with the following growth factors and cytokines: 50 ng/ml bone morphogenetic factor (BMP-4), 50 ng/ml Vasular Endothelial Growth factor (VEGF), 25 ng/ml stem cell factor, (SCF); 25 ng/ml Flt-3 ligand (Flt-3L), 10 ng/ml interleukin-3 (IL-3), 10 ng/ml interleukin-6 (IL-6), 20 ng/ml granulocyte colony-stimulating factor (G-CSF or GCSF); 20 ng/ml granulocyte macrophage, colony-stimulating factor (GM-CSF or GMCSF), 0.2 U/ml Erythropoietin (EPO), 25 ng/ml Thrombopoieitin (TPO) (all from R&D Systems, Minneapolis, Minn.), and 25 ng/ml zebrafish FGF-2. The media was changed every four days by transferring the EB's into a 15-mL tube and letting the aggregates settle for 5 minutes. The supernatant was aspirated and replaced with fresh differentiation medium. Alternately the cells were half fed every two days with fresh media. The cells were harvested at different time points during the differentiation process and the phenotype was assessed by flow cytometry and the functional capability was assessed using the CFU assay.

Flow cytometry: Cells were collected from each well/condition and washed once with media. The cell pellet was digested using TrypLE™ or 0.5% trypsin for 5-10 minutes in a 37° C. incubator followed by washes with media and passage through a 70-µm cell strainer. The cells were resuspended in PBS-FBS containing FACS buffer, counted to estimate cell viability and stained with fluorochrome-conjugated monoclonal antibodies: anti-human CD43 (1G10), anti-human CD31 (WM-59), anti-human CD41 (HIPS); anti-human CD45 (HI30) and anti-human CD34 (581, 8G12) (BD Biosciences San Jose, Calif.); anti-human flk-1 (89106), (from R&D Systems, Minneapolis, Minn.). Non-viable cells were excluded with 7-aminoactinomycin D (7-AAD, BD Biosciences). Live cell analysis was performed on a FACSCalibur™ or Accuri flow cytometer and Cell Quest software.

Clonogenic hematopoietic progenitors assay (CFU assay): EBs were dispersed into single cell suspensions using TryplE or 0.5% trypsin/EDTA. Viable cells were quantified, plated (50,000-300,000 cells per mL), and assayed in humidified chambers for hematopoietic CFCs in using Human Methylcellulose Complete Media (R&D Systems, Minneapolis, Minn.) containing stem cell factor (SCF) 50 ng/mL, erythropoietin (EPO) 3 U/mL, granulocyte-macrophage colony-stimulating factor (GM-CSF) 10 ng/mL, interleukin-3 (IL-3) 10 ng/mL. After 14 days the colonies were scored according to their morphology and colonies per $10^5$ cells plated were quantified. Serum-containing or Serum-Free MethoCult™ media (Stem Cell Technologies) can be used to generate colonies.

Cytopspins: Cells were fixed and stained with Wright-Giemsa reagents (Hema 3 stain; Fisher Scientific, Hampton, N.H.) according to the manufacturer's instructions.

Example 2

The in vitro aggregation of human embryonic stem cells (hESCs) or iPSC induced into clusters termed embryoid bodies (EBs) allows for the differentiation of cells representing endoderm, mesoderm, and ectoderm lineages. This stochastic process for EB formation can be steered to generate hematopoietic precursor cell types by the addition of exogenous growth factors.

The inventor has established a novel feeder free and serum free defined EB based hematopoietic differentiation protocol with a set of five essential cytokines to generate hematopoietic precursor cells expressing CD43+, CD34+, CD31+ and CD45+ on the cell surface between days 9-13 days of differentiation. The efficiency of generating the precursor cell type was between 5-8% across two human hESCs and four iPSCs. EBs formed using 200-1000 cells per aggregate, hypoxia, and a reaggregation step during the differentiation process favors the generation of hematopoietic precursor cell types.

The method can efficiently generate myeloid progenitor cells co-expressing CD31, CD43, and CD45 on the cell surface after between 16-24 days in culture in the presence of the five cytokines. Alternately, the hematopoietic precursor cell can be isolated and are capable of further differentiating in to megakaryocytes, erythroid and myeloid lineages (e.g., immature to mature polymorph nuclear granulocytes, macrophages, dendritic cells) when placed in a specialized cytokine rich media formulation for each specific lineage of cells.

Embryonic Stem Cells

The undifferentiated human embryonic stem cell lines (hESCs) and induced pluripotent stem cell lines iPSCs were maintained by co culture with irradiated murine embryonic fibroblasts (MEFs) in Dulbecco's modified Eagle's medium (DMEM)/Ham's F-12 medium (F12) supplemented with 15% KO-serum supplement (Invitrogen), 1% nonessential amino acids (NEAA), 1 mM L-glutamine (all from Invitrogen, Carlsbad, Calif.), 0.1 mM f3-mercaptoethanol (Sigma-Aldrich, St. Louis). The medium was supplemented with 4 ng/ml zebrafish basic fibroblast growth factor (bFGF) for hESCs and 100 ng/ml human basic fibroblast growth factor (bFGF) for iPSCs.

Undifferentiated hESCs and iPSCs that were grown on irradiated mouse embryonic fibroblasts or adapted to feeder-free growth on Matrigel™-coated plates maintained using MEF-conditioned media (MEF-CM) or mTeSR media were used as starting material for the EB differentiation protocol.

Preconditioning Cells Prior to Differentiation

The cells were hESCs and iPSCs maintained on matrigel coated plates using mTeSR media were subjected to a preconditioning step prior to the onset of differentiation. The preconditioning step varied from 1-3 days.

X-vivo 15 (Cambrex) supplemented with 0.1 ng/ml TGF-β and 20 ng/ml FGF-2, or mTeSR devoid of growth factors ("mTeSR-GF") supplemented with 0.1 ng/ml TGF-β and 20 ng/ml FGF-2 was used for preconditioning step prior to the onset of EB differentiation.

Harvesting Cells for EB Formation

Method 1: Undifferentiated hESCs and iPSCs growing on MEFs or adapted to feeder-free growth on Matrigel-coated plates were harvested at confluence using collagenase IV (1 mg/ml) treatment for 10 minutes at 37 C. The wells were washed free of collagenase after the incubation and the EBs were formed by scrapping the wells in EB basal media. The media was changed the next day to EB differentiation media containing different cytokine formulations.

Method 2: Undifferentiated hESCs and iPSCs that were adapted to feeder free growth on Matrigel™ coated plates were harvested at confluence using TrypLE™ treatment for 6 minutes at 37 C. TrypLE™ in the wells was neutralized using EB basal media containing 1 μM ROCK inhibitor (H-1152) or 10 μM ROCK inhibitor (Y-27632) Soybean trypsin inhibitor (0.25 mg/ml). The cells were collected and washed in EB basal media containing 1 μM-10 μM ROCK inhibitor, Soybean trypsin inhibitor (0.25-0.5 mg/ml). SoybeanTrypsin Inhibitor was included when Trypsin was used for individualizing the cells. In instances where TrypLE was used to individualize the cells, the soybean trypsin inhibitor can be excluded. The cells were counted to check viability and plated in low attachment plates in EB basal media containing 1 μM-10 μM ROCK inhibitor, Soybean trypsin inhibitor (0.25-0.5 mg/ml). The media was changed the next day to EB differentiation media containing different cytokine formulations.

EB Formation and Differentiation Protocol

To promote EB formation using the abovementioned enzymes, the cells were transferred to 6-well low-attachment plates for an overnight incubation in mTeSR media or EB basal media containing IMDM supplemented with 20% BIT9500 (Stem Cell Technologies), 1% NEAA, 1 mM L-glutamine, and 0.1 mM mercaptoethanol (all from Invitrogen, Carlsbad, Calif.), 0.75% BSA, 50 ug/ml ascorbic acid. On the next day the cells were collected from each well and centrifuged. The cells were resuspended in EB-differentiation media. EB-differentiation media consists of EB basal media supplemented with the following growth factors and cytokines: 50 ng/ml bone morphogenetic factor (BMP-4), 50 ng/ml vascular endothelial growth factor (VEGF), 25 ng/ml stem cell factor (SCF); 25 ng/ml Flt-3 ligand (Flt-3L), 10 ng/ml interleukin-3 (IL-3), 10 ng/ml interleukin-6 (IL-6), 20 ng/ml granulocyte colony-stimulating factor (G-CSF); 20 ng/ml granulocyte macrophage, colony-stimulating factor (GM-CSF), 0.2 U/ml Erythropoietin (EPO), 25 ng/ml Thrombopoietin (TPO) (all from R&D Systems, Minneapolis, Minn.), and 25 ng/ml zebrafish FGF-2. The media was changed every four days by transferring the EB's into a 15-mL tube and letting the aggregates settle for 5 minutes. The supernatant was aspirated and replaced with fresh differentiation medium. Alternately the cells were half fed every two days with fresh media. The cells were harvested at different time points during the differentiation process and the phenotype was assessed by flow cytometry and the functional capability was assessed using the CFU assay.

The media was changed every 4 days or a half media change every 48 hrs was performed by transferring the EBs into a 15-ml tube and letting the aggregates settle for 5 minutes. The supernatant was aspirated and replaced with fresh differentiation medium.

Results

EBs made in mTESR media from hESCs adapted to mTesR revealed a lower frequency (<4%) of hematopoietic precursors after 16 days of differentiation in comparison to EBs made from hESCs and iPSCs maintained on irradiated mouse embryonic fibroblasts or adapted to feeder-free growth on Matrigel™-coated plates maintained using MEF-conditioned media instead of mTeSR. The latter conditions generated between 10-15% hematopoietic precursor cells. Without wishing to be bound by any theory, higher levels of TGF-β in mTeSR media may exert a preferential growth-inhibitory effect on the most primitive stem/progenitor cells.

The presence of cytokines was observed to be essential to drive the serum free hematopoietic differentiation process for both hESCs and iPSCs. The initial cytokine formulation included 11 cytokines listed the EB differentiation media. The frequency of the hematopoietic precursor cells was between 0.5-2% in the absence of serum and cytokines, and between 2-10% in the presence of serum with no cytokines The frequency of the hematopoietic precursor cells was between 10-40% in the absence of serum and presence of cytokines beyond 16 days of differentiation Addition of serum to the media containing cytokines resulted in a marginal augmentation of precursor cells. Thus serum free cytokine rich EB differentiation medium was capable of generating hematopoietic precursor cells from hESCs and iPSCs maintained on matrigel coated plates using mTeSR media, preconditioned using MEF-CM, as well as hESCs and iPSCs maintained on irradiated mouse embryonic fibroblasts.

The predominant phenotype of the cells at the end of differentiation 16-18 days of EB differentiation was CD45+ CD43+ and CD31+ cells. CFU assays revealed the presence of a myeloid precursor capable of generating granulocytes (e.g., eosinophils, basophils, neutrophils, monocytes, macrophages, dendritic cells, mast cells).

FIG. 1 shows hematopoietic differentiation of H1 ESCs at passage 50 (A) and 40(B). Both hESCs were maintained on Matrigel™ for 10 passages using mTeSR. hESCs were preconditioned for 3 days using MEF-CM prior to the onset of hematopoietic differentiation. The cells were harvested using collagenase and the EBs differentiated using a serum free cytokine rich media. The EB cells were analyzed by flow cytometry at different time points for the presence of hematopoietic precursor cell types (CD43, CD34, CD45, CD31 and CD41). Values represent the mean SEM of three individual experiments.

Figure 2:
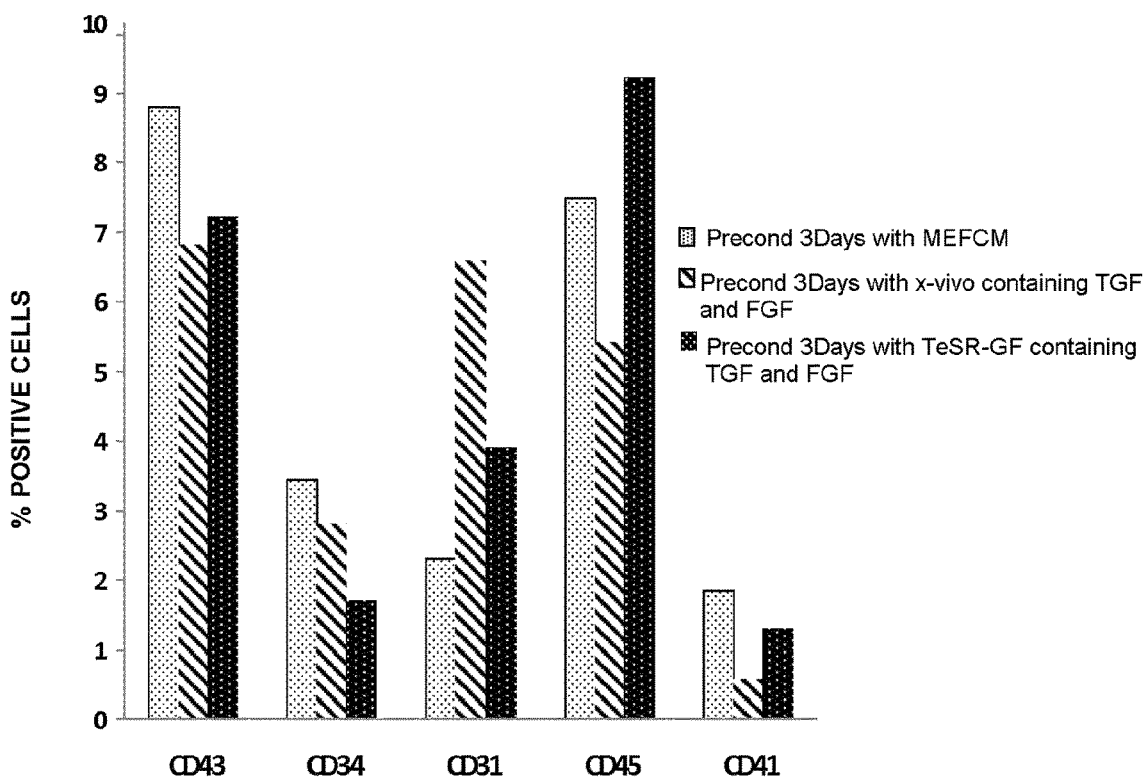
FIG. 2: Exposure to a defined pre-conditioning medium improves hematopoietic differentiation. hESCs and iPSCs maintained in defined conditions and adapted to feeder cell-free growth on Matrigel coated plates using mTESR were used.

Preconditioning cells in a defined medium with reduced amounts of FGF-2 and TGF-β improved hematopoietic differentiation. FIG. 2 shows that exposure to a defined preconditioning medium for hESCs and iPSCs adapted to feeder free growth on Matrigel™ maintained using mTESR augments subsequent hematopoietic differentiation. More specifically, H1 hESCs adapted to feeder free growth on Matrigel™ coated plates were preconditioned for 3 days using either MEFCM, or X-vivo 15 supplemented with 0.1 ng/ml TGF-β and 20 ng/ml FGF-2, or mTeSR (devoid of growth factors) supplemented with 0.1 ng/ml TGF-β and 20 ng/ml FGF-2. The preconditioning media was changed every day for 3 days. The cells were harvested using collagenase and the EBs were formed by scrapping in EB basal media. The cells were transferred to EB differentiation media containing 11 cytokines 24 hours post plating in to EB basal media. The cells were harvested on day 12 of differentiation and the phenotype of the cells was quantified by flow cytometry.

It was further observed that the time frame of preconditioning can be as short as 1 day and still result in improvements in hematopoietic differentiation. mTeSR lacking growth factors (mTeSR-GF) supplemented with low levels of TGF-β (0.1 ng/ml) and FGF-2 (20 ng/ml) is a preferred preconditioning media. It is anticipated that the beneficial effects of preconditioning will also be observed for EBs individualized or separated into small clumps using a trypsin (e.g., TrypLE™).

Example 3

Hematopoietic precursors were produced from single cell suspensions of hESCs and iPSCs. Single cell suspensions, or individualized cells, were produced by trypsin digestion.

Methods Used for Making EBs from Single Cells hESCs and iPSCs adapted to feeder free growth on matrigel maintained using mTESR were preconditioned for three days in the presence of mTesR-GF containing 0.1 ng/ml TGF-β and 20 ng/ml FGF-2. To initiate differentiation from single cells the, the cultures were treated with TrypLE™ Select (Invitrogen) for 6 minutes and the cells suspension was collected in (1) plain EB basal media, (2) EB basal media containing PVA, (3) EB basal media containing 0.5% PVA and 1 μM H1152 or 10 μM Y27632 ROCK inhibitor, or (4) EB basal media containing only 1 uM H1152 ROCK inhibitor. The cells were collected and washed once and plated in the respective media formulations on a low attachment plate at 37 C. The EB formation status was checked at 18-24 hrs later under a phase contrast microscope.

TABLE 3

EB formation using ROCK inhibitors/PVA

| Rho Associated Coil Kinase (ROCK) inhibitor Y-27632 or H1152 | Poly Viny Alcohol PVA | EB status |
| --- | --- | --- |
| absent | absent | Not formed |
| absent | present | Few EBs Formed |
| present | present | Formed |
| present | absent | Formed |

Cytokines Required for Hematopoietic Differentiation

Cytokine matrix experimental Protocol: hESCs adapted to feeder free growth on matrigel maintained using mTESR were preconditioned for three days in the presence of X-vivo-15 containing 0.1 ng/ml TGF-β and 20 ng/ml FGF-2. Cells were harvested using TrypLE for 6 minutes at 37 C. TrypLE™ was neutralized using EB basal media containing 1 μM ROCK inhibitor (H-1152), Soybean trypsin inhibitor (0.25 mg/ml). The cells were washed once in EB basal media containing 1 μM ROCK inhibitor and soybean trypsin inhibitor (0.25 mg/ml). The cells were plated in low attachment plates in EB basal media containing 1 μM ROCK inhibitor and soybean trypsin inhibitor (0.25 mg/ml). The media was changed the next day to EB basal media containing different cytokine formulations.

The concentration of cytokines used is as follows: 25 ng/ml BMP-4, 25 ng/ml VEGF, 25 ng/ml SCF, 25 ng/ml Flt-3L, 10 ng/ml IL-3, 10 ng/ml IL-6, 20 ng/ml G-CSF; 20 ng/ml GM-CSF, 0.2 U/ml EPO, 10 ng/ml TPO and 10 ng/ml zebrafish FGF-2.

The cytokine combinations used are listed below in Table 3. The EB cultures were half fed with fresh differentiation media every two days. The EB cultures were harvested on day 8, 12 and 17 of differentiation. The EB cultures were harvested by spinning down all the cells and digesting the EBs with TrypLE™ or 0.5% trypsin. The phenotype of the progenitor cell types was analyzed by flow cytometry and the cells were plated in methylcellulose media for CFU assays. "FLT3" refers to the Flt3 ligand below.

TABLE 3

| Set # | Cytokine Combinations |
| --- | --- |
| 1. | SCF/FLT-3/BMP-4/VEGF/FGF/EPO/TPO/IL3/IL6/GCSF/GMCSF |
| 2. | FLT3/VEGF/FGF/EPO/GCSF |
| 3. | BMP4/FGF/EPO/TPO/GMCSF |
| 4. | SCF/VEGF/EPO/TPO/1L3 |
| 5. | FLT3/FGF/TPO/1L3/1L6 |
| 6. | BMP4/EPO/IL3/ 1L6/GCSF |
| 7. | VEGF/TPO/IL6/GCSF/GMCSF |
| 8. | SCF/IL3/GCSF/GMCSF |
| 9. | SCF/FLT-3/EPO/IL6/GMCSF |
| 10. | SCF/FLT-3/BMP4/TPO/GCSF |
| 11. | FLT-3/BMP-4/VEGF/IL3/GMCSF |
| 12. | SCF/BMP4/VEGF/FGF/IL6/ |

The results of these based on these different combinations are presented below in Table 4. As listed below, cells resulting from culture in these different combinations of growth factors were evaluated to determine the expression of various cell surface markers.

TABLE 4

| | Results | | | | | | | | | | |
| --- | --- | --- | --- | --- | --- | --- | --- | --- | --- | --- | --- |
| Factors | SCF 1 | FLT-3 2 | BMP4 3 | VEGF 4 | FGF 5 | EPO 6 | TPO 7 | IL3 8 | IL6 9 | GCSF 10 | GMCSF 11 |
| DAY 8 PRESENT | | | | | | | | | | | |
| CD43 | 1.0% | 1.4% | 1.6% | 1.6% | 1.0% | 0.8% | 0.8% | 1.4% | 1.0% | 0.8% | 1.4% |
| CD31 | 0.9% | 1.0% | 1.3% | 1.1% | 0.9% | 0.7% | 0.8% | 1.0% | 0.8% | 0.7% | 1.1% |
| CD45 | 0.2% | 0.2% | 0.2% | 0.2% | 0.2% | 0.2% | 0.2% | 0.2% | 0.2% | 0.2% | 0.2% |
| CD34 | 1.5% | 1.4% | 1.7% | 1.5% | 1.5% | 1.1% | 1.3% | 1.3% | 1.4% | 1.1% | 1.3% |
| FLK-1 | 2.0% | 2.2% | 2.4% | 1.8% | 2.4% | 1.7% | 1.9% | 2.3% | 2.6% | 1.7% | 1.7% |
| ABSENT | | | | | | | | | | | |
| CD43 | 0.8% | 0.3% | 0.1% | 0.1% | 0.8% | 1.0% | 1.0% | 0.3% | 0.8% | 1.0% | 0.3% |
| CD31 | 0.7% | 0.5% | 0.2% | 0.4% | 0.7% | 0.8% | 0.8% | 0.5% | 0.8% | 0.8% | 0.4% |
| CD45 | 0.2% | 0.2% | 0.2% | 0.1% | 0.2% | 0.2% | 0.2% | 0.2% | 0.2% | 0.2% | 0.2% |
| CD34 | 0.8% | 0.9% | 0.5% | 0.7% | 0.8% | 1.2% | 1.0% | 1.0% | 0.9% | 1.2% | 1.0% |
| FLK-1 | 1.9% | 1.6% | 1.4% | 2.0% | 1.4% | 2.2% | 1.9% | 1.5% | 1.2% | 2.2% | 2.2% |

TABLE 4-continued

| | Results | | | | | | | | | | |
|---|---|---|---|---|---|---|---|---|---|---|---|
| Factors | SCF 1 | FLT-3 2 | BMP4 3 | VEGF 4 | FGF 5 | EPO 6 | TPO 7 | IL3 8 | IL6 9 | GCSF 10 | GMCSF 11 |
| DAY 12 PRESENT | | | | | | | | | | | |
| CD43 | 3.2% | 3.0% | 4.0% | 4.0% | 3.2% | 2.4% | 2.3% | 3.0% | 3.2% | 2.3% | 3.0% |
| CD31 | 2.6% | 2.4% | 3.2% | 3.2% | 2.6% | 1.8% | 1.7% | 2.4% | 2.5% | 1.8% | 2.4% |
| CD45 | 2.4% | 2.7% | 3.7% | 3.6% | 2.4% | 1.5% | 1.5% | 2.7% | 2.4% | 1.5% | 2.6% |
| CD34 | 2.6% | 2.6% | 2.9% | 2.9% | 2.7% | 2.0% | 2.2% | 2.3% | 2.6% | 2.0% | 2.4% |
| FLK-1 | 0.6% | 0.5% | 0.7% | 0.6% | 0.6% | 0.2% | 0.3% | 0.4% | 0.5% | 0.4% | 0.4% |
| ABSENT | | | | | | | | | | | |
| CD43 | 1.2% | 1.4% | 0.3% | 0.2% | 1.2% | 2.1% | 2.2% | 1.4% | 1.2% | 2.3% | 1.4% |
| CD31 | 1.3% | 1.5% | 0.6% | 0.6% | 1.3% | 2.2% | 2.3% | 1.6% | 1.4% | 2.2% | 1.5% |
| CD45 | 1.5% | 1.2% | 0.1% | 0.2% | 1.5% | 2.6% | 2.6% | 1.3% | 1.5% | 2.6% | 1.3% |
| CD34 | 1.7% | 1.7% | 1.3% | 1.3% | 1.6% | 2.4% | 2.2% | 2.0% | 1.7% | 2.4% | 1.9% |
| FLK-1 | 0.3% | 0.5% | 0.2% | 0.3% | 0.4% | 0.8% | 0.7% | 0.6% | 0.5% | 0.7% | 0.6% |
| DAY 17 PRESENT | | | | | | | | | | | |
| CD43 | 9.8% | 12.4% | 12.8% | 12.6% | 9.7% | 9.1% | 9.2% | 12.1% | 9.9% | 9.1% | 12.1% |
| CD31 | 9.3% | 11.5% | 11.9% | 11.8% | 9.4% | 8.8% | 8.6% | 11.2% | 9.4% | 8.6% | 11.3% |
| CD45 | 9.6% | 12.3% | 12.8% | 12.7% | 9.4% | 8.9% | 8.8% | 12.2% | 9.6% | 8.8% | 12.3% |
| CD34 | 2.6% | 2.6% | 2.9% | 2.8% | 2.7% | 2.4% | 2.4% | 2.4% | 3.0% | 2.2% | 2.8% |
| FLK-1 | 2.2% | 2.4% | 2.7% | 2.3% | 2.1% | 2.1% | 2.0% | 2.4% | 2.5% | 2.1% | 2.3% |
| ABSENT | | | | | | | | | | | |
| CD43 | 4.1% | 1.1% | 0.7% | 0.9% | 4.2% | 5.0% | 4.8% | 1.4% | 4.1% | 4.9% | 1.4% |
| CD31 | 3.9% | 1.4% | 1.0% | 1.0% | 3.9% | 4.6% | 4.8% | 1.8% | 3.8% | 4.8% | 1.6% |
| CD45 | 4.0% | 0.9% | 0.3% | 0.4% | 4.2% | 4.8% | 4.9% | 1.0% | 4.1% | 4.9% | 0.9% |
| CD34 | 2.3% | 2.2% | 2.0% | 2.0% | 2.1% | 2.5% | 2.5% | 2.5% | 1.8% | 2.7% | 2.1% |
| FLK-1 | 1.4% | 1.3% | 0.8% | 1.4% | 1.5% | 1.6% | 1.7% | 1.2% | 1.1% | 1.6% | 1.4% |

Out of the 11 cytokines in the EB cytokine mix, a set of 5 cytokines (BMP4, VEGF, IL-3, Flt-3, GMCSF) was identified to be particularly effective or essential to drive the serum free hematopoietic differentiation protocol. Of the five cytokines BMP-4 and VEGF appeared to play a significant role at all time points role during EB differentiation while GMCSF and IL-3 seemed to play a role during later stages of EB differentiation.

Colony formation assays were performed at the end of each time point of hematopoietic differentiation. The CFU assays revealed that a 5 cytokine combination yielded comparable number of total colonies as the 11 cytokine cocktail at all time points. The frequency of GEMM colonies (3-5 per $10^5$ cells) were comparable between 11 cytokine and 5 cytokine combinations at day 12 of EB differentiation. The EB differentiation medium containing 5 cytokines was used to successfully generate hematopoietic precursor cells from hESCs and iPSCs.

The EB differentiation medium containing 5 cytokines was sufficient to generate hematopoietic precursor cells from hESCs and iPSCs. hESCs and iPSCs adapted to feeder free growth on Matrigel™ maintained using mTESR were preconditioned for three days in the presence of mTesR-GF or X-vivo 15 containing 0.1 ng/ml TGF-β and 20 ng/ml FGF-2

Determining Concentrations for the Cytokines Used for Hematopoietic Differentiation Experimental Protocol: hESCs adapted to feeder free growth on matrigel maintained using mTESR were preconditioned for three days in the presence of mTeSR-GF containing 0.1 ng/ml TGF-β and 20 ng/ml FGF-2. Cells were harvested using TrypLE™ for 6 minutes at 37 C. TrypLE™ was neutralized using EB basal media containing 1 μM ROCK inhibitor, and soybean trypsin inhibitor (0.25 mg/ml). The cells were washed once in EB basal media containing 1 μM ROCK inhibitor (H-1152), Soybean trypsin inhibitor (0.25 mg/ml). The cells were plated in low attachment plates in EB basal media containing 1 μM ROCK inhibitor, soybean trypsin inhibitor (0.25 mg/ml) at a cell density of 1 million cells per ml. The media was changed the next day to EB basal media containing 5 cytokines at different concentrations. The concentration of cytokines used is as follows: BMP-4, VEGF, SCF, FLT-3 ligand ranged between 50-25 ng/ml; IL-3, GM-CSF ranged between 10-20 ng/ml.

The EB cultures were half fed with fresh differentiation media every two days. The EB cultures were harvested on days 9 and 12 of differentiation. The EB cultures were harvested by spinning down all the cells and digesting the EBs with TrypLE™ or 0.5% trypsin. The phenotype of the progenitor cell types was analyzed by flow cytometry and the cells were plated in methylcellulose media for CFU assays.

Results (5 Cytokine Dose Matrix)

The results indicate that the approximate optimum dose of five essential cytokines driving the generation of hematopoietic precursor cells is 25 ng/ml of BMP4, VEGF, and Flt-3 ligand and 10 ng/ml for IL-3 and GMCSF. This combination of cytokines is capable of generating hematopoietic precursors generating multipotent GEMM colonies (3-5 per $10^5$ cells) at day 12 of EB differentiation.

Reaggregation of EB Cultures Augments Hematopoiesis

The serum-free 12 day EB differentiation protocol was further optimized by including a reaggregation step during the differentiation protocol.

Experimental Protocol: hESCs adapted to feeder free growth on matrigel maintained using mTESR were preconditioned for two days in the presence of mTeSR-GF containing 0.1 ng/ml TGF and 20 ng/ml FGF-2. Cells were harvested using TrypLE for 6 minutes at 37 C. TrypLE™ was neutralized using EB basal media containing 1 μM ROCK inhibitor.

The cells were washed once in EB basal media containing 1 μM ROCK inhibitor, soybean trypsin inhibitor (0.25 mg/ml). The cells were plated in low attachment plates in EB basal media containing 1 μM ROCK inhibitor (H-1152) and soybean trypsin inhibitor (0.25 mg/ml) for 12-24 hrs.

The media was changed the next day to EB basal media containing BMP-4 and VEGF both at 25 ng/ml. The cells were differentiated for 4, 5 or 6 days in the first set of cytokines The EB cultures were subsequently exposed to IL-3/GMCSF/FLT-3 ligand for an additional 4, 5 or 6 days after the first pulse with 2 cytokines During the transition from the first set of cytokines to the other, one set of EBs were digested using TrypLE™ and allowed to reaggregate in the second media, while the other set was placed in the second media without the disaggregation step. Throughout the differentiation process the EB cultures were half fed with fresh differentiation media every two days. The EB cultures were harvested on day 9, 10, 11 and 14 days of EB differentiation. At the end of the experiment EB cultures were harvested by spinning down all the cells and digesting the EBs with TrypLE™ or 0.5% Trypsin. The phenotype of the progenitor cell types was analyzed by flow cytometry and the cells were placed in methyl cellulose for CFU assays.

Results

Partial Reggregation of EB cultures augmented the hematopoietic differentiation. The presence of BMP4 and VEGF for the first 4-5 days followed by the addition of IL-3/Flt3 ligand/GMCSF for the next 7-8 days yielded the highest numbers of hematopoietic precursors (>10%) expressing CD43+, CD34+, CD45+, and CD31+.

The results of the colony forming assays mimicked the data obtained by flow cytometric analysis. The EB cultures pulsed with BMP4 and VEGF for the first 4-5 days followed by the addition of IL-3/FLT3 ligand/GMCSF for the next 7-8 days revealed the highest colony forming units. The total CFU values went up from >100 to up to 250 after the reaggregation step. The frequency of GEMM bearing colonies jumped from 3-5 per $10^5$ to 15-20 per $10^5$ cells.

Example 4

EB Size can Affect Hematopoietic Differentiation hESCs adapted to feeder free growth on matrigel maintained using mTESR were preconditioned for two days in the presence of mTeSR-GF containing 0.1 ng/ml TGF-β and 20 ng/ml FGF-2. Cells were harvested using TrypLE for 6 minutes at 37 C. TrypLE™ was neutralized using EB basal media containing 10 μM Y-27632 ROCK inhibitor, Soybean trypsin inhibitor (0.25 mg/ml). The cells were washed once in EB basal media containing 1 μM ROCK inhibitor, Soybean trypsin inhibitor (0.25 mg/ml).

The viable count of the cells was determined and the desired number of cells was placed in each well of the AggreWell™ plate according to the manufacturer's instructions: $1.2 \times 10^5$ cells were plated to yield a 100 cell aggregate EBs; $2.4 \times 10^5$ cells were plated to yield a 200 cell aggregate EBs; $6 \times 10^5$ cells were plated to yield a 500 cell aggregate EBs; $1.2 \times 10^6$ cells were plated to yield a 1000 cell aggregate EBs; $2.4 \times 10^6$ cells were plated to yield a 2000 cell aggregate EBs; $3.6 \times 10^6$ cells were plated to yield a 2000 cell aggregate EBs; $4.8 \times 10^6$ cells were plated to yield a 2000 cell aggregate EBs.

The cells were plated in AggreWell™ (using the manufacturer's instructions) in EB basal media containing 1 μM ROCK inhibitor (H-1152), soybean trypsin inhibitor (0.25 mg/ml) for 18-24 hr to allow EB formation. The cells were transferred to a low attachment plate and photographs taken to measure the size of the EBs formed using various cell numbers.

Figure 3:
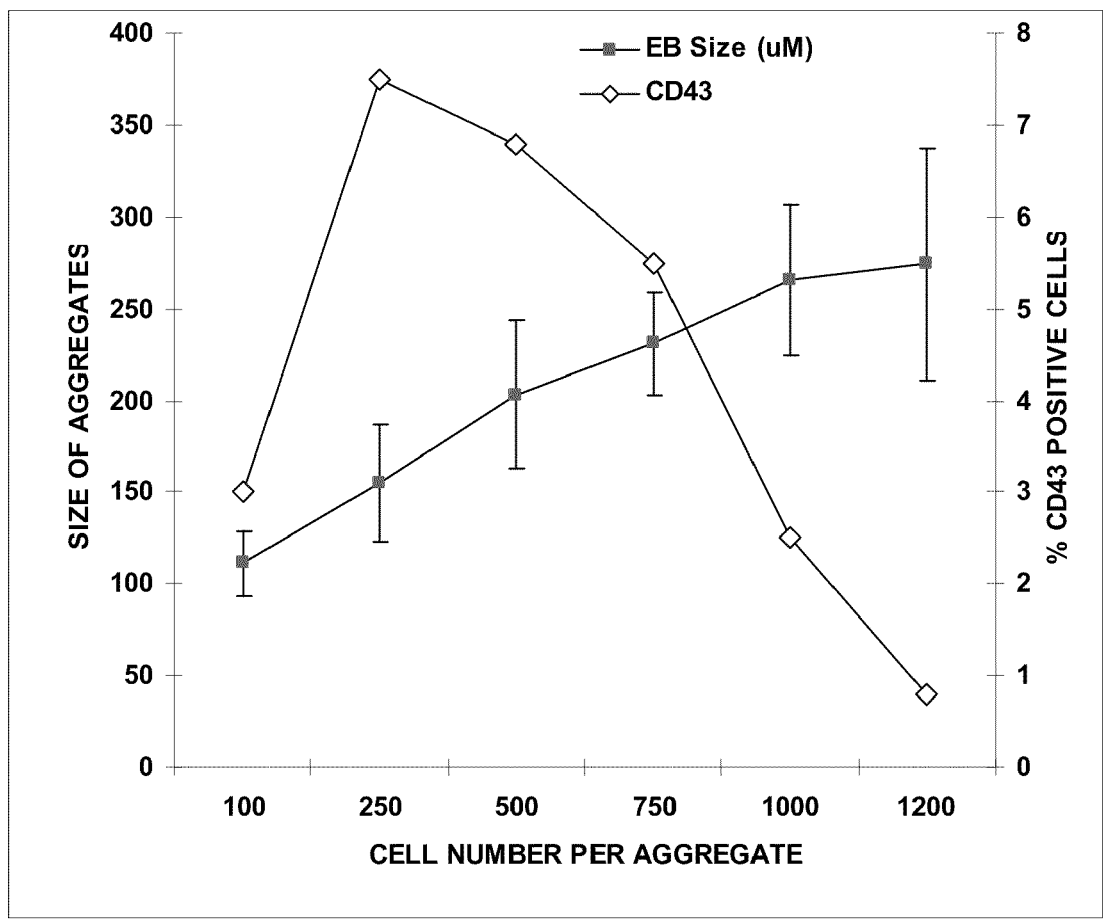
FIG. 3: Embryoid body (EB) size correlates with CD43 expression.
Figure 4:
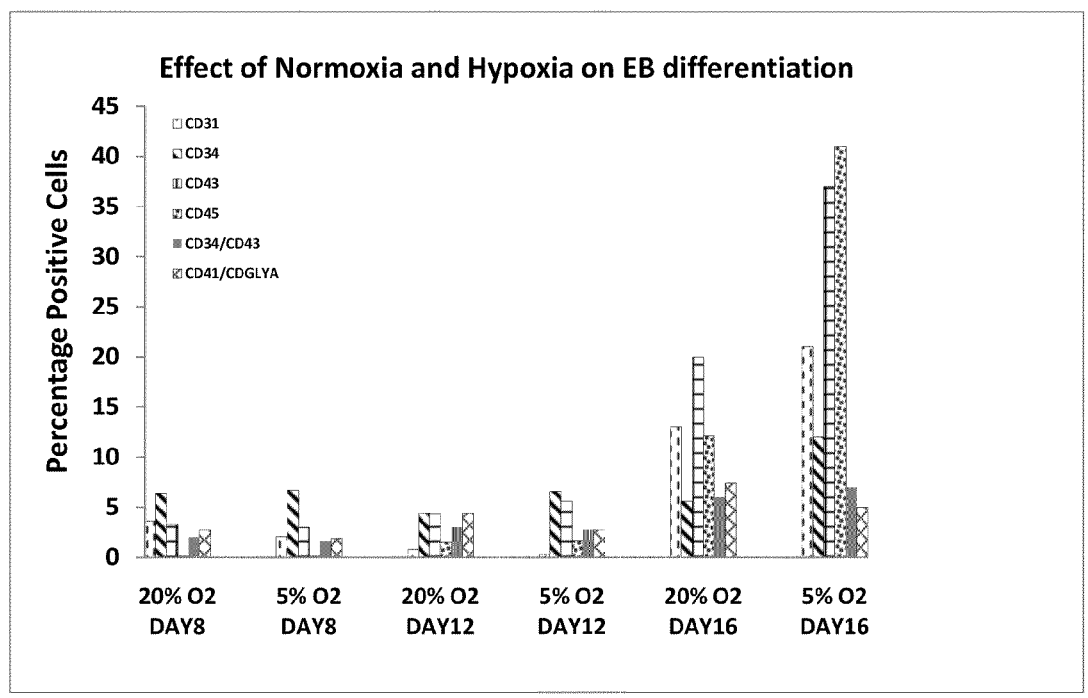
FIG. 4: Hypoxia promotes hematopoietic differentiation.

The EB cultures were differentiated in media containing 5 cytokines (BMP4/VEGF/IL-3/FLT-3 ligand/GMCSF). The EB cultures were half fed with fresh differentiation media containing all five cytokines every two days. The EB cultures were harvested on day 11 of differentiation. At the end of the experiment EB cultures were harvested by spinning down all the cells and digesting the EBs with TrypLE™ or 0.5% Trypsin and the CD43 values were quantified by flow cytometry. As shown in FIG. 3, a correlation between EB size and CD43 expression was observed.

H1 hESC aggregates containing definite cell numbers were formed in AggreWell™ plates (Stem cell technologies using the manufacturer's instructions) in EB basal media for 18-24 hrs. The cells were later transferred to a low attachment plate and EB size generated by different cell numbers in μM was recorded using the scale bar on the microscope. The cell number comprising the EB and aggregate size of EBs was quantified before the onset of differentiation. The EBs cultures were differentiated in the presence of BMP4/VEGF/IL-3/FLT-3 ligand/GMCSF for 11 days. At the end of the experiment EB cultures were harvested by individualizing the EBs using TrypLE™ and the CD43 values were quantified by flow cytometry.

Results

The optimum cell number for hematopoietic differentiation is between 200-1000 cells per aggregate measuring between 100-250 μm. Larger cell number aggregates (>2000) measuring greater than 1000 μm did not facilitate the generation of hematopoietic precursor cells.

Example 5

Hypoxic Conditions Augment Hematopoietic Differentiation

H1 hESCs adapted to feeder free growth on matrigel maintained using mTeSR were preconditioned for two days in the presence of mTeSR-GF containing 0.1 ng/ml TGF-β and 20 ng/ml FGF-2. Cells were harvested using TrypLE™ and plated in low attachment plates in EB basal media containing 1 μM ROCK inhibitor (H-1152) and soybean trypsin inhibitor (0.25 mg/ml) at a cell density of one million cells per ml for 12-24 hours.

The EBs cultures were differentiated in media containing 5 cytokines (BMP4/VEGF/IL-3/FLT-3 ligand/GMCSF). The EB cultures were half fed with fresh differentiation media containing all five cytokines every two days. The EB cultures were harvested on day 8, 12 and 16 of differentiation without the reaggregation step. At the end of the experiment EB cultures were harvested by spinning down all the cells and digesting the EBs with TrypLE™ or 0.5% Trypsin and the phenotypic expression of various surface markers associated with hematopoiesis was quantified by flow cytometry.

Results

EB cultures yielded a higher percentage of CD43, CD31, CD45, CD34 expressing cells under low oxygen conditions when compared to high oxygen conditions. The effect was more pronounced after 8 days of EB differentiation. The total cell number was comparable under both conditions.

H1 hESCs adapted to feeder free growth on matrigel coated plates were preconditioned for 2 days using mTeSR-GF supplemented with 0.1 ng/ml TGF-β and 20 ng/ml FGF-2, The cells were harvested using TrypLE™ in the presence of a ROCK inhibitor. The EBs were transferred to EB differentiation media containing VEGF, BMP4, IL-3, GMCSF, and Flt-3 ligand under low (5% $O_2$) and high (20% $O_2$) oxygen conditions. The cells were harvested on day 8, 11 and 16 days of differentiation and the phenotype of the cells was quantified by flow cytometry.

Efficiency of Generating Hematopoietic Precursors

H1 hESCs and iPSCs adapted to feeder free growth on Matrigel™ maintained using mTeSR™ were preconditioned for two days in the presence of mTeSR-GF containing 0.1 ng/ml TGF and 20 ng/ml FGF-2. Cells were harvested using TrypLE™. The viable cell count was estimated and the cells were plated at a density of one million cells per ml.

The cells were plated in low attachment plates in EB basal media containing 1 µM ROCK inhibitor (H-1152) and soybean trypsin inhibitor (0.25 mg/ml) for 24 hours. The EBs cultures were induced to differentiate in a two step differentiation process. The cultures were placed in media containing BMP4 and VEGF for 4 days under hypoxic conditions. The EB cultures were reaggreggated using TrypLE on day 5 of differentiation and placed in the second differentiation medium with either (1) IL-3, FLT-3 ligand, GMCSF; (2) IL-3, FLT-3 ligand, SCF; or (3) IL-3, FLT-3 ligand, TPO for an additional 7 days under hypoxic conditions. The EB cultures were half fed with fresh differentiation media every two days. The EB cultures were harvested on day 12 of differentiation. At the end of the experiment, EB cultures were harvested by spinning down all the cells and digesting the EBs with TrypLE™ or 0.5% trypsin. The total viable cell count at the end of the experiment was estimated. The phenotypic expression of various surface markers associated with hematopoiesis was quantified by flow cytometry. The percentage and the absolute number of hematopoietic precursor cells (CD43+/CD34+) was quantified. Thus, the efficiency of generation of hematopoietic precursor cells was determined by dividing the initial cell count by the number of hematopoietic precursors generated at the end of the differentiation experiment.

Figure 5:
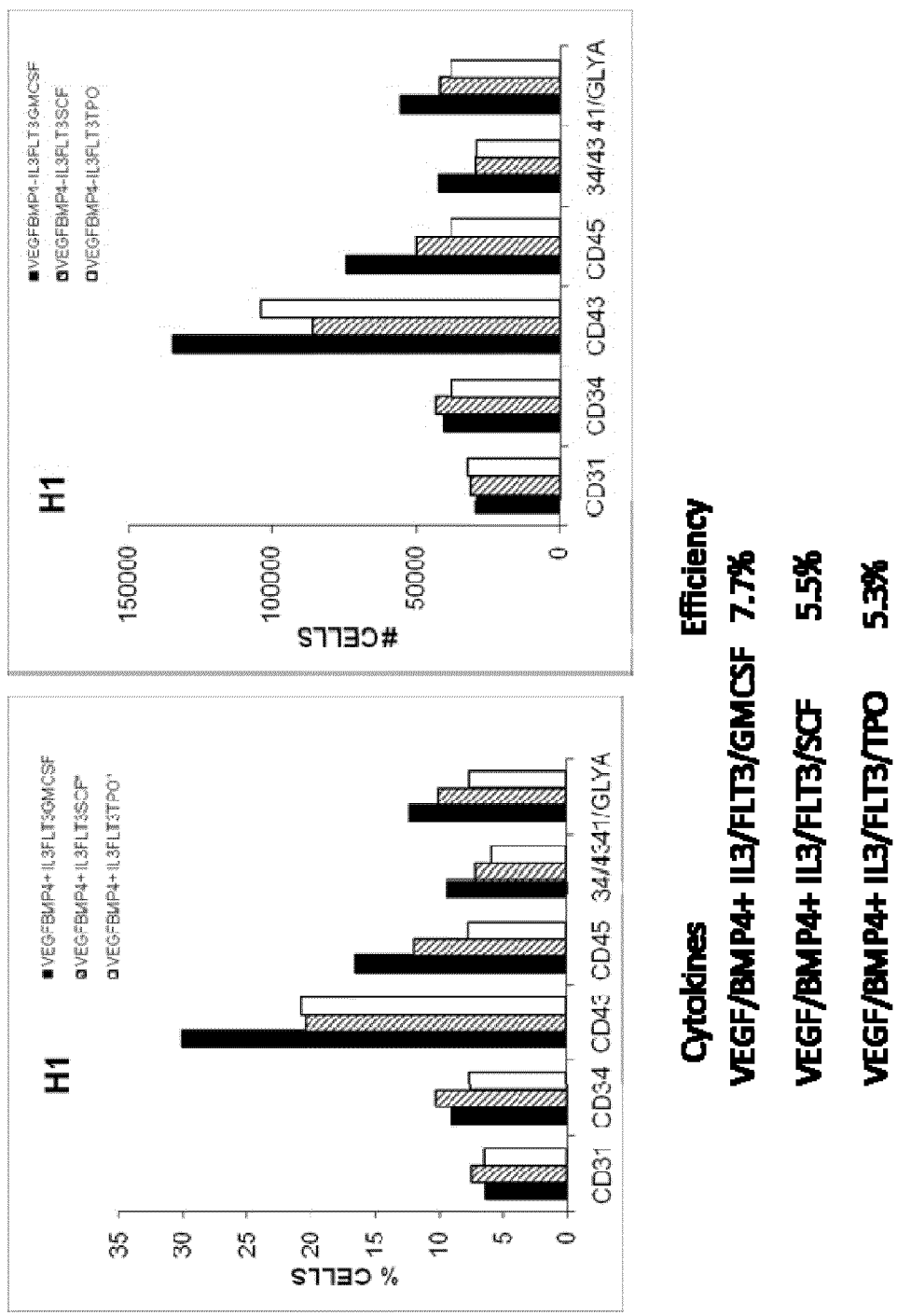
FIG. 5: Efficiency of generation of hematopoietic precursor cells from single cell suspensions of pluripotent cells.

Result: The efficiency of generating a hematopoietic precursor population using the 2 step EB differentiation protocol from hESCs and iPSCs was observed to be between 5-8%. Results are shown in FIG. 5.

Example 6

Scale-Up of EB Differentiation Protocol Using Spinner Flasks

Hematopoietic precursor cells generated using the above EB differentiation protocol were found to be capable of generating erythroid precursors, megakaryocytes, macrophages, monocytes, and dendritic cells. Specifically, H1 hESCs and iPSCs adapted to feeder free growth on matrigel maintained using mTESR were preconditioned for two days in the presence of mTeSR-GF containing 0.1 ng/ml TGF and 20 ng/ml FGF-2. Cells were harvested using TrypLE The viable cell count was estimated for all cell lines.

The cells were plated at a cell density of one million cells per ml in low attachment plates in EB basal media containing 1 µM ROCK inhibitor (H-1152) and soybean trypsin inhibitor (0.25 mg/ml) for 24 hours. The EBs cultures were induced to differentiate in a two step differentiation process. The cultures were placed in media containing BMP4 and VEGF for 4 days. The EB cultures were reaggreggated on day 5 TrypLE and placed in the second differentiation medium with either (1) IL-3, FLT-3 ligand, GMCSF; (2) IL-3, FLT-3 ligand, SCF, or (3) IL-3, FLT-3, TPO for an additional 7 days. The EB cultures were half fed with fresh differentiation media every two days. The entire 12 day differentiation was performed under hypoxic conditions. The EB cultures were harvested on day 12 of differentiation. At the end of the experiment EB cultures were harvested by spinning down all the cells and digesting the EBs with TrypLE™ or 0.5% trypsin. The total cell count at the end of the experiment was estimated. 1 million hESC were capable of generating 80,000 hematopoietic precursor cells.

The precursors derived from IL-3, FLT-3 GMCSF set (1) was placed for 8 days in media containing 200 ng/ml GMCSF. These cells were further differentiated into: (1) macrophages by placing the cells in M-CSF (10 ng/ml) and IL-1β (20 ng/ml) containing media for 2 weeks, or (2) dendritic cells by placing the cells in media containing 20 ng/ml GMCSF and 20 ng/ml IL-4. One million hESCs were capable of generating 0.2 million dendritic cells. All lineage differentiation experiments were performed at a non-hypoxic (~20%) oxygen concentration.

Megakaryocytes were produced by placing the precursor cells derived from IL-3, FLT-3 ligand, SCF set (2) in media MK3 containing (100 ng/ml, TPO, SCF, FLT-3, 20% BIT9500). Mast Cells were produced by expanding the precursor in MK3 expansion followed by 5 ng/ml SCF, 5 ng/ml IL-6 containing media. One million hESCs were capable of generating 0.06-1.2 million megakaryocytes. The lineage differentiation experiments were performed at a non-hypoxic (~20%) oxygen concentration.

Erythroid progenitors were generated by placing the precursor derived from IL-3, FLT-3 SCF TPO in media containing hydrocortisone (10-6M) holotransferrin, ExCyte. The lineage differentiation experiments were performed under normoxic (~20% oxygen) conditions. Supplementation of human AB serum and Hypoxic conditions augmented the yield of erythroid progenitors. These methods were used to expand million hESCs to around 100 million erythroblasts in culture.

Cells were first preconditioned prior to differentiation. Undifferentiated hESC's and iPSC's adapted to feeder free growth on Matrigel coated plates were separately preconditioned for 24 hours using TeSR without growth factors supplemented with 0.1 ng/ml TGF and 20 ng/ml zebrafish FGF.

The cells were harvested at confluence using TrypLE™ treatment for 5 minutes at 37° C. The cells were collected in EB basal media containing IMDM supplemented with 20% BIT9500 (Stem Cell Technologies), or serum replacer 3 (Sigma Aldrich), 1% NEAA, 1 mM L-glutamine, and 0.1 mM mercaptoethanol (all from Invitrogen, Carlsbad, Calif.), 0.75% BSA, 50 µg/ml ascorbic acid, and 1 µM ROCK inhibitor (H-1152).

The cells were then placed in 125 ml Corning spinner flasks at a density of 0.5-2 million cells per ml. The spinners were set to 30-40 rpm overnight to facilitate EB formation. Alternately the cells may be placed in low attachment corning flasks under static conditions for 24 hours in low attachment plates. Improved survival of the cells were observed when cells were cultured for the first 12-24 hours. After 12-24 hrs the cells were placed in EB differentiation media containing cytokines without the ROCK inhibitor on a magnetic stir platform in a spinner flask with a speed of 60 RPM. EB were generated when the spinner flasks were maintained at 25-30 RPM for the first 12-24 hours and then increased to 40-60 for subsequent differentiation. The side caps of the spinner flasks were loosened to allow gas transfer. The cells were placed in EB basal media supplemented with 50 ng/ml bone morphogenetic factor (BMP-4), 50 ng/ml, vasular endothelial growth factor (VEGF), and 25 ng/ml zebrafish FGF-2.

On the fourth day of differentiation, the cells were fed cells by setting the spinner flask in cell culture hood to allow suspended EB aggregates to settle to the bottom of the flask for 15-20 minutes. The spent media was aspirated (with approximately 20 mL left for 125 ml spinner). The cells were gently swirled and fresh media containing 50 ng/ml bone morphogenetic factor (BMP-4), 50 ng/ml, vasular endothelial growth factor (VEGF), and 25 ng/ml zebrafish FGF-2 was added to the cells. The spinner flasks were set to a speed of 60 rpm throughout the entire process of hematopoietic differentiation.

On day 5-6 of differentiation, the spent media was aspirated as described above and the cells were placed in EB basal media supplemented with either: (1) 25 ng/ml of Flt-3 ligand, 10 mg/ml of IL-3 and 10 ng/ml GMCSF, or (2) with 25 ng/ml of Flt-3 ligand, 25 ng/ml of SCF, 25 ng/ml of TPO, 10 ng/ml IL-3, and 10 ng/ml IL-6. The spent media was aspirated on day 8 and 10 as described above.

Figure 6:
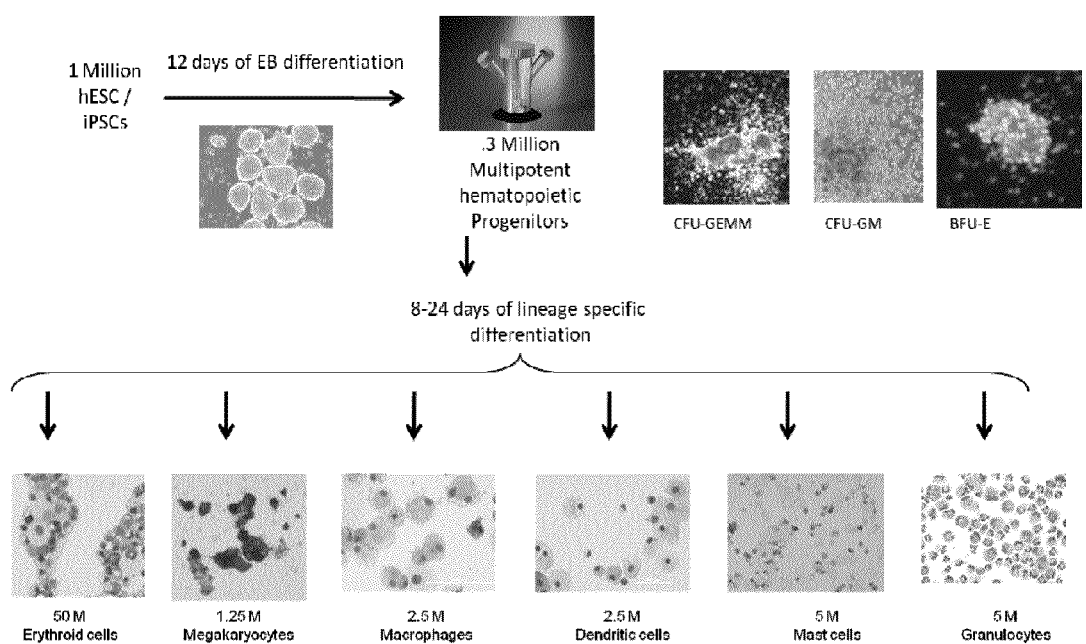
FIG. 6: Overview of EB differentiation and generation of HPCs and various lineage specific cell types using spinner flasks.

The EB cultures were harvested on day 12 of differentiation. The total cell number was quantified at the end of the analysis. The cells were stained for the phenotypic expression of surface markers (CD34+, CD45+, CD43+, CD41+, CD235a+, CD31+) to quantify the hematopoietic progenitor content of the population. Table 5 summarizes the spinner data generated with varying cell densities using H1 ES cells. Similar results were obtained with iPS cells. An outline of the EB differentiation process in spinner flasks, and results obtained, is shown in FIG. 6. The hematopoietic progenitors were capable of generating various cell types belonging to different lineage, including erythroblasts, megakaryocytes, dendritic cells, mast cells, granulocytes and macrophages.

ng/ml, vasular endothelial growth factor (VEGF), and 25 ng/ml zebrafish FGF-2. Around 300 µl of media was used per well of a 96 well plate.

On day 3-4 of differentiation the cells were half fed by gently removing half the volume of spent media (between 100-150 µl) and equal volume of fresh media containing 50 ng/ml bone morphogenetic factor (BMP-4), 50 ng/ml vasular endothelial growth factor (VEGF), and 25 ng/ml zebrafish FGF-2 was added to the cells.

On day 5-6 of differentiation the spent media was aspirated as described before and the cells were placed in EB basal media supplemented with either: (1) 25 ng/ml of Flt-3 ligand, 10 mg/ml of IL-3 and 10 ng/ml GMCSF, or (2) media containing 25 ng/ml of Flt-3 ligand, 25 ng/ml of SCF, 25 ng/ml of TPO, 10 ng/ml IL-3, and 10 ng/ml IL-6. The differentiating EB cultures were half fed with fresh media on day 8 and 10 of differentiation as described above.

The EB cultures were harvested on day 12 of differentiation. The total cell number was quantified at the end of the analysis. The cells were stained for the phenotypic expression of surface markers (CD34+, CD45+, CD43+, CD41+, CD235a+, CD31+) to quantify the hematopoietic progenitor content of the population. The data generated using H1 ES cells is summarized in FIG. 7. Similar results were obtained using iPS cells.

Figure 7:
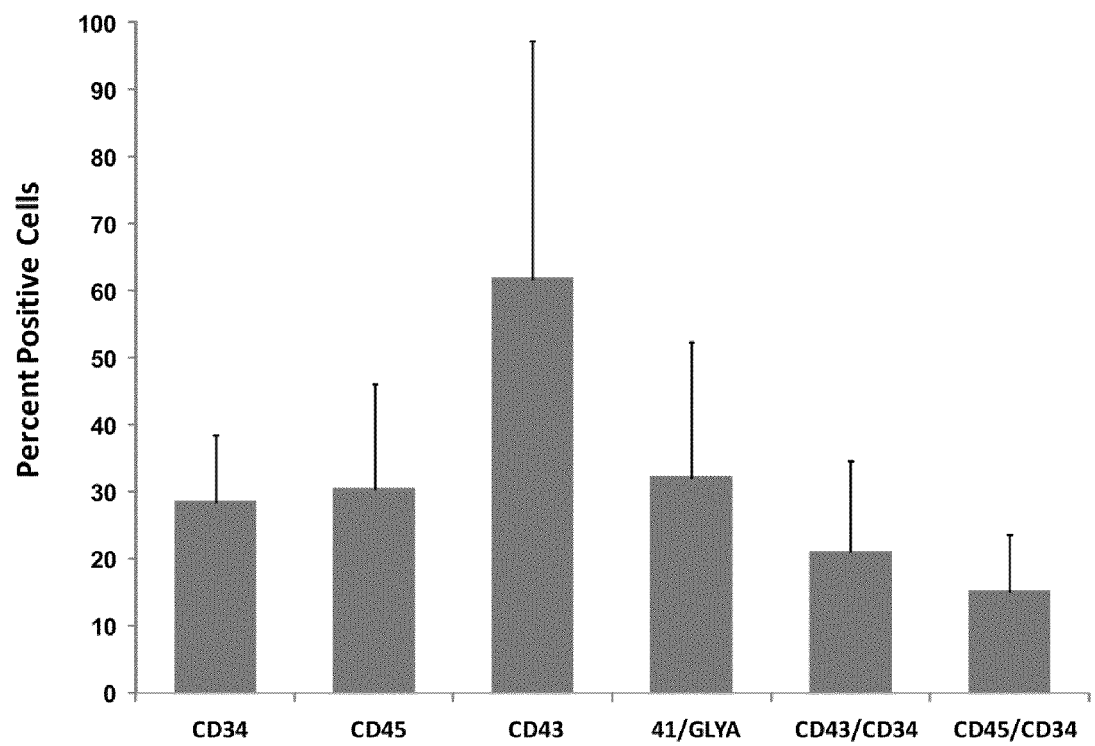
FIG. 7: EB differentiation of hESCs in a 96 well format.

As shown in FIG. 7, 100000 cells were plated on low attachment 96 well plates. The cells were differentiated in the presence of cytokines (BMP4/VEGF/FGF) under hypoxic (5% O2) conditions for the first 4-5 days, and in the presence of cytokines (SCF/FLt-3/TPO/IL-3/IL-6) under hypoxic (5% O2) conditions for the next 7-8 days of differentiation. The

TABLE 5

| Cell Density | Starting Cell Number | EB 12 yield | Repeats | HPC (CD34+ CD43)+ | CD45 | Glya/CD41 | CD43 | CD34 | Absolute HPC Yield | Efficiency |
|---|---|---|---|---|---|---|---|---|---|---|
| 0.5 million cells per ml | 30 million | 52 million | n = 1 | 8% | 7% | 6.50% | 18% | 15% | 4.16 million cells | 17.33333 |
| 1 million cells per ml | 60 million | 140 million | n = 2 | 15% | 13% | 10% | 30% | 25% | 21 million cells | 35 |
| 2 million cells per ml | 120 millon | 160 million | n = 2 | 9% | 8% | 6% | 20% | 15% | 16 million cells | 13.33333 |
| 3 million cells per ml | 180 million | 80 million | n = 1 | 5% | 2.50% | 3.50% | 10% | 8% | 4 million cells | 2.22222 |
| 5 millon cells per ml | 300 millon | 50 million | n = 1 | 2% | 1% | 2% | 7% | 5% | 1 million cells | 2 |

Example 7

Miniaturization of EB Differentiation Using 96-Well Plates

Undifferentiated hESC's and iPSC adapted to feeder free growth on Matrigel coated plates were separately preconditioned for 24 hours using TeSR without growth factors supplemented with 0.1 ng/ml TGF and 20 ng/ml zebrafish FGF. The cells were harvested at confluence using TrypLE treatment for 5 minutes at 37 C. The cells were collected in EB basal media containing IMDM supplemented with 20% BIT9500 (Stem Cell Technologies) or Serum Replacement-3 (Sigma Aldrich), 1% NEAA, 1 mM L-glutamine, and 0.1 mM mercaptoethanol (all from Invitrogen, Carlsbad, Calif.), 0.75% BSA, 50 µg/ml ascorbic acid, and 1 µM ROCK inhibitor (H-1152).

The cells were placed in low attachment 96 well plates at a density of 0.1 million cells per well in EB basal containing the ROCK inhibitor. EB formation was facilitated by incubating the plated cells under hypoxic (5% $O_2$) conditions. After 12-24 hrs the cells were placed in EB differentiation media containing 50 ng/ml bone morphogenetic factor (BMP-4), 50 cells were harvested after 12 days of differentiation and the HPCs were quantified by flow cytometry.

Example 8

Robotic Automation

Conditions for the maintenance and generating hematopoietic precursor cells using the Tecan Cellerity system (an industrially relevant robotic platform). Based on the protocol used in Example 8, on day 12 of differentiation the cells were harvested by the Tecan Cellerity system and washed manually for cell surface staining of markers. Post staining, the cells were analyzed using the Hypercyt connected to the Accuri flow cytometer.

Example 9

Generation of Endothelial Cells from Pluripotent Cells

Undifferentiated hESC's and iPSC's adapted to feeder free growth on Matrigel coated plates were separately preconditioned for 24 hours using TeSR without growth factors supplemented with 0.1 ng/ml TGF-β and 20 ng/ml zebrafish FGF-2. The cells were harvested at confluence using TrypLE treatment for 5 minutes at 37° C. The cells were collected in EB basal media containing IMDM supplemented with 20% BIT9500 (Stem Cell Technologies) or Serum Replacement-3 (Sigma Aldrich), 1% NEAA, 1 mM L-glutamine, and 0.1 mM mercaptoethanol (all from Invitrogen, Carlsbad, Calif.), 0.75% BSA, 50 µg/ml ascorbic acid, and 1 µM ROCK inhibitor (H-1152). The cells were placed in low attachment plated to facilitate EB formation at density of 1-2 million cells per ml.

To induce EB differentiation, the following protocol was used. After 12-24 hrs the cells were collected from the plates and spun down at 1000 rpm for 5 minutes. The cells were resuspended in EB basal media supplemented with 50 ng/ml bone morphogenetic factor (BMP-4), 50 ng/ml vasular endothelial growth factor (VEGF), and 50 ng/ml zebrafish FGF-2.

On the fourth day of EB differentiation, the cells were allowed to settle by tilting the plates. Half the supernatant media was aspirated and the replaced with fresh differentiation medium containing 50 ng/ml vasular endothelial growth factor (VEGF), and 50 ng/ml zebrafish FGF-2 respectively.

On the seventh day of EB differentiation, the EB cultures were placed in endothelial differentiation medium (Lonza catlalog #CC3202, Basel, Switzerland) containing VEGF, FGF, EGF, IGF, ascorbic acid and FBS; or fresh differentiation medium containing 50 ng/ml vasular endothelial growth factor (VEGF), and 50 ng/ml zebrafish FGF-2.

Figure 8:
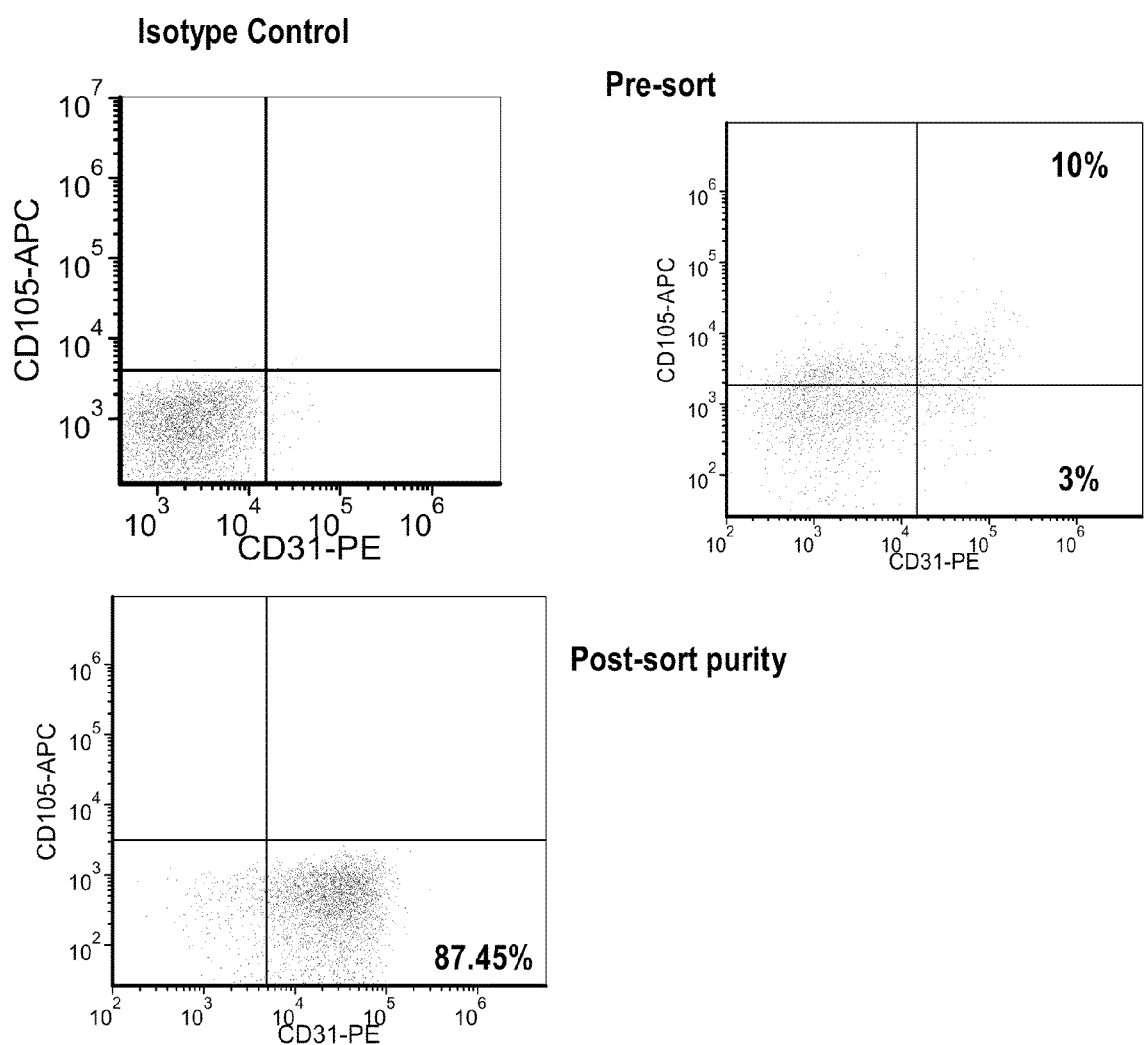
FIG. 8: Representative flow cytometric analysis pre- and post-magnetic sorting of endothelial cells derived from iPSCs.

The cells were analyzed for the presence of endothelial cells on day 10 of differentiation. Cells were collected and spun down in conical tubes. The cell pellet was digested using TrypLE™ select or 0.5% Trypsin for 5 minutes in a 37° C. The cells were resuspended in PBS-FBS containing FACS buffer and the cell count and viability status was determined. The cells were stained with fluorochrome-conjugated monoclonal antibodies anti-human CD31 (WM-59) and anti-human CD105. Non-viable cells were excluded with propidium iodide (50 µg/ml). Live cell analysis was performed on a FACSCalibur™ or Accuri™ flow cytometer. FIG. 8 illustrates the generation of CD31+ cells at 10 days of EB differentiation.

Purfication of endothelial cells: EBs were dispersed into single cell suspensions and purified using anti-CD31 MicroBeads (Milenyi catalog #130-091-935) according to manufacturer's instructions. The resulting population post-magnetic sorting yielded a purified population of (CD31+ CD105+) endothelial cells. The endothelial cells were tested for the uptake of acetylylated LDL, expression of von Willebrand Factor Staining and matrigel tube formation assay. The matrigel tube formation assay indicated the successful generation of endothelial cells derived from iPSC's.

Example 10

Inclusion of FGF-2 in the EB Differentation Media can Increase Efficiency of Hematopoietic Precursor Cell Differentiation Differentiation of hESC and iPSC were separately evaluated under the following conditions. Cells were preconditioned for 1 day in TeSR without growth factors supplemented with 0.1 ng/ml TGF-β and 20 ng/ml FGF-2. EBs were made in EB basal media (IMDM supplemented with 20% BIT-9500, 0.75% BSA, 50 µg/ml acsorbic acid, glutamine, NEAA and 0.1 mM monothioglycerol) supplemented with 1 µM ROCK inhibitor at a cell density of one million cells per ml.

At 12-24 hours later, the cells were placed in one of the following modified EB differentiation media: (A) 25 ng/ml BMP4, 25 ng/ml VEGF, 0 ng/ml FGF-2; (B) 25 ng/ml BMP4, 25 ng/ml VEGF, 10 ng/ml FGF-2; (C) 50 ng/ml BMP4, 50 ng/ml VEGF, 25 ng/ml FGF-2. The EB cultures were half fed every four days throughout the differentiation process. The EB cultures were partially reaggregated between days 4-5 of differentiation. The EB cultures were then placed in media containing 25 ng/ml FLt-3 ligand, 10 ng/ml IL-3 and 10 ng/ml of GMCSF. The EB cultures were half fed every four days throughout the differentiation process The EB cultures were harvested on day 12 of differentiation, and the percentages of expression of CD34, CD43, CD45, CD31, CD41, and CD235a (Gly-a) were quantified. The efficiency of HPC generation was determined by dividing the absolute number of CD34+/CD43+ double positive cells on day 12 of EB differentiation by the starting number of ES/iPS cells.

Figure 9:
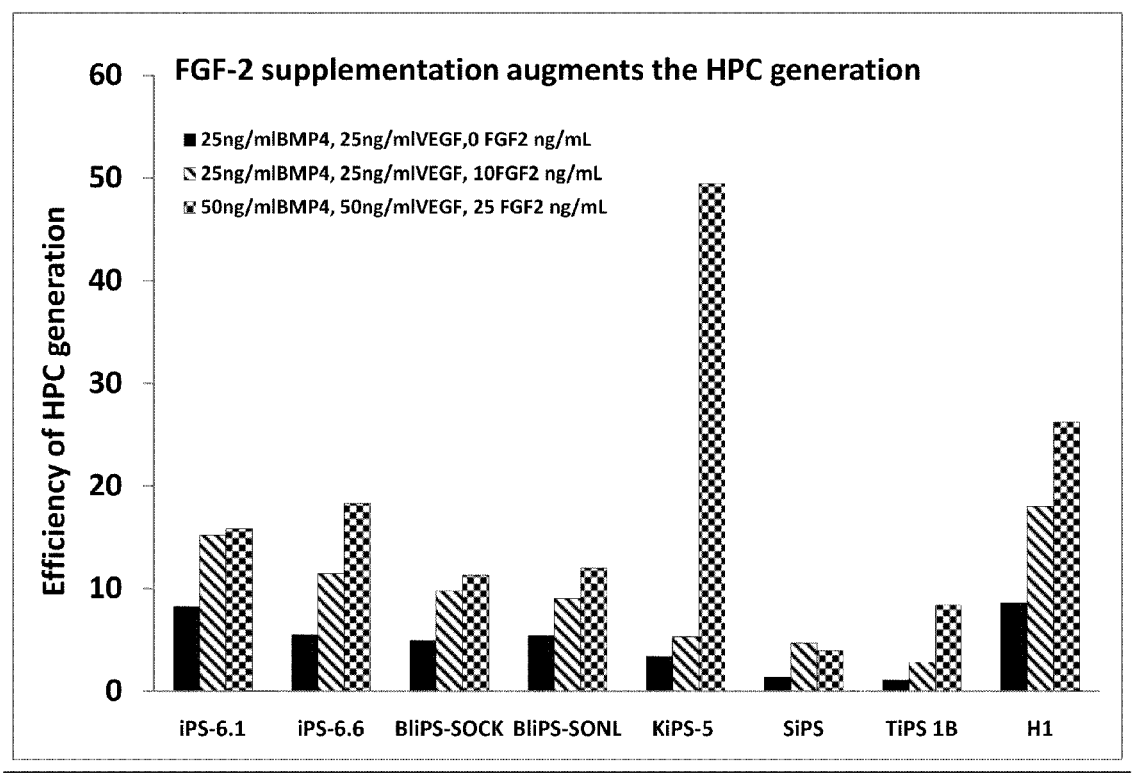
FIG. 9: FGF-2 supplementation in EB differentiation media resulted in increased generation of hematopoietic precursor cells (HPC) in hESC(H1) and various iPSC cell lines.
Figure 10:
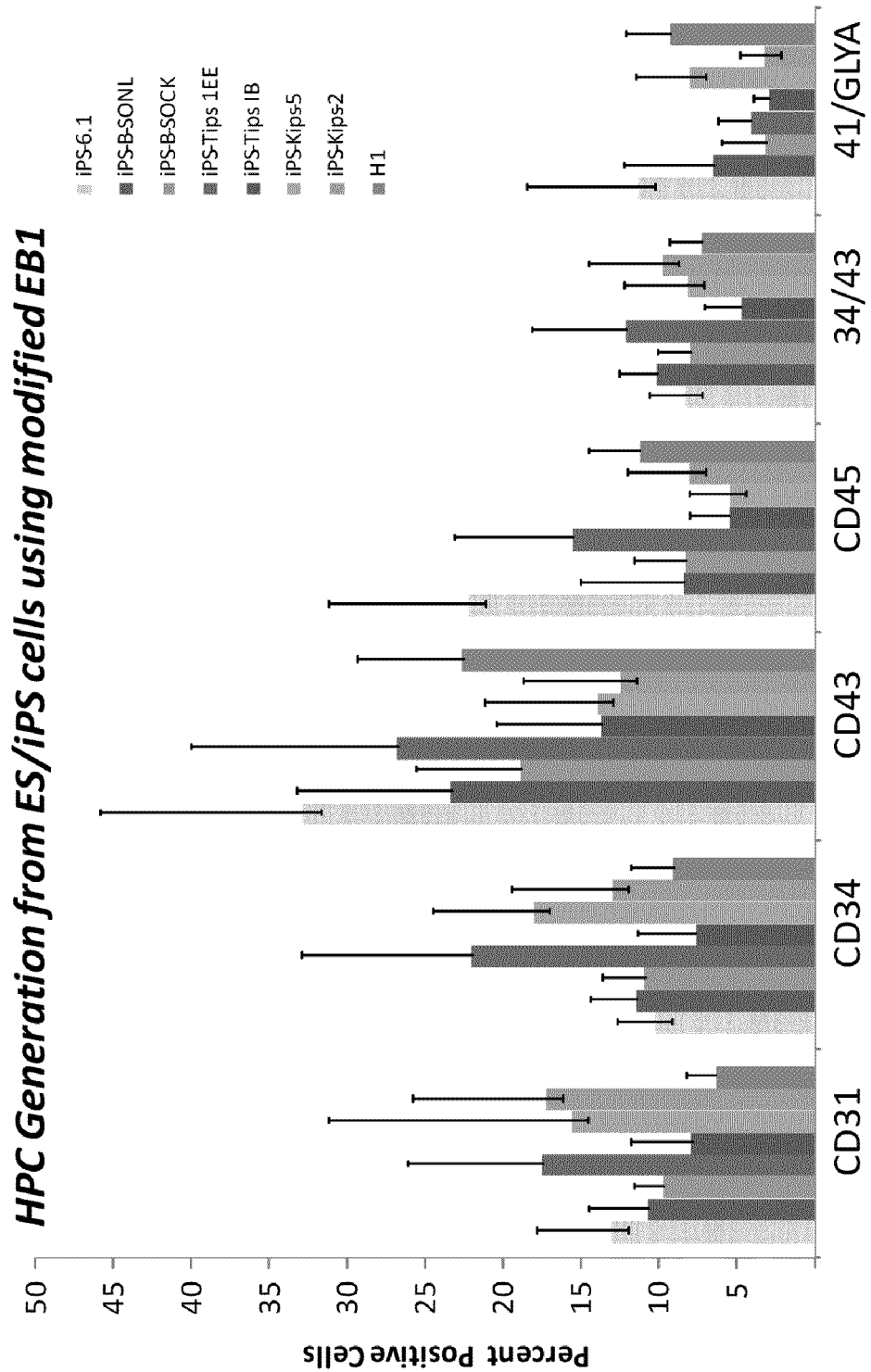
FIG. 10: Differentiation of various iPS cell lines in the presence of EB differentiation medium containing (50 ng/ml BMP4, 50 ng/ml VEGF and 25 ng/ml of FGF-2).

Result: Supplementation of FGF-2 in EB1 differentiation increased the efficiency of the process from 6 to 12% for in iPSC (iPS—SONL) and from 8 to 21% in hESC (H1 ES cells). FIG. 9 summarizes the increase in efficiency with FGF supplementation in hESC (H1) and iPSC(SONL) cell lines. FIG. 10 shows the overall differentiation of various iPS cell lines in the presence of modified EB1 medium containing (50 ng/ml BMP4, 50 ng/ml VEGF and 25 ng/ml of FGF-2).

Example 11

Inclusion of TPO, IL-6, and IL-3 in EB Differentiation Media hESC and iPSC were separately preconditioned for 1 day in TeSR without growth factors supplemented with 0.1 ng/ml TGF-β and 20 ng/ml FGF-2. EBs were generated by next culturing cells in EB basal media (IMDM supplemented with 20% BIT-9500, 0.75% BSA, 50 µg/ml of acsorbic acid, glutamine, NEAA and 0.1 mM monothioglycerol) supplemented with 1 µM ROCK inhibitor (H-1152) a cell density of 1-2 million cells per ml. 12-24 hours later the cells were placed in EB basal media supplemented with 50 ng/ml BMP4, 50 ng/ml VEGF, 25 ng/ml FGF-2. The EB cultures were half fed every four days throughout the differentiation process. The EB cultures were partially reaggregated between days 4-5 of differentiation.

The EB cultures were then cultured in a second EB media ("EB2") which was EB basal media supplemented with either: (A) 25 ng/ml Flt-3 ligand, 10 ng/ml GMCSF, 10 ng/ml IL-3; (B) 100 ng/ml Flt-3 ligand, 100 ng/ml SCF, 100 ng/ml TPO, 10 ng/ml IL-3, 10 ng/ml IL-6; (C) 50 ng/ml Flt-3 ligand, 50 ng/ml SCF, 50 ng/ml TPO, 10 ng/ml IL-3, 10 ng/ml IL-6; or (D) 25 ng/ml Flt-3 ligand, 25 ng/ml SCF, 25 ng/ml TPO, 10 ng/ml IL-3, 10 ng/ml IL-6.

The EB cultures were half fed every four days throughout the differentiation process, and the EB cultures were harvested on day 12 of differentiation. The percentages of cells expressing each of CD34, CD43, CD45, CD31, CD41, and CD235a (Gly-a) were quantified. The efficiency of hematopoietic precursor cell (HPC) generation was determined by dividing the absolute number of CD34+/CD43+ ouble positive cells on day 12 of EB differentiation by the starting number of ES/iPS cells.

Figure 11:
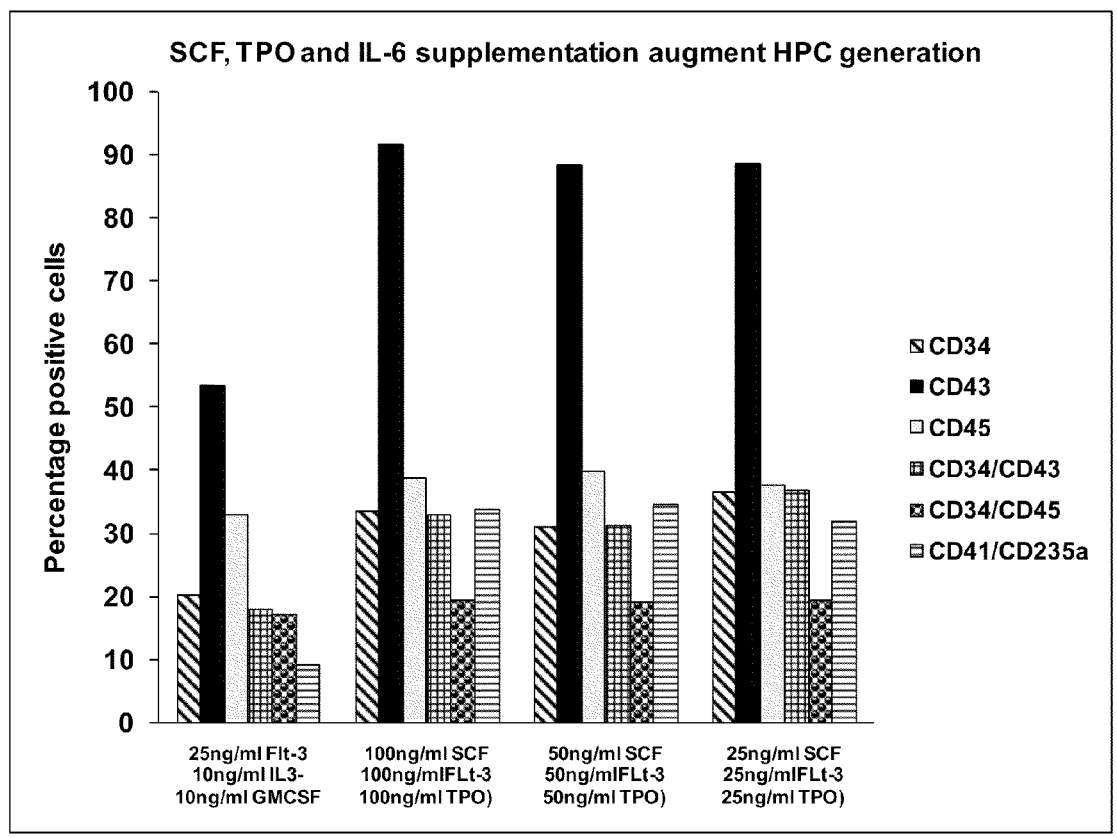
FIG. 11: Differentiation of hESC(H1) and iPS(SONL) cell lines into hematopoietic precursor cells (HPC) is shown using EB basal media supplemented with growth factors. Increased differentiation was observed when the IL-3 and Flt-3 containing media was supplemented with SCF, IL-6 and TPO.
Figure 12:
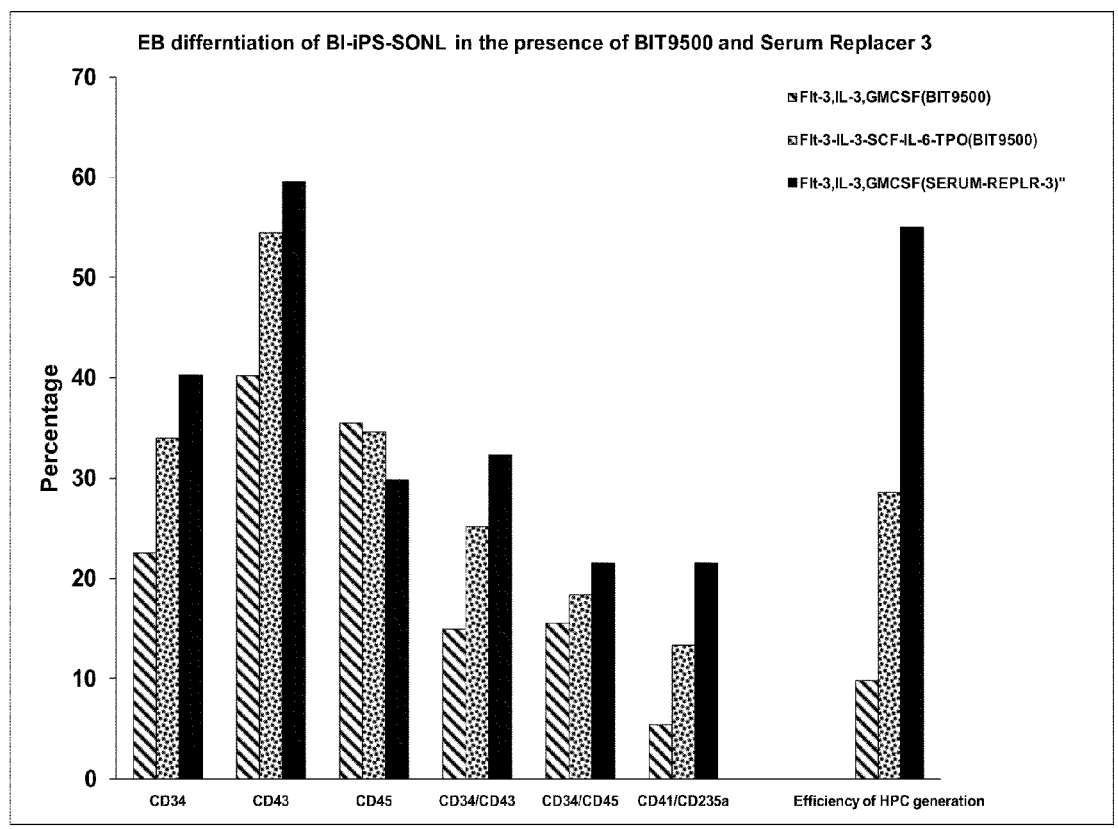
FIG. 12: Increases in efficiency of differentiation of pluripotent cells into HPC were observed with modified EB2 combination (D) in (H1) and iPS(SONL) cell lines. The growth factors supplemented in the media are shown. Serum Replacer 3 (Sigma-Aldrich) was observed to outperform BIT-9500 (Stem Cell Technologies) as the serum replacer in the differentiation process.

Result: Supplementation of EB2 media with TPO, IL-6 and SCF further increased the efficiency of generating HPCs from 15 to 55% for iPS—SONL. H1 ES cells revealed an increase from 21-28% As shown in FIG. 11, increases in differentiation into HPC was observed using the above modified EB2 media in hESC(H1) and iPS(SONL) cell lines. FIG. 12 shows the increases in efficiency with modified EB2 combination (D) in (H1) and iPS (SONL) cell lines. Serum Replacer 3 (Sigma) was observed to outperform BIT-9500 as the serum replacer in the differentiation process.

Example 12

Evaluation of Hypoxia and Normoxia in Differentiation Culturing Conditions

Undifferentiated hESC's and iPSC's adapted to feeder free growth on Matrigel coated plates using mTeSR were maintained in the presence of 5% $O_2$ (hypoxic) and 20% $O_2$ (normoxic) conditions for least 5 passages.

EB differentiation was evaluated under the following conditions:
- (A) Undifferentiated cells maintained under Normoxic conditions and EB differentiation for 12 days under Normoxic conditions ("N-N");
- (B) Undifferentiated cells maintained under Normoxic conditions and EB differentiation for 12 days under Hypoxic conditions ("N-H");
- (C) Undifferentiated cells maintained under Hypoxic conditions and EB differentiation for 12 days under Normoxic conditions ("H-N");
- (D) Undifferentiated cells maintained under Hypoxic conditions and EB differentiation for 12 days under Hypoxic conditions ("H-H").

Cells were preconditioned for 1 day in TeSR without growth factors supplemented with 0.1 ng/ml TGF-β and 20 ng/ml FGF-2. 12-24 hours later the cells were placed in modified of EB basal media, as described in the above example, containing 50 ng/ml BMP4, 50 ng/ml VEGF, 25 ng/ml FGF-2 a cell density of one million cells per ml. The EB cultures were half fed every four days throughout the differentiation process. The EB cultures were partially reaggregated between days 4-5 of differentiation. The EB cultures were then further cultured in EB basal media supplemented with 25 ng/ml Flt-3 ligand, 25 ng/ml SCF, 25 ng/ml TPO, 10 ng/ml IL-3, 10 ng/ml IL-6. The EB cultures were half fed every four days throughout the differentiation process.

The EB cultures were harvested on day 12 of differentiation, and the percentages of cells which expressed each of CD34, CD43, CD45, CD31, CD41, and CD235a (Gly-a) were quantified. The efficiency of HPC generation was determined by dividing the absolute number of CD34+/CD43+ ouble positive cells on day 12 of EB differentiation by the starting number of ES/iPS cells.

Figure 13:
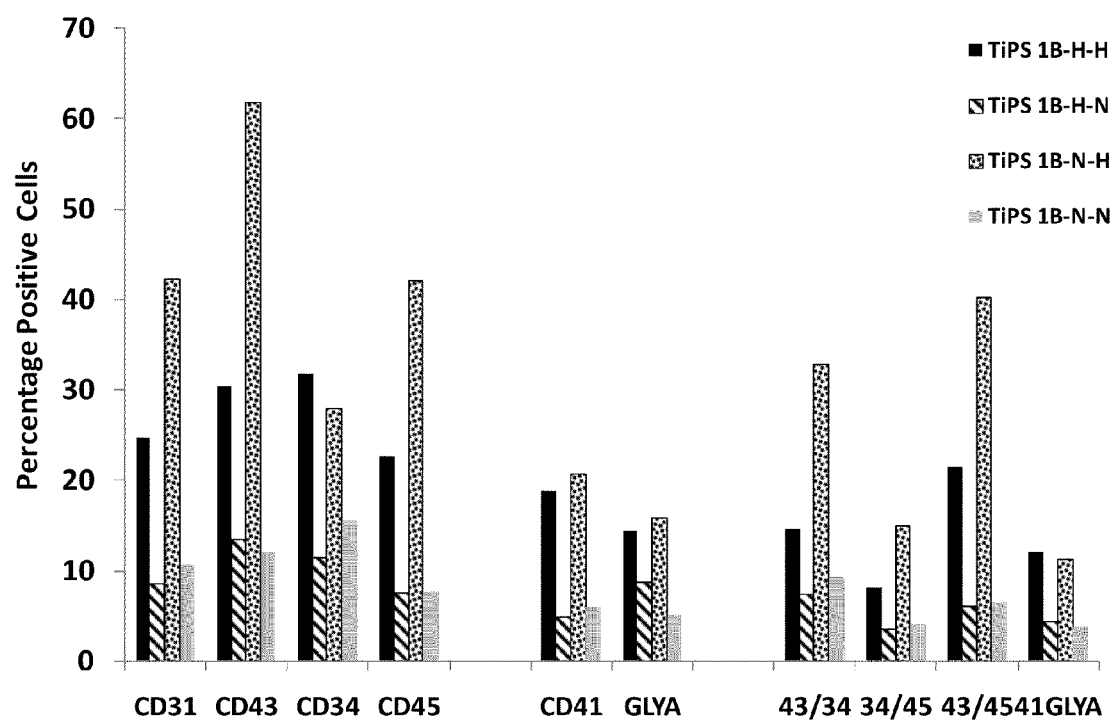
FIG. 13: Generation of HPC from iPS cells under normoxic ("N") and hypoxic ("H") conditions. The undifferentiated cell lines were maintained under normoxic or hypoxic conditions, and differentiation was performed under normoxic or hypoxic conditions. For example, "H-N" indicates that the cells were maintained under hypoxic conditions and differentiated under normoxic conditions.

Results: FIG. 13 shows the generation of HPC from iPS cells at normoxic and hypoxic conditions. The EB differentiation operated under hypoxic as well as normoxic conditions. Higher HPC levels were observed when EB differentiation was performed under hypoxic conditions. Maintenance of undifferentiated ES/iPS cells under hypoxic conditions did not add any significant benefit to the differentiation process. Glycophorin A expressing cells were reduced under normoxic conditions.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,815,450
U.S. Pat. No. 6,943,172
U.S. Pat. No. 7,348,339
U.S. Pat. No. 7,459,424
U.S. Application 61/015,813
U.S. Patent Appln. 2006/0084168
U.S. Patent Appln. 2007/0077654
Bashey et al. *Transfusion,* 47(11):2153-2160, 2007.
Bhardwaj et al., *Nat. Immunol.,* 2:172-180, 2001.
Bhatia et al., *J. Exp. Med.,* 189:1139-1148, 1999.
Chadwick et al., *Blood,* 102(3):906-915, 2003.
Davidson and Zon, *Curr. Top Dev. Biol.,* 50:45-60, 2000.
Davies et al., *Structure,* 8(2):185-195, 2000.
Drexler et al., *Growth Factors,* 22(2):71-3, 2004.
EP 00187371
Fadilah et al., *Stem Cells Dev.,* 16(5):849-856, 2007.
Gaur et al., *J. Thromb. Haemost.,* 4(2):436-42, 2006.
Hanna et al. *Science* 318(5858):1920-1923, 2007.
Huber et al., *Blood,* 92:4128-4137, 1998.
Ikenoya, et al., *J. Neurochem.,* 81:9, 2002.
Kadaja-Saarepuu et al., 2007
Kaufman et al., *Proc. Natl. Acad. Sci. USA,* 98:19, 2001.
Kiselyov et al., *Structure,* 11(6):691-701, 2003.
Lappalainen et al., *Clin. Experim. Allergy,* 37:1404-1414, 2007.
Lin et al., *Int. J. Mol. Med.* 17:833-839, 2006
Ludwig et al., *Nature Biotech.,* (2):185-187, 2006a.
Ludwig et al., *Nature Methods,* 3(8):637-646, 2006b.
Maekawa et al., *Science,* 285(5429):895-8, 1999.
Marshall et al., *Blood,* 96:1591-1593, 2000.
Nakagawa et al. *Nat. Biotechnol.,* 26(1):101-106, 2007.
PCT Appln. WO 0005/7913
PCT Appln. WO 0007/8351
PCT Appln. WO 0098/30679
PCT Appln. WO 2006/050330
Peng et al., *Cell Biology International,* 32(10): 1265-1271, 2008.
Ratajczak et al., *Br. J. Haematol.,* 93(4):772-782, 1996.
Remington: The Science and Practice of Pharmacy, 21$^{st}$ Ed., University of the Sciences in Philadelphia
Sasaki et al.; *Pharmacol. Ther.,* 93:225, 2002.
Schernthaner et al., *Blood,* 98:3784-3792, 2001.
Slukvin et al. In: *Directed Production of Specific Blood Lineages from Human Embryonic Stem Cells,* #33, ASCI/AAP Joint Meet. Posters, 2007.
Takahashi et al., *Cell,* 131(5):861-872, 2007.
Takahashi et al., *Nat. Protoc.,* 2(12):3081-3089, 2007.
Vodyanik et al., *Blood,* 108(6):2095-105, 2006.
Wagemaker et al., *Biotherapy,* 2(4):337-345, 1990.
Wang et al., *Nature Biotech.,* 25(3):317-318, 2007.
Yamamura et al., *Stem Cells,* 26(2):543-9, 2008.
Yu et al. *Science,* 318(5858):1917-1920, 2007.

What is claimed is:

1. A method of differentiating pluripotent cells into hematopoietic precursor cells or endothelial cells comprising the sequential steps of:
   a) culturing or maintaining a plurality of substantially undifferentiated pluripotent cells in a first defined media comprising at least one growth factor appropriate to maintain pluripotency;
   b) incubating the cells in a second defined media which is free or essentially free of BMP4, VEGF, IL-3, FIG ligand, and GMCSF, wherein said media comprises about 0.1 ng/ml or less of TGFβ and about 20 ng/ml or less of FGF-2, to precondition the cells for differentiation;
   c) culturing the preconditioned cells in a third defined media comprising an amount of BMP4 and VEGF sufficient to promote differentiation in a plurality of the cells; and
   d) culturing the cells in a fourth defined media comprising an amount of either (1) IL-3 and Flt3 ligand, or (2) VEGF, FGF-2 or an FGF-2 mimic, and IGF sufficient to expand and promote differentiation in a plurality of the cells;
   wherein a plurality of the pluripotent cells are differentiated into hematopoietic precursor cells or endothelial cells.

2. The method of claim 1, wherein the third defined media further comprises FGF-2 or an FGF-2 mimic.

3. The method of claim 1, wherein the fourth defined media comprises IL-3, Flt3 ligand, and GMCSF.

4. The method of claim 1, wherein the fourth defined media comprises IL-3, Flt3 ligand, and at least one of IL-6, SCF, or TPO.

5. The method of claim 4, wherein the fourth defined media further comprises IL-6, SCF, and TPO.

6. The method of claim 5, wherein the fourth defined media further comprises Serum Replacement 3.

7. The method of claim 6, wherein the pluripotent cells are iPSC.

8. The method of claim 1, wherein at least some of the cells are at least partially separated prior to step (b).

9. The method of claim 8, wherein the cells are substantially individualized prior to step (b).

10. The method of claim 9, wherein the cells are substantially individualized using an enzyme.

11. The method of claim 10, wherein the cells are contacted with a ROCK inhibitor and a trypsin inhibitor subsequent to said individualization.

12. The method of claim 11, wherein the ROCK inhibitor is selected from the list consisting of HA-100, H-1152, and Y-27632.

13. The method of claim 11, wherein the trypsin inhibitor is a soybean trypsin inhibitor.

14. The method of claim 1, wherein a plurality of the pluripotent cells form embryoid bodies (EBs).

15. The method of claim 14, wherein from about 200 to about 1000 cells per aggregate are used to generate at least one of said EBs.

16. The method of claim 1, wherein the method comprises culturing the cells at an atmospheric pressure of less than 20% oxygen.

17. The method of claim 16, wherein the method comprises culturing the cells at an atmospheric pressure of about 5% oxygen.

18. The method of claim 1, wherein said cells are partially or substantially reaggregated at least once.

19. The method of claim 18, wherein said cells are reaggregated after culture in the third defined media and prior to or during culture in the fourth defined media.

20. The method of claim 18, wherein said reaggregation comprises exposing said cells to trypsin or TRYPLE.

21. The method of claim 18, wherein said cells are exposed to a ROCK inhibitor subsequent to the reaggregation.

22. The method of claim 18, wherein said cells are cultured in a media essentially free of a ROCK inhibitor subsequent to the reaggregation.

23. The method of claim 18, wherein the method further comprises culturing the cells at an atmospheric pressure of less than about 20% oxygen, and wherein from about 200 to about 1000 cells per aggregate are used to generate a plurality of embryoid bodies (EBs).

24. The method of claim 1, wherein the third defined media or the fourth defined media comprises Serum Replacement 3.

25. The method of claim 1, wherein the first defined media comprises TeSR, mTeSR, or mTeSR1.

26. The method of claim 25, wherein step (a) comprises culturing the cells on a matrix-coated surface.

27. The method of claim 26, wherein the matrix comprises laminin, vitronectin, gelatin, polylysine, thrombospondin or Matrigel™.

28. The method of claim 1, wherein the second defined media comprises TeSR-GF or X-vivo15 media.

29. The method of claim 28, wherein the second defined media further comprises about 0.1 ng/ml TGF-β and about 20 ng/ml FGF-2.

30. The method of claim 1, wherein step (b) comprises incubating the cells for a period of from about 12 hours to about 3 days.

31. The method of claim 1, wherein step (c) comprises culturing or differentiating the cells for a period of from about 4 to about 8 days.

32. The method of claim 1, wherein step (d) comprises culturing the cells for a period of at least 4 days.

33. The method of claim 32, wherein a plurality of the pluripotent cells are differentiated into myeloid progenitor cells.

34. The method of claim 33, wherein the myeloid progenitor cells co-express CD31, CD43, and CD45.

35. The method of claim 1, wherein the third defined media comprises about 10-50 ng/ml BMP4 and about 10-50 ng/ml VEGF.

36. The method of claim 35, wherein the third defined media further comprises about 10-50 ng/ml FGF-2.

37. The method of claim 1, wherein the fourth defined media comprises about 5-25 ng/ml IL-3 and about 10-50 ng/ml Flt3 ligand.

38. The method of claim 37, wherein the fourth media further comprises about 5-25 ng/ml GMCSF.

39. The method of claim 37, wherein the fourth media further comprises about 10-100 ng/ml TPO, 10-100 ng/ml SCF, about 5-25 ng/ml IL-6, and about 5-25 ng/ml IL-3.

40. The method of claim 1, wherein a plurality of the hematopoietic precursor cells express at least two cell markers selected from the list comprising CD43, CD34, CD31 and CD45.

41. The method of claim 40, wherein a plurality of the hematopoietic precursor cells express CD34, CD43, CD45 and CD31.

42. The method of claim 1, wherein one or more of the hematopoietic precursor cells are differentiated into an erythroid cell, a myeloid cell, or a lymphoid cell.

43. The method of claim 42, wherein one or more of the hematopoietic precursor cells are differentiated into a myeloid cell, wherein the myeloid cell is selected from the group consisting of macrophage, mast cell, erythrocyte, megakaryocyte/platelet, dendritic cell, and polymorph nuclear granulocyte.

44. The method of claim 43, wherein the one or more of the hematopoietic precursor cells are differentiated into a granulocyte selected from the list consisting of eosinophil, basophil, neutrophil, monocyte, and macrophage.

45. The method of claim 1, wherein method comprises culturing a plurality of said cells in a fifth defined media comprising one or more growth factor selected from the list consisting of IL-3, IL-6, SCF, EPO, and TPO, in an amount sufficient to promote differentiation of a plurality of the cells into erythroblasts.

46. The method of claim 1, wherein said method further comprises culturing a plurality of said cells in a fifth defined media, wherein the fifth defined media comprises one or more growth factor selected from the list consisting of SCF, IL-6, G-CSF, EPO, TPO, FGF2, IL-7, IL-11, IL-9, IL-13, IL-2, or M-CSF in an amount sufficient to promote expansion and further differentiation of the cells.

47. The method of claim 1, wherein a plurality of the cells are cultured in a fifth defined media comprising one or more growth factor selected from the list consisting of IL-7, SCF, and IL-2, in an amount sufficient to promote differentiation of the cells into NK cells.

48. The method of claim 43, wherein the method further comprises culturing a plurality of the cells in a fifth defined media comprising Fc chimeric Notch DLL-1 ligand and one or more growth factor selected from the list consisting of IL-7, SCF, and IL-2 in an amount sufficient to promote differentiation of the cells into T cells.

49. The method of claim 1, wherein said pluripotent cells are mammalian pluripotent cells.

50. The method of claim 49, wherein said mammalian pluripotent cells are human pluripotent cells.

51. The method of claim 50, wherein said human pluripotent cells are human embryonic stem cells (hESC).

52. The method of claim 51, wherein the hESC comprise cells selected from the list consisting of H1, H9, hES2, hES3, hES4, hESS, hES6, BG01, BG02, BG03, HSF1, HSF6, H1, H7, H9, H13B, and H14.

53. The method of claim 50, wherein said human pluripotent cells are induced pluripotent cells (iPSC).

54. The method of claim 40, wherein the hematopoietic precursor cell expresses CD34, CD43, CD45, and CD31.

* * * * *

UNITED STATES PATENT AND TRADEMARK OFFICE
CERTIFICATE OF CORRECTION

PATENT NO. : 8,372,642 B2  
APPLICATION NO. : 12/715136  
DATED : February 12, 2013  
INVENTOR(S) : Deepika Rajesh and Rachel Lewis Page 1 of 1

It is certified that error appears in the above-identified patent and that said Letters Patent is hereby corrected as shown below:

In the Claims:

In claim 1, column 51, line 10, delete "FIG" and insert --Flt3-- therefor.

In claim 52, column 54, line 18, delete "hESS" and insert --hES5-- therefor.

Signed and Sealed this
Eighteenth Day of June, 2013

Teresa Stanek Rea
*Acting Director of the United States Patent and Trademark Office*